(12) United States Patent
Osada et al.

(10) Patent No.: US 8,025,696 B2
(45) Date of Patent: Sep. 27, 2011

(54) ARTIFICIAL MENISCUS AND PROCESS OF MAKING THEREOF

(75) Inventors: Yoshihito Osada, Sapporo (JP); Jian Ping Gong, Sapporo (JP); Kazunori Yasuda, Sapporo (JP)

(73) Assignee: National University Corporation Hokkaido University, Sapporo-shi, Hokkaido (JP)

( * ) Notice: Subject to any disclaimer, the term of this patent is extended or adjusted under 35 U.S.C. 154(b) by 999 days.

(21) Appl. No.: 11/629,925

(22) PCT Filed: Jun. 18, 2004

(86) PCT No.: PCT/JP2004/008599
§ 371 (c)(1),
(2), (4) Date: Mar. 16, 2007

(87) PCT Pub. No.: WO2006/013612
PCT Pub. Date: Feb. 9, 2006

(65) Prior Publication Data
US 2008/0119930 A1 May 22, 2008

(51) Int. Cl.
*A61F 2/08* (2006.01)
*A61F 2/00* (2006.01)
(52) U.S. Cl. .............................. 623/14.12; 523/113
(58) Field of Classification Search .......... 522/113; 523/113; 623/14.12
See application file for complete search history.

(56) References Cited

U.S. PATENT DOCUMENTS

| | | | |
|---|---|---|---|
| 4,071,508 A | 1/1978 | Steckler | |
| 5,264,495 A | 11/1993 | Irie et al. | |
| 5,580,929 A * | 12/1996 | Tanaka et al. | 525/218 |
| 5,644,049 A | 7/1997 | Giusti et al. | |
| 6,235,433 B1 | 5/2001 | Amano et al. | |
| 6,271,278 B1 | 8/2001 | Park et al. | |
| 6,565,768 B1 * | 5/2003 | Dentler et al. | 252/194 |
| 6,613,030 B1 | 9/2003 | Coles et al. | |
| 6,641,569 B1 | 11/2003 | Coles et al. | |
| 7,279,507 B2 | 10/2007 | Hu et al. | |
| 2001/0044482 A1 * | 11/2001 | Hu et al. | 523/106 |
| 2002/0022884 A1 * | 2/2002 | Mansmann | 623/14.12 |
| 2003/0083389 A1 * | 5/2003 | Kao et al. | 516/98 |

(Continued)

FOREIGN PATENT DOCUMENTS

JP 03-079608 A 4/1991

(Continued)

OTHER PUBLICATIONS

Corkhill et al., "Towards a synthetic articular cartilage", *J. Biomater. Sci. Polymer Edn*, vol. 4, No. 6, (1993), pp. 615-630.

(Continued)

*Primary Examiner* — Mark Eashoo
*Assistant Examiner* — David Karst
(74) *Attorney, Agent, or Firm* — Holtz, Holtz, Goodman & Chick, PC

(57) ABSTRACT

An artificial meniscus, a base material of which is a hydrogel having a semi-interpenetrating network structure or an inter-penetrating network structure (e.g., a linear polymer or a network structure composing the hydrogel is a polymer of an electrically charged unsaturated monomer and/or an electrically neutral unsaturated monomer or a crosslinked product thereof or/and a naturally occurring macromolecule or a crosslinked product thereof.), which can maintain moderate mechanical properties even in the case of application for an extended period of time between the joints where the severest mechanical environment is found in an organism, and which has no fear of causing osteoarthritis.

7 Claims, 40 Drawing Sheets

U.S. PATENT DOCUMENTS

| | | | |
|---|---|---|---|
| 2004/0029994 | A1* | 2/2004 | Cheng et al. .................. 523/113 |
| 2005/0147685 | A1 | 7/2005 | Osada et al. |
| 2008/0119930 | A1 | 5/2008 | Osada et al. |

FOREIGN PATENT DOCUMENTS

| | | | |
|---|---|---|---|
| JP | 03-165774 | A | 7/1991 |
| JP | 06 200224 | A | 7/1994 |
| JP | 8-319231 | A | 12/1996 |
| JP | 10-500148 | A | 1/1998 |
| JP | 10-032019 | A | 2/1998 |
| JP | 2000-231127 | A | 8/2000 |
| JP | 2002-351806 | A | 12/2000 |
| JP | 2001-131249 | A | 5/2001 |
| JP | 2002-501563 | A | 1/2002 |
| JP | 2002-105344 | A | 4/2002 |
| JP | 2002-212452 | A | 7/2002 |
| WO | WO 92/13566 | A1 | 8/1992 |
| WO | WO 94/01468 | A | 1/1994 |
| WO | WO 00/07636 | A | 2/2000 |

OTHER PUBLICATIONS

Santin et al., "Synthesis and characterization of a new interpenetrated poly(2-hydroxyethylmethacrylate)-gelatin composite polymer", *Biomaterials*, vol. 17, No. 15, (1996), pp. 1459-1467.

Kobayashi et al., "Preliminary study of polyvinyl alcohol-hydrogel (PVA-H) artificial meniscus", *Biomaterials*, vol. 24, pp. 639-647 (2003).

Grassman et al., "Morphogenetic Control of Calcite Crystal Growth in Sulfonic Acid Based Hydrogels", *Chem. Eur. J.*, vol. 9, No. 6, (2003), pp. 1310-1316.

Burugapalli et al., "Effect of composition of interpenentrating polymer network hydrogels based on poly(acrylic acid) and gelatin on tissue response: A quantitative in vivo study", *Biomedical Materials Research*, vol. 68A, No. 2, Feb. 1, 2004, pp. 210-218.

Nishimura et al., "Controlled Adsorption of Metal Ions by Thermo-Sensitive Hydrogels," *Polymer Preprints*, vol. 49, No. 12, p. 3471-3472, Sep. 8, 2000, Japan.

Zhang et al., *Macromolecules*, 2000, 33, 102-107.

Database WPI Section Ch, Week 199433, Thomas Scientific, London, GB; Class A12, AN 1994-269661 XP002490495, abstract of JP 06 200224 A (Nitto Chem. Ind. Co. Ltd.), Jul. 19, 1994.

English translation of International Preliminary Examination Report form PCT/IPEA/409 in International Application No. PCT/JP03/04556.

Gong et al., Double-Network Hydrogels with Extremely High Mechanical Strength, Advanced Materials 2003, 15, No. 14, Jul. 17, Wiley-VCH Verlag GmbH & Co., Weinheim, Germany.

Burugapalli et al., J. Polym Sci, Interpenetrating Polymer Networks Based on Poly(acrylic acid) and Gelatin. I: Swelling and Thermal Behavior, 2001, 82, pp. 217-227, John Wiley and Sons, Inc., New Jersey, USA.

Bigi et al., Biomaterials, Mechanical and Thermal Properties of Gelatin Films at Different Degrees of Glutaraldehyde Crosslinking, 22, 2001, pp. 763-768, Elsevier Science Ltd., Amsterdam, Netherlands.

* cited by examiner

[Fig. 1]
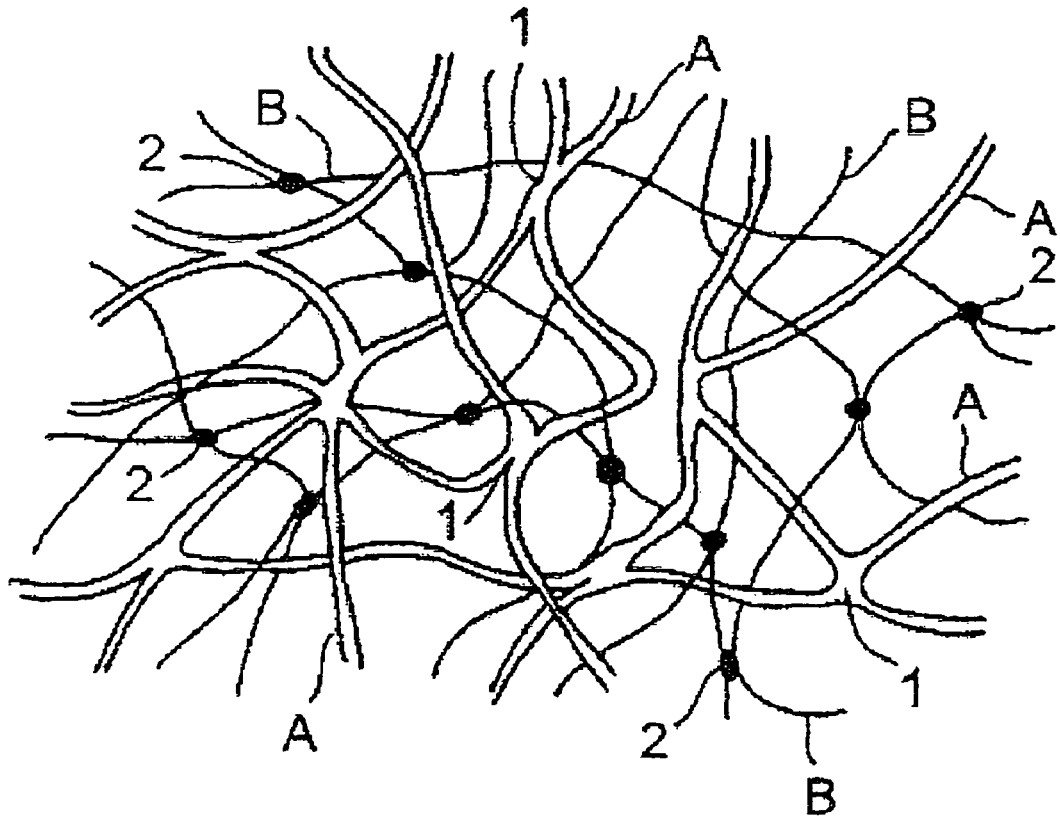
[Fig. 2]
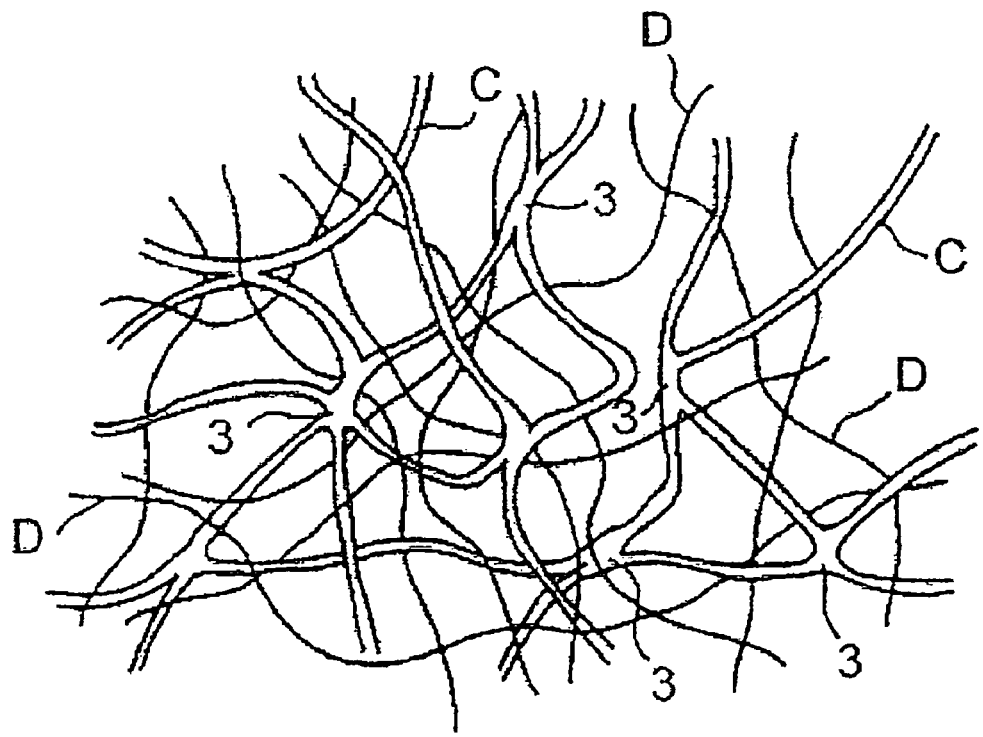

[Fig. 3]
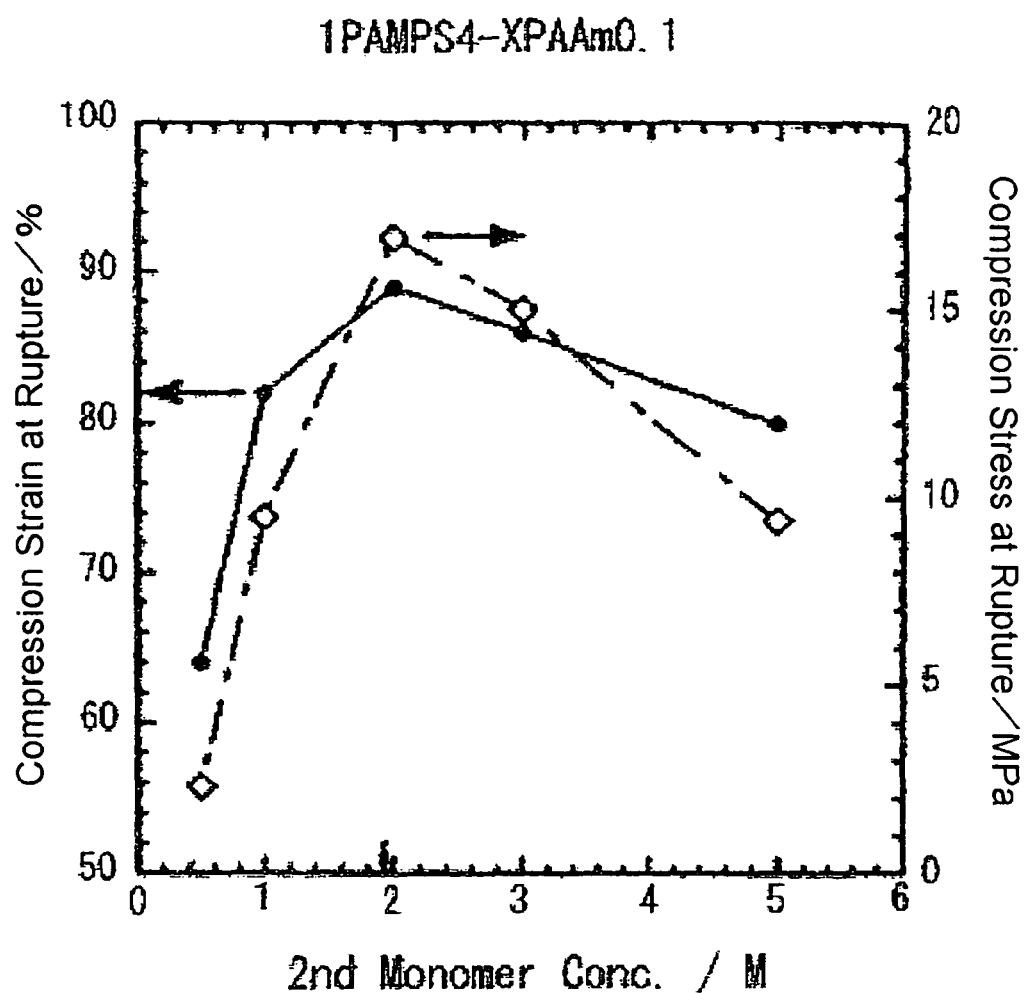

[Fig. 4]
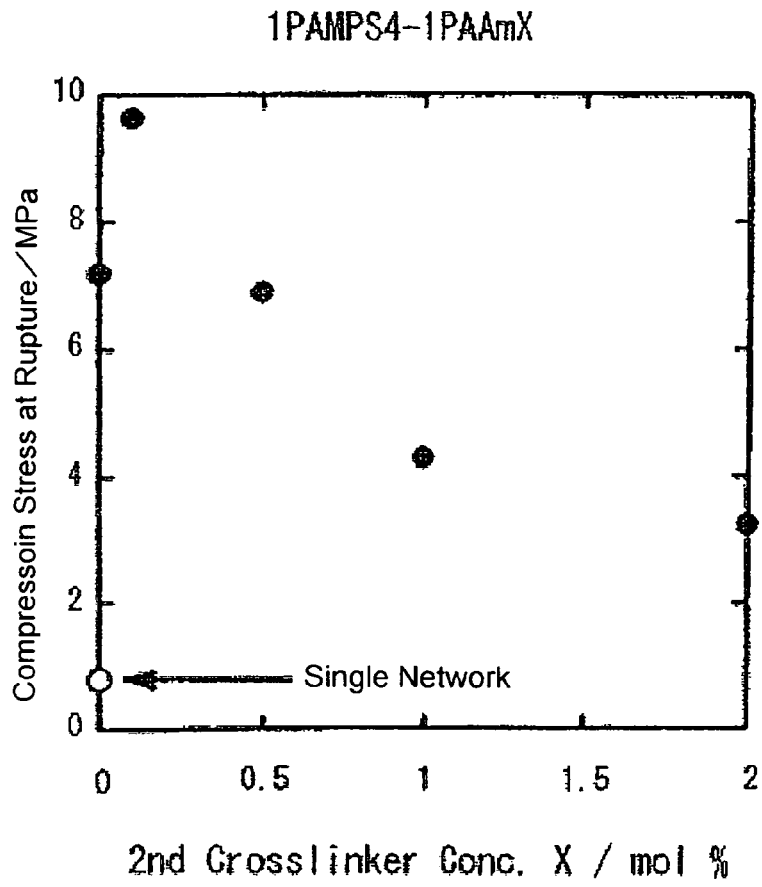
[Fig. 5]
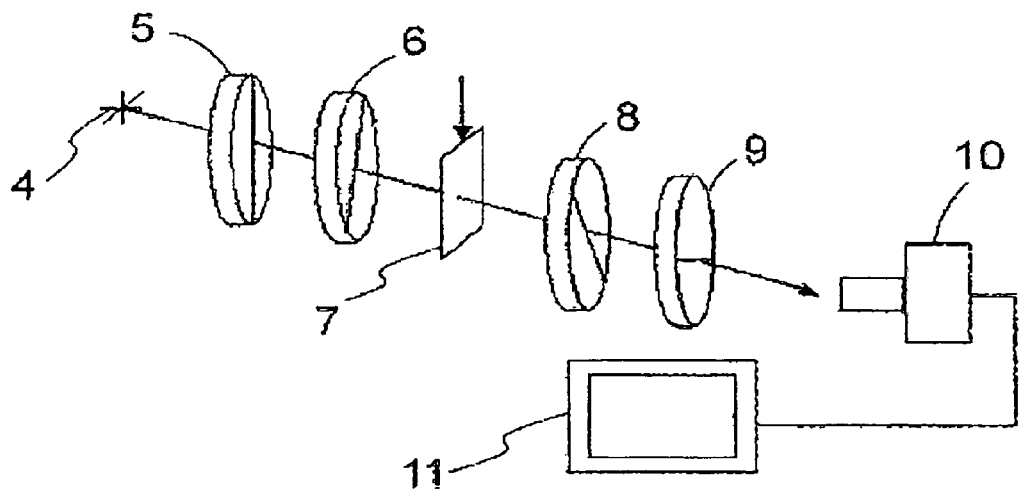

[Fig. 6]
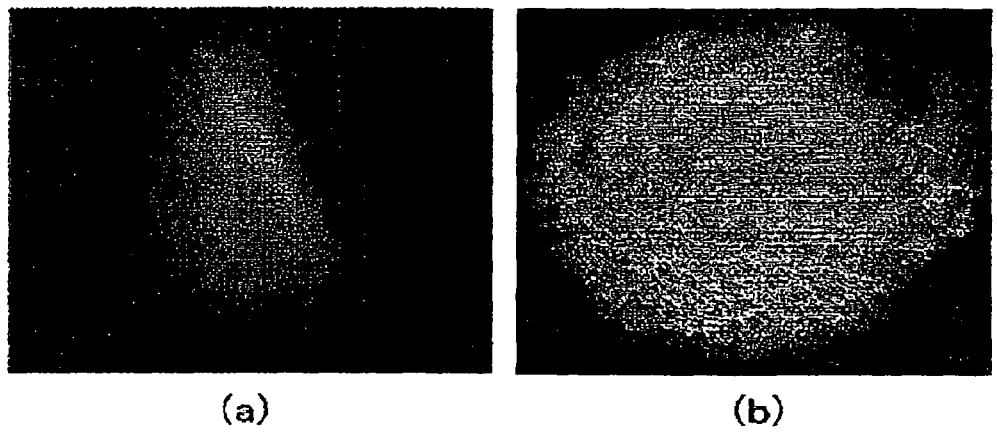
(a)            (b)

[Fig. 7]
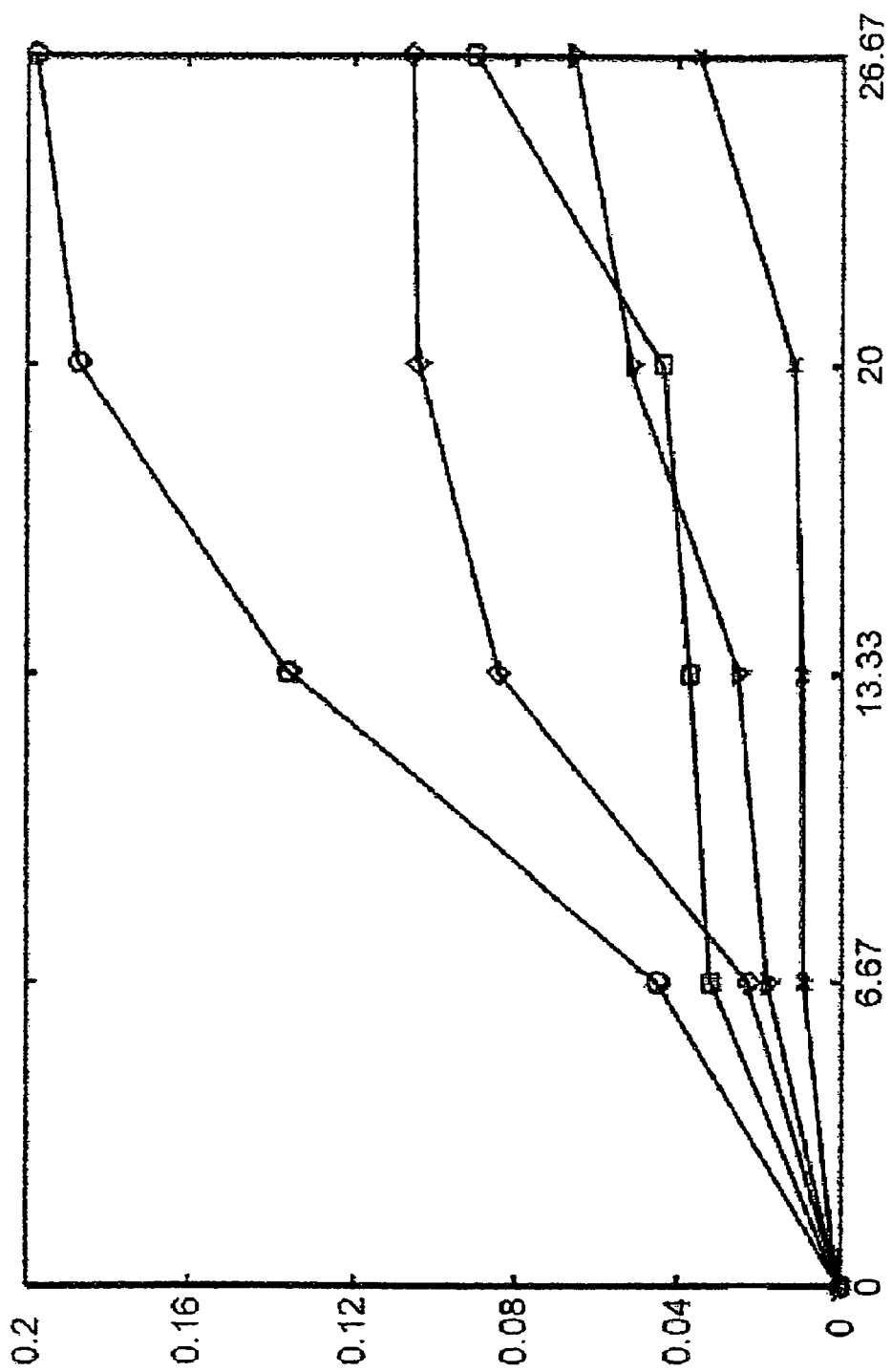

[Fig. 8]
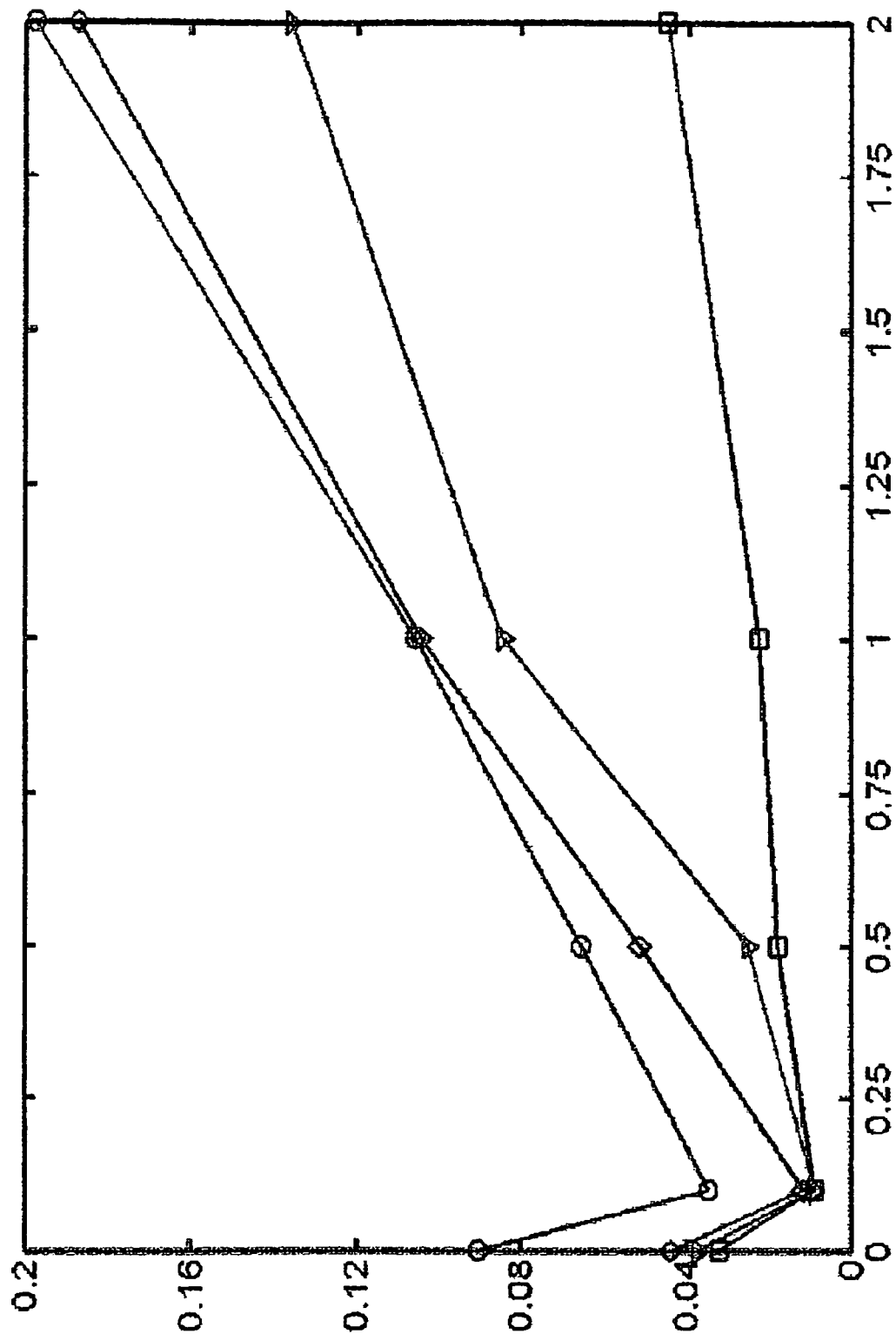

[Fig. 9]
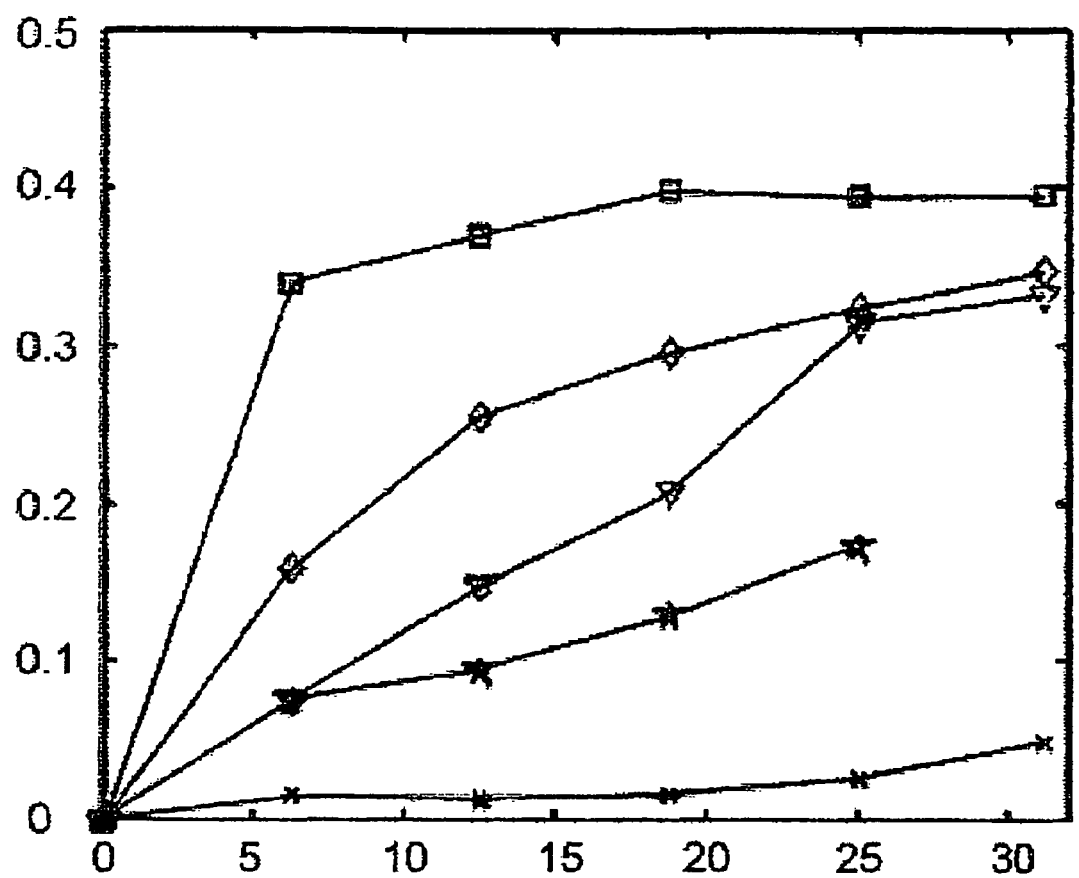

[Fig. 10]
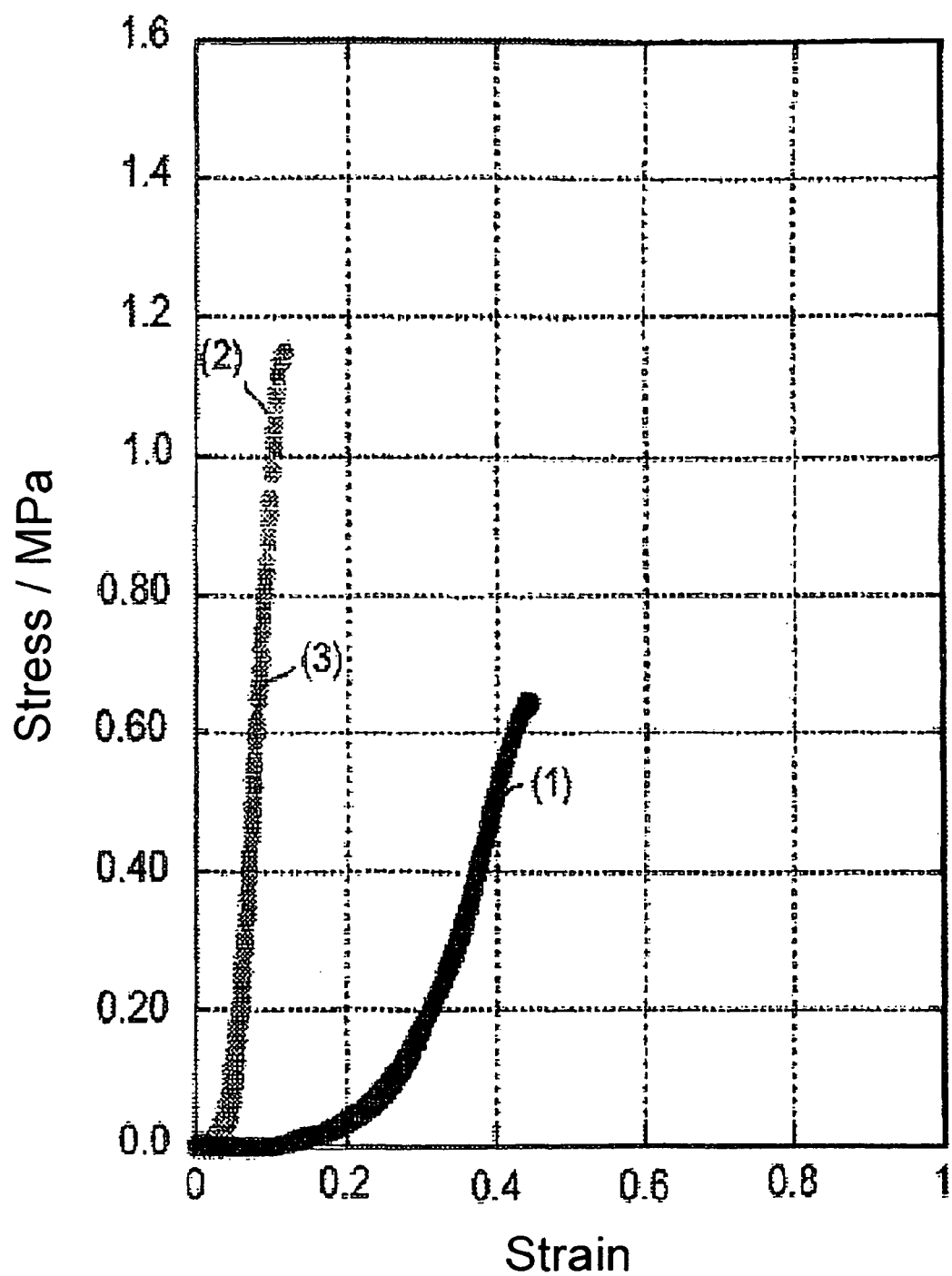

[Fig. 11]
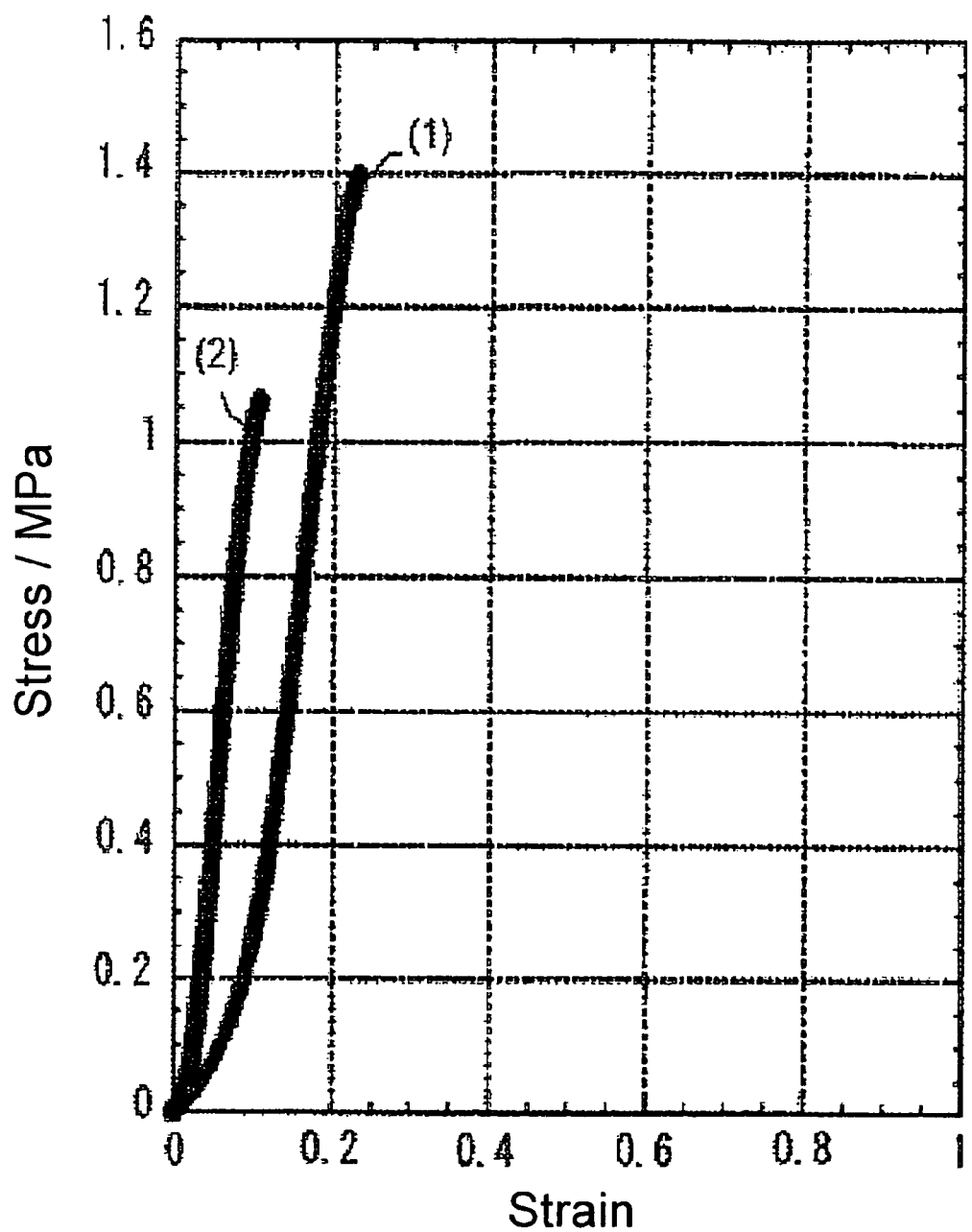

[Fig. 12]
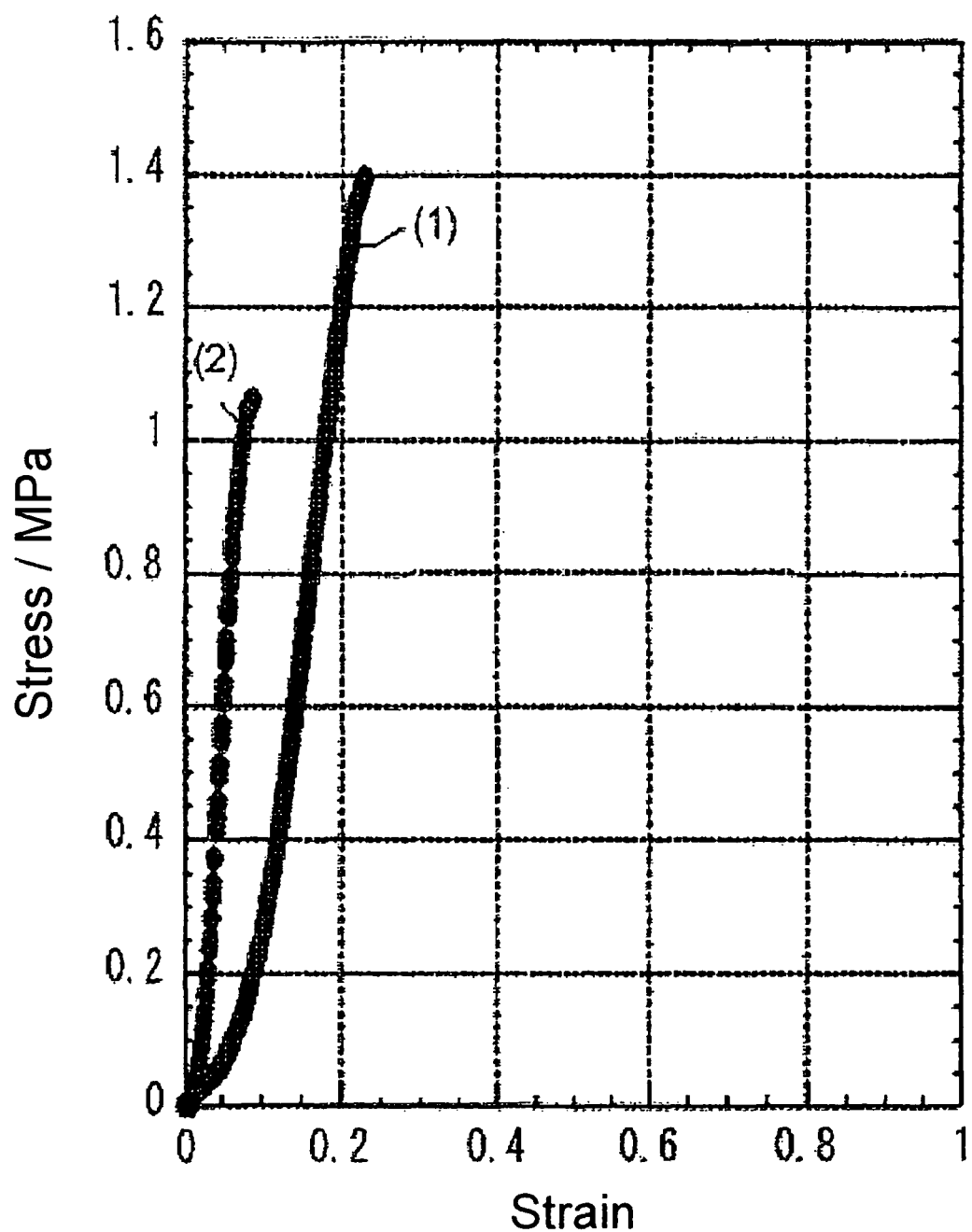

[Fig. 13]
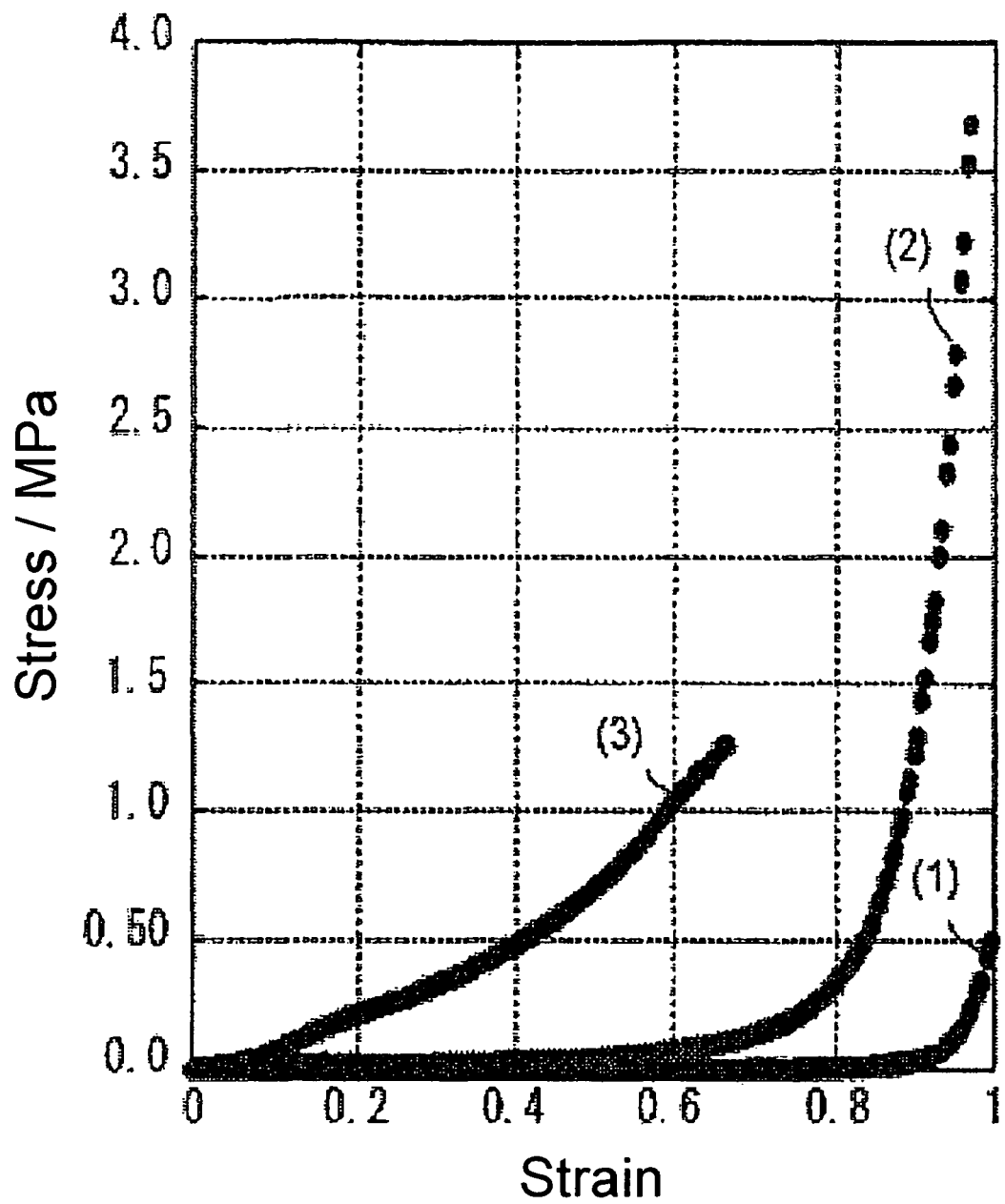

[Fig. 14]
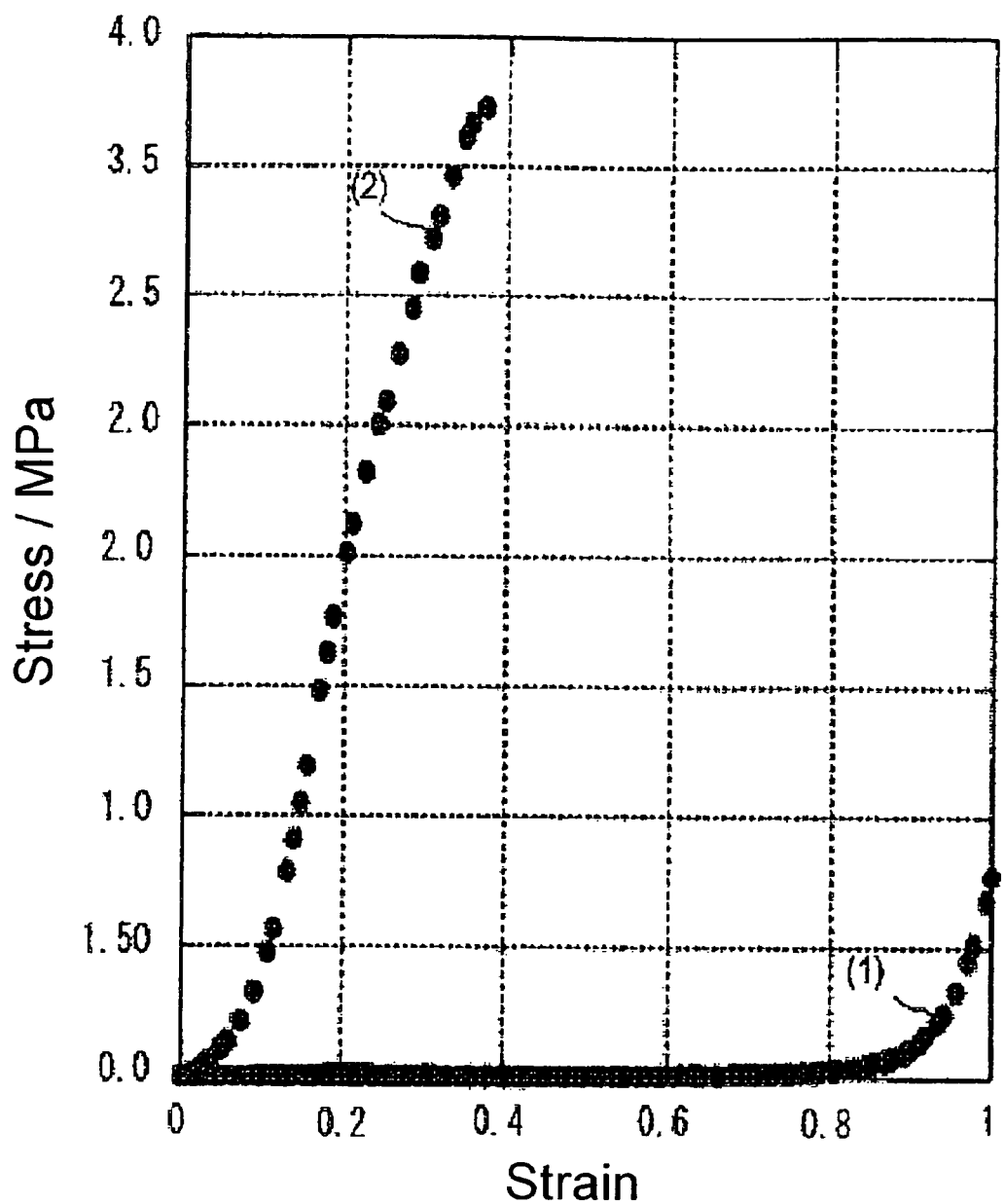

[Fig. 15]
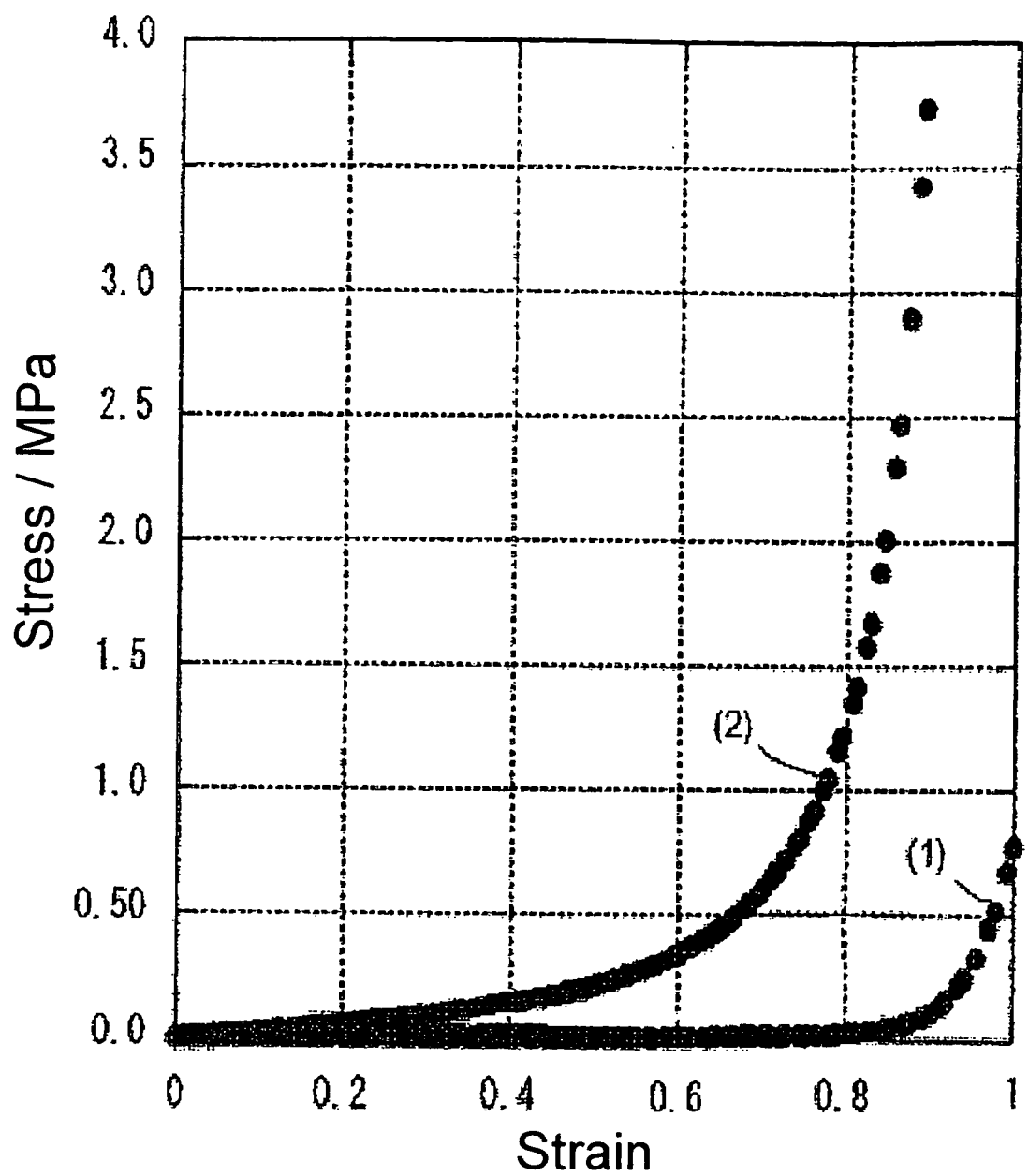

[Fig. 16]
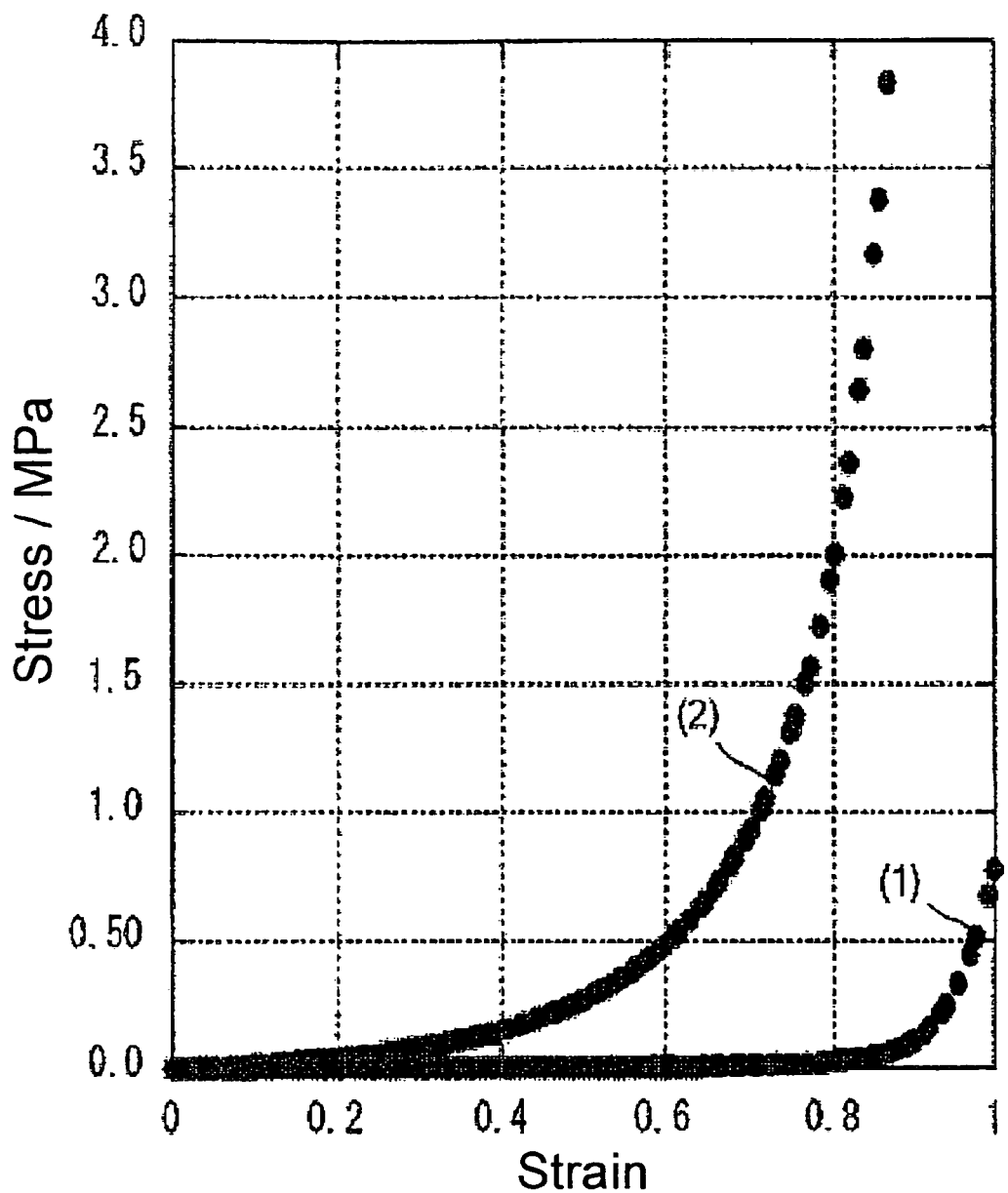

[Fig. 17]
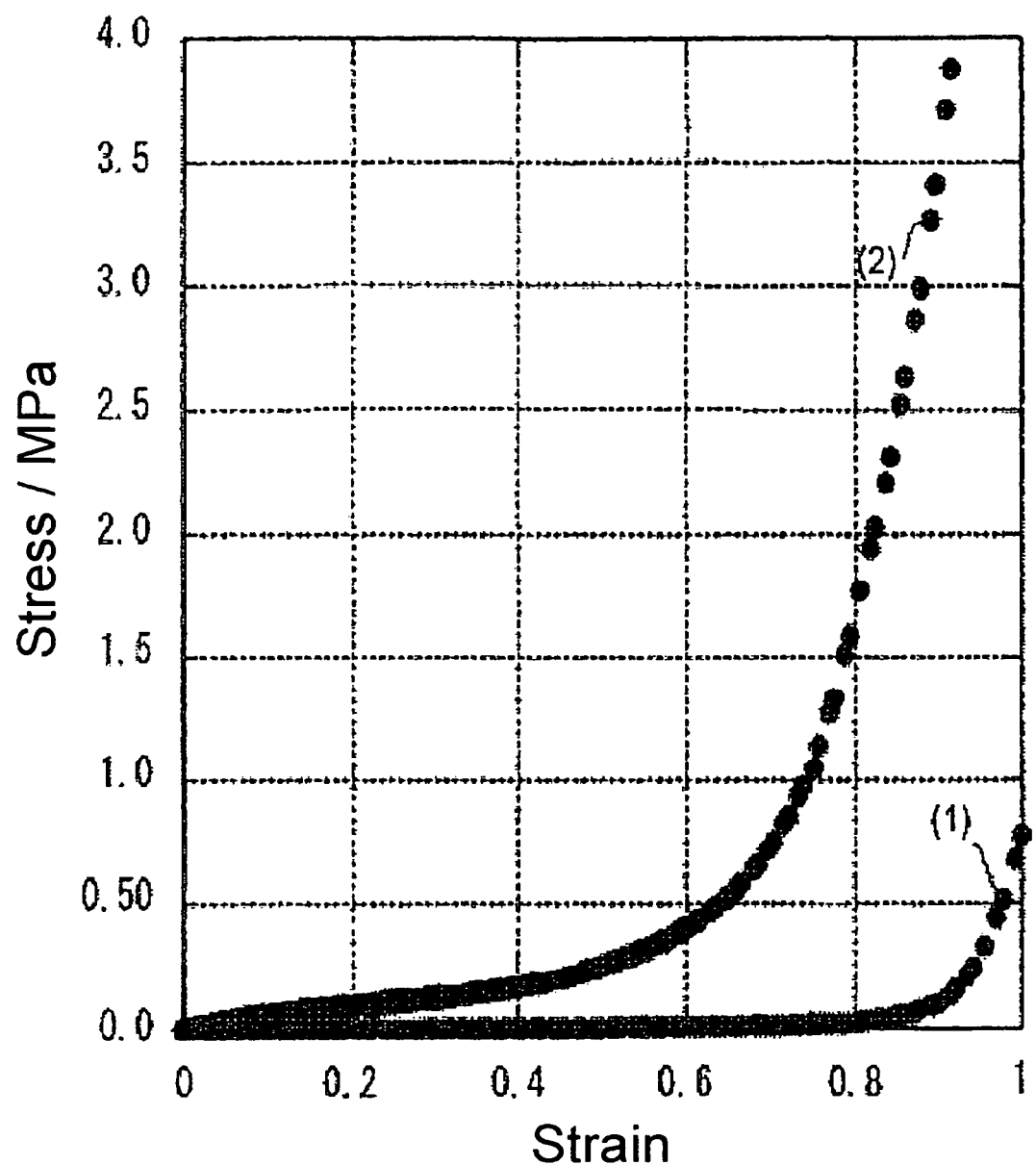

[Fig. 18]
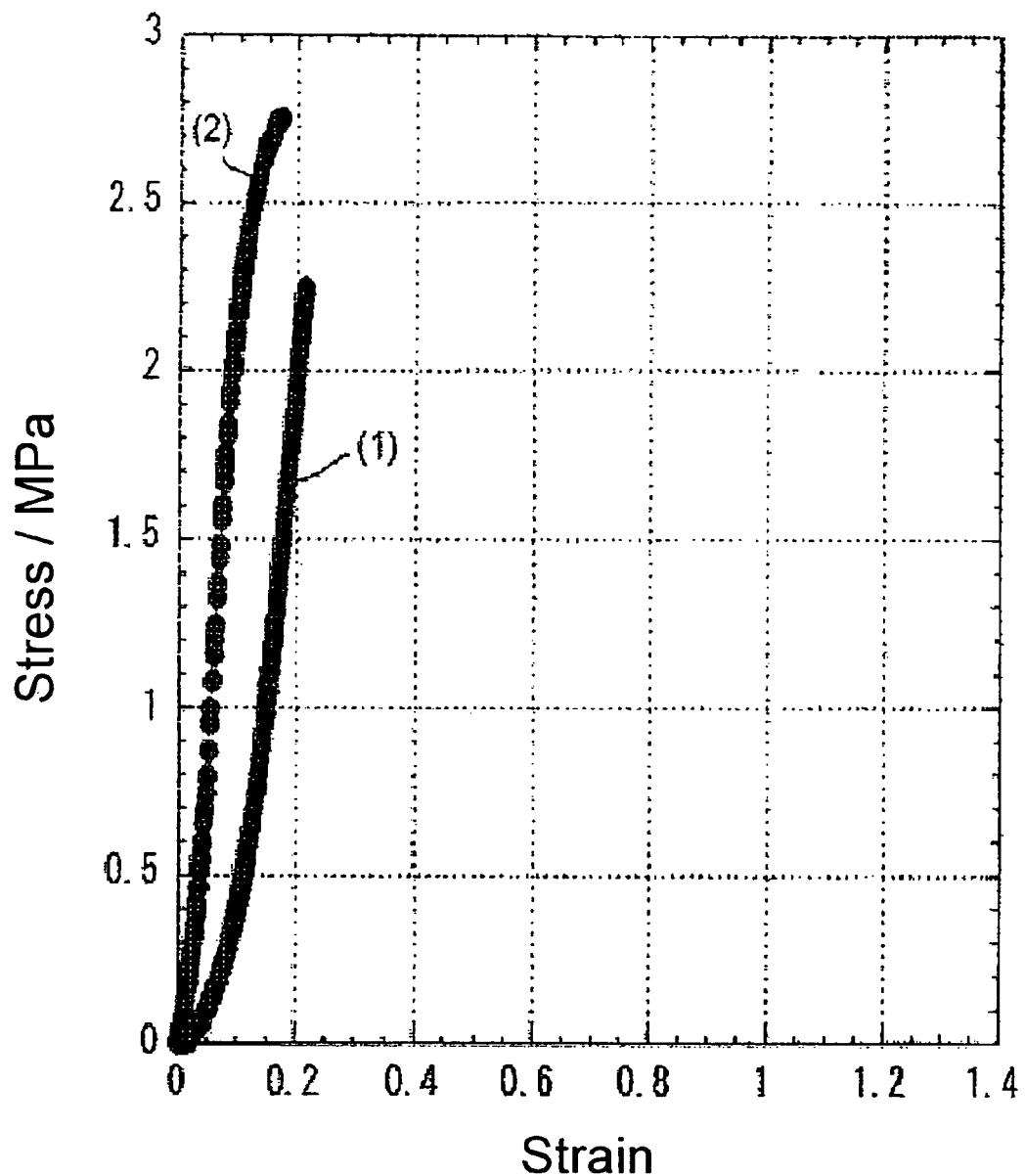

[Fig. 19]
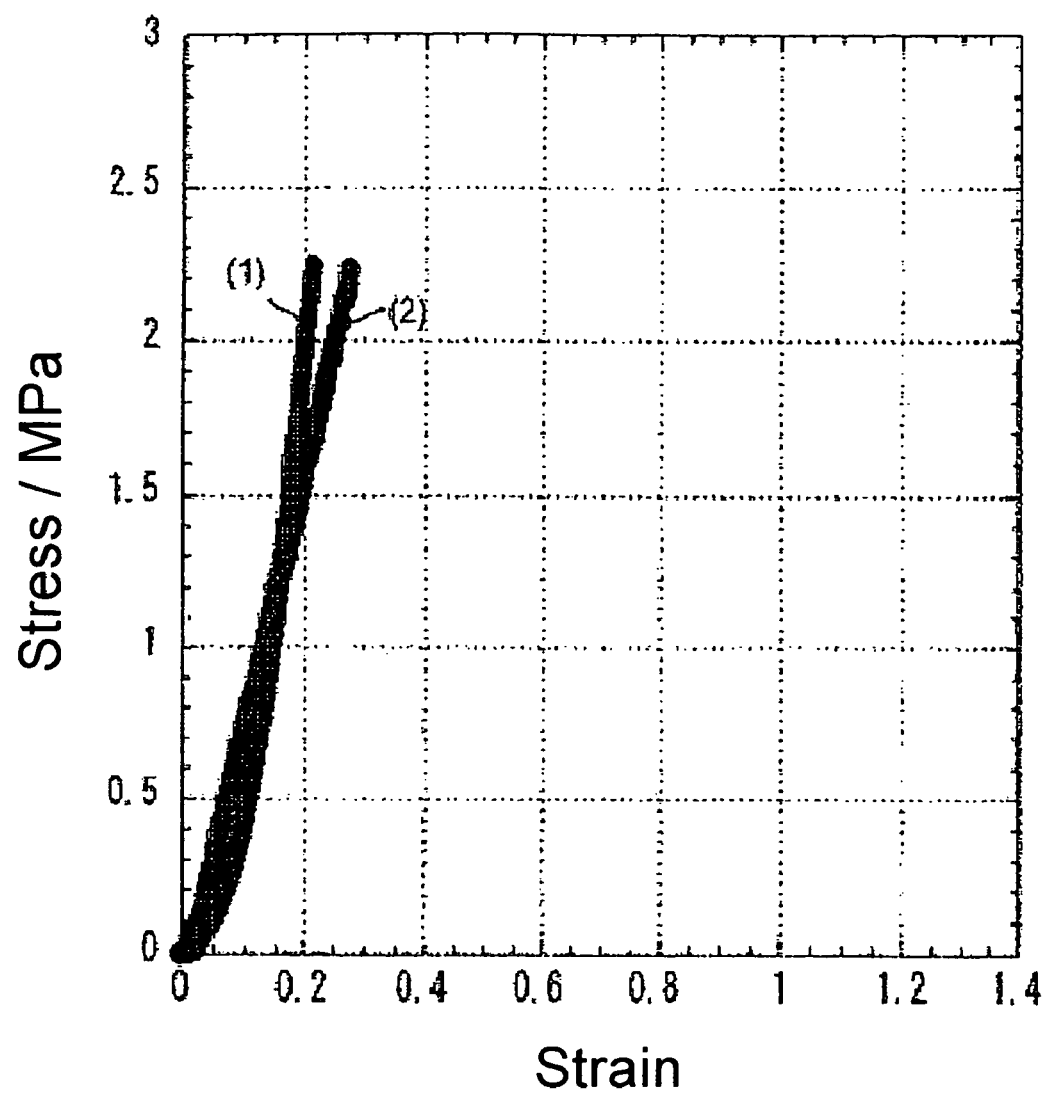

[Fig. 20]
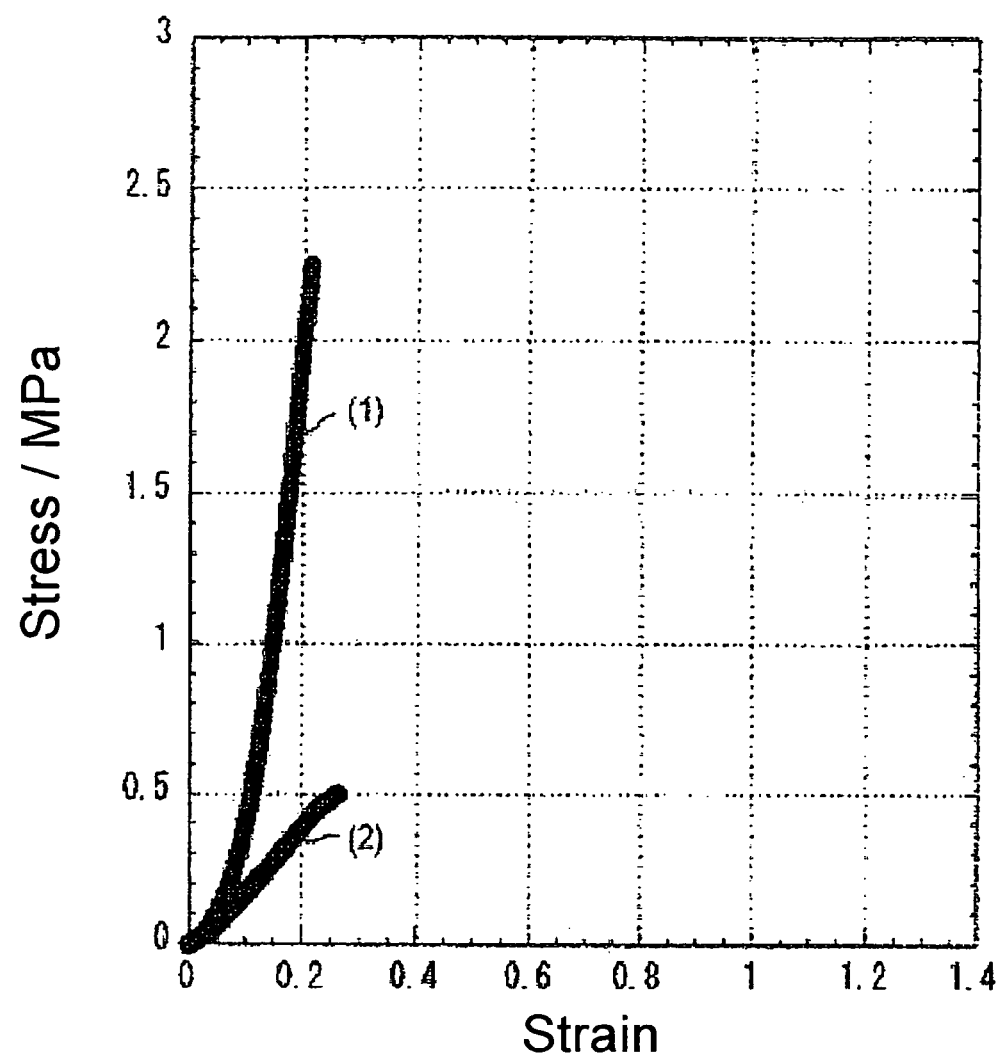

[Fig. 21]
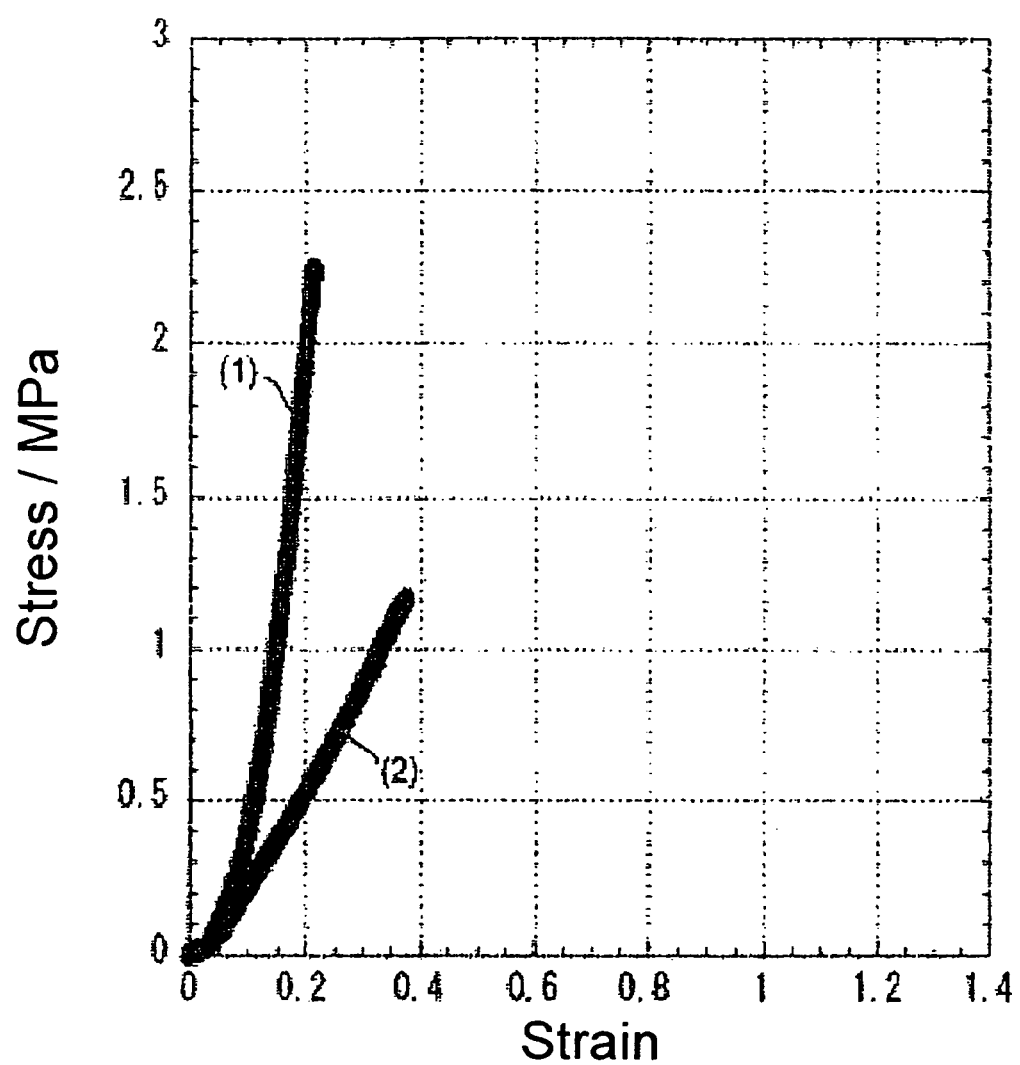

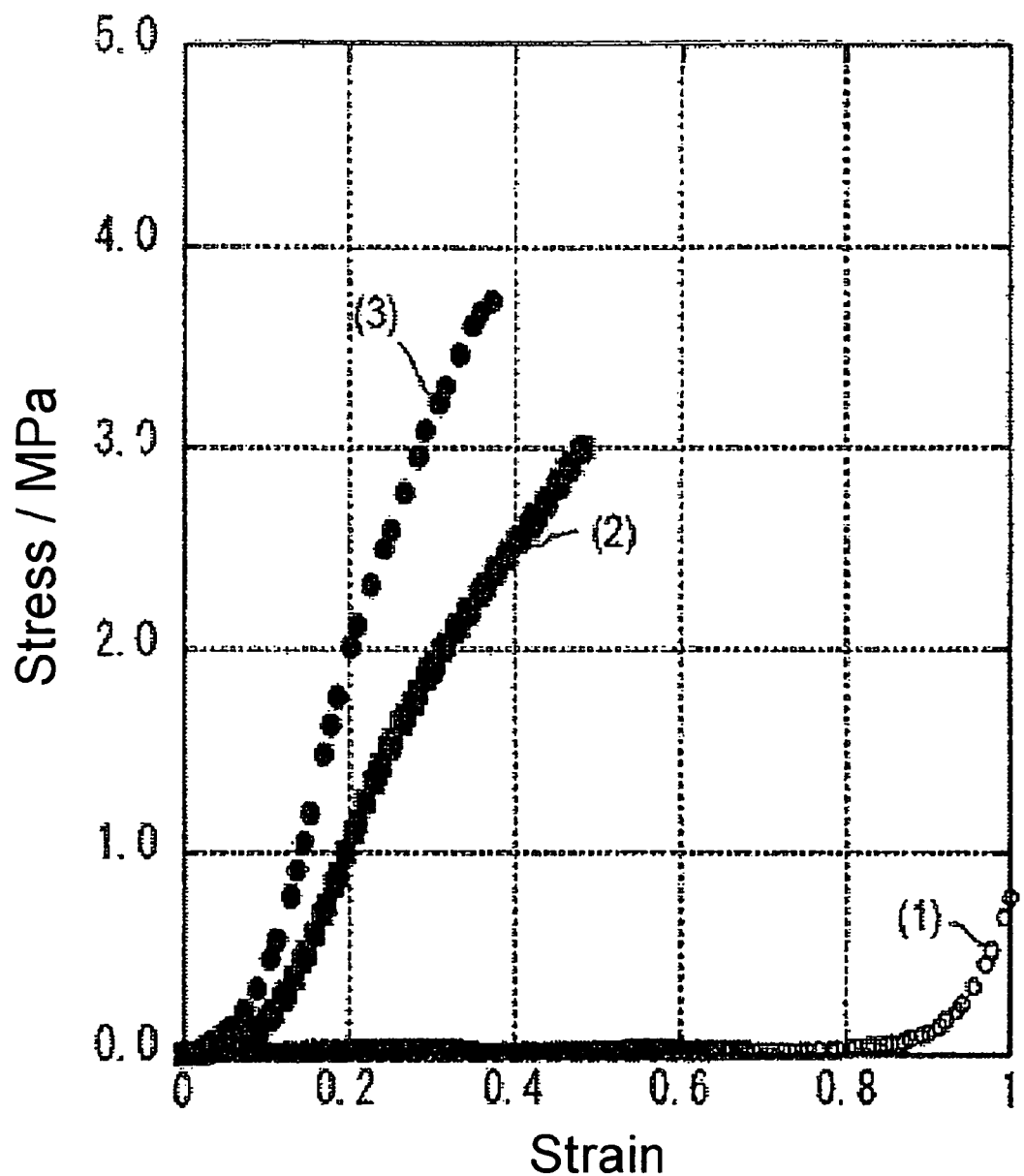
[Fig. 22]

[Fig. 23]
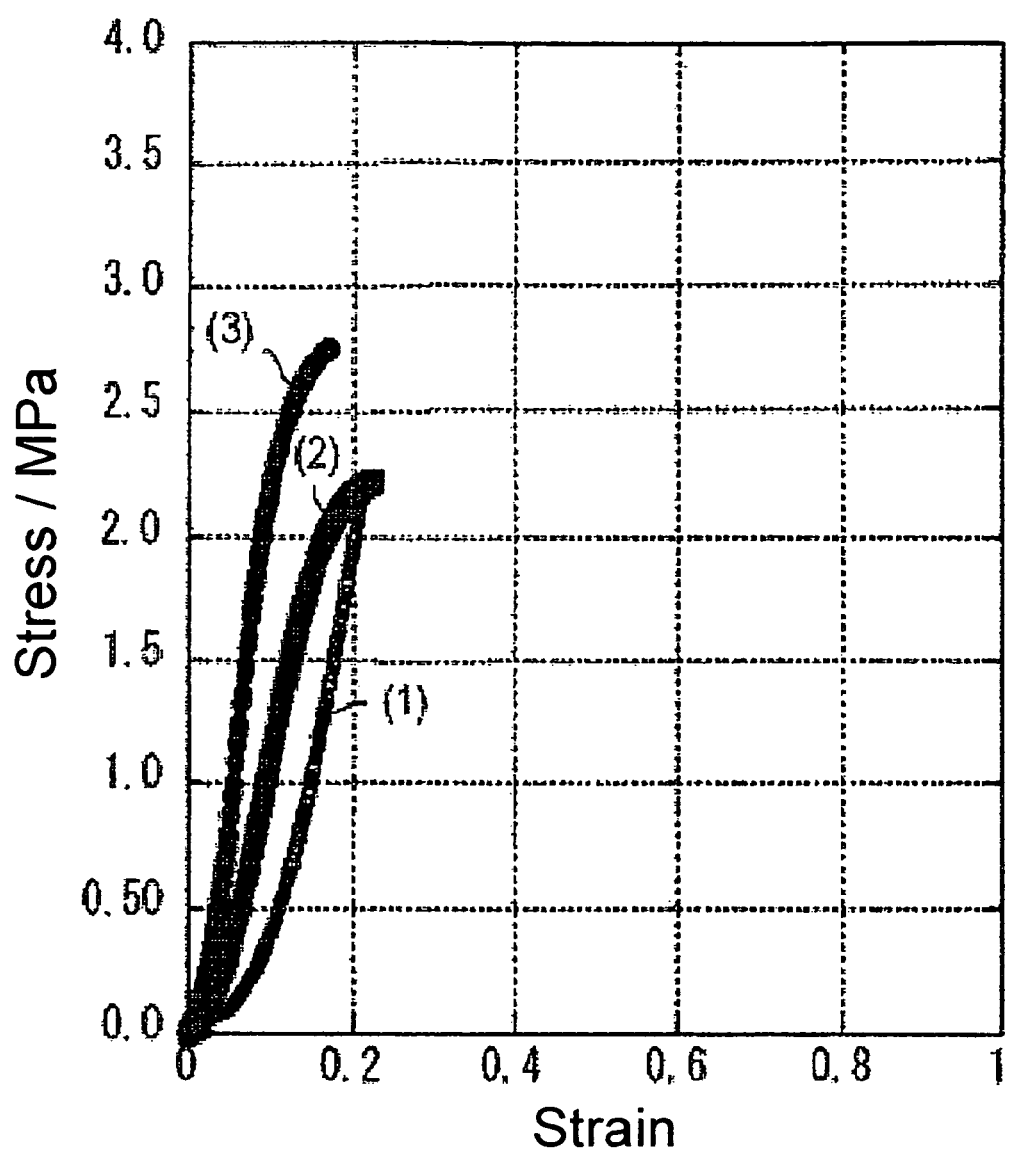

[Fig. 24]
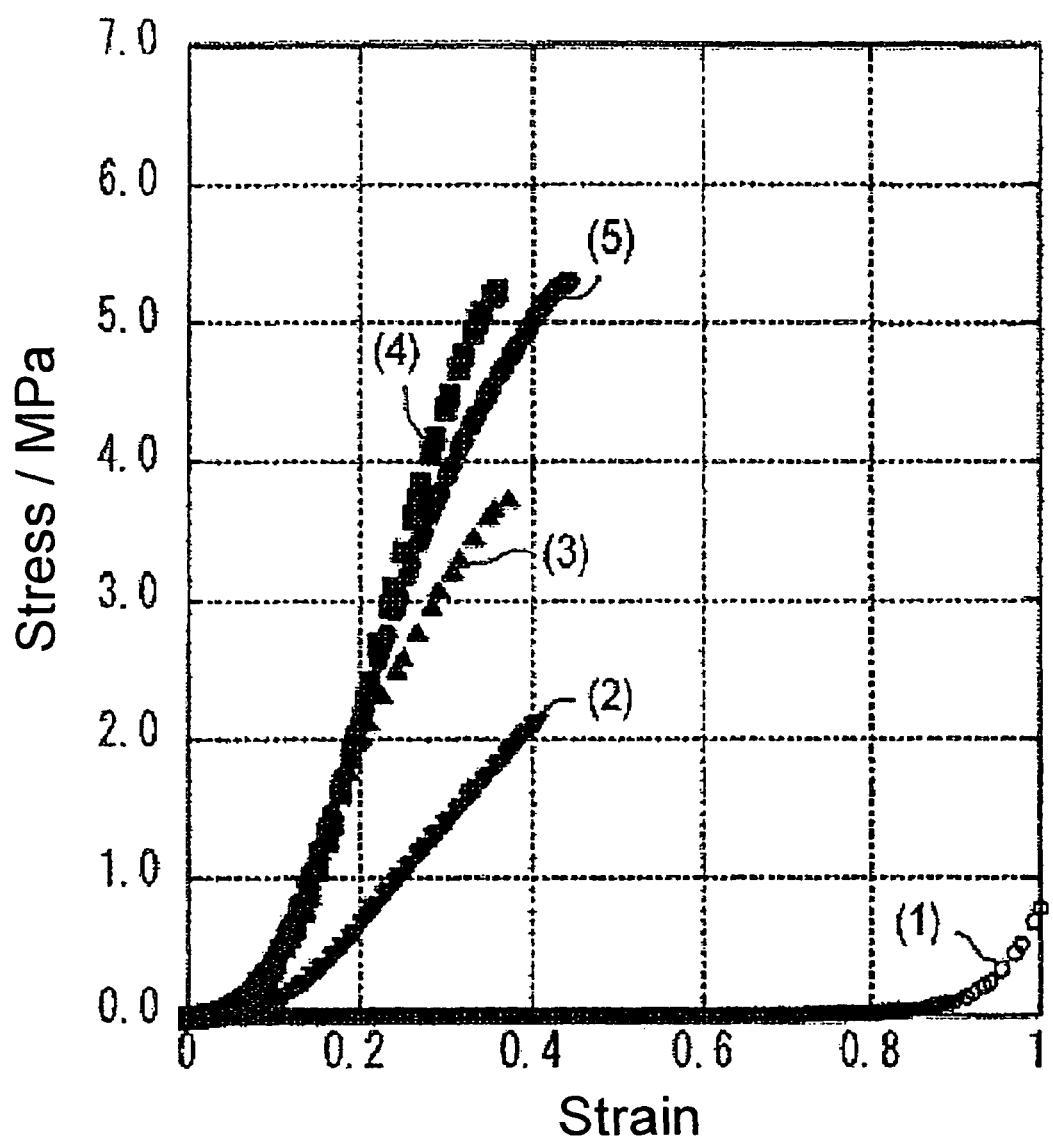

[Fig. 25]
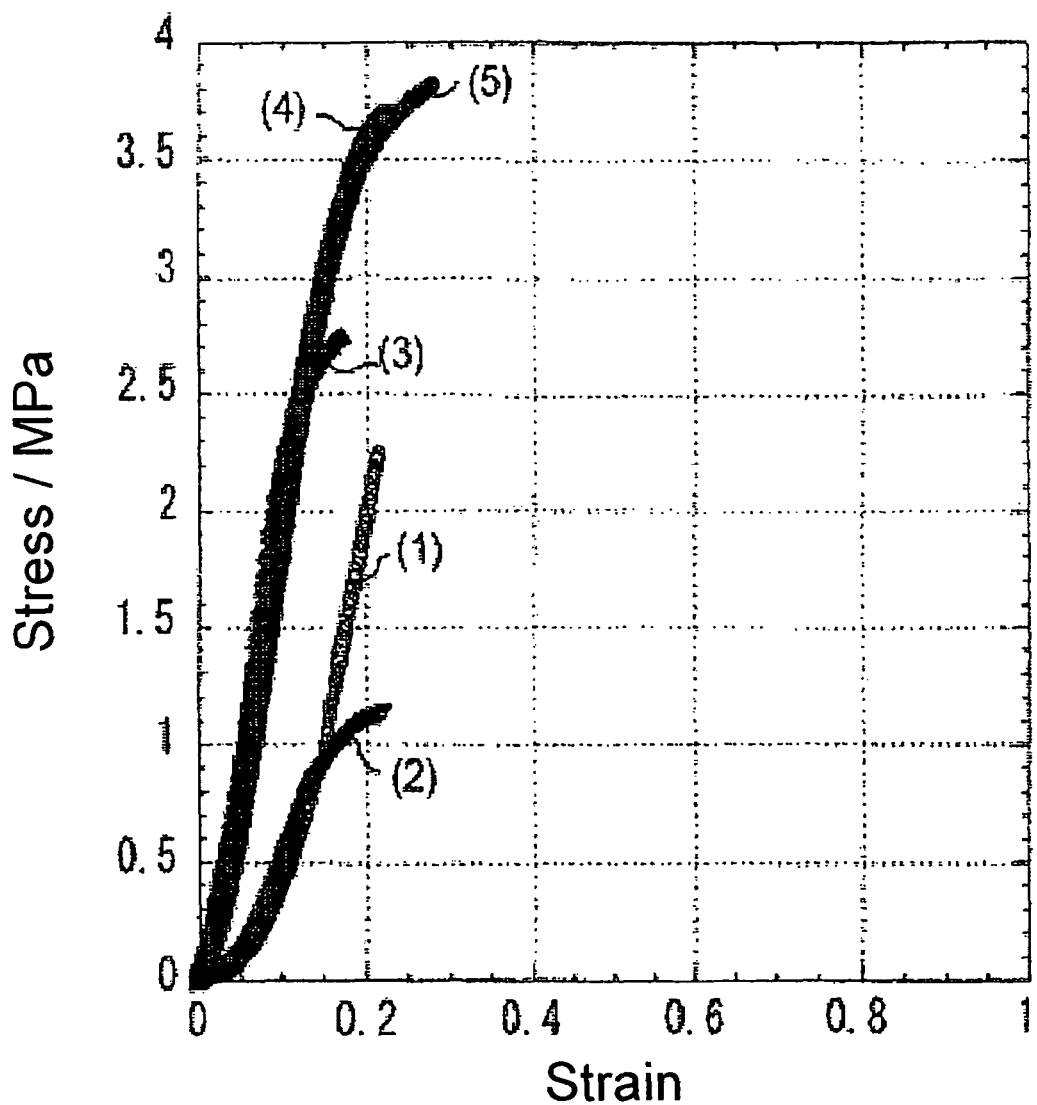

[Fig. 26]
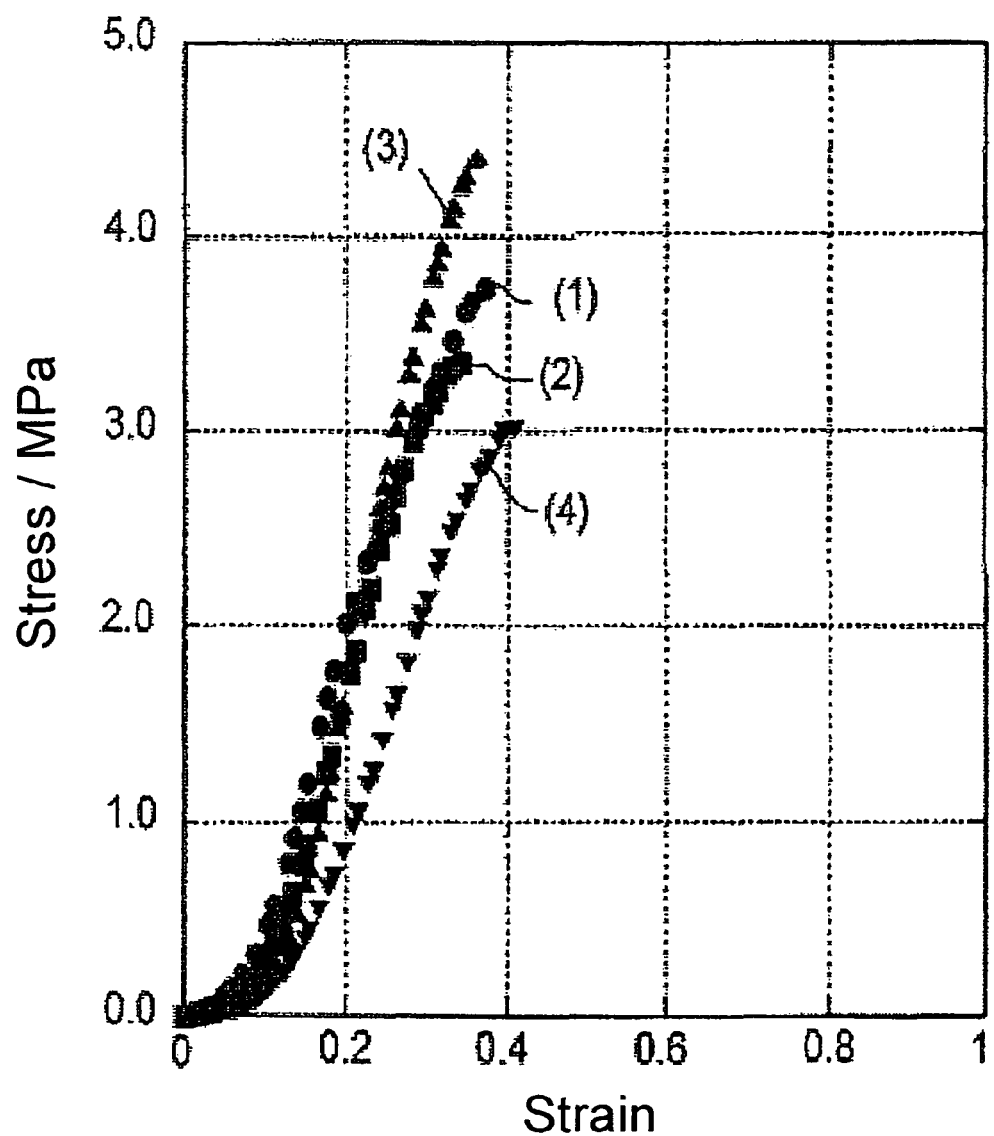

[Fig. 27]
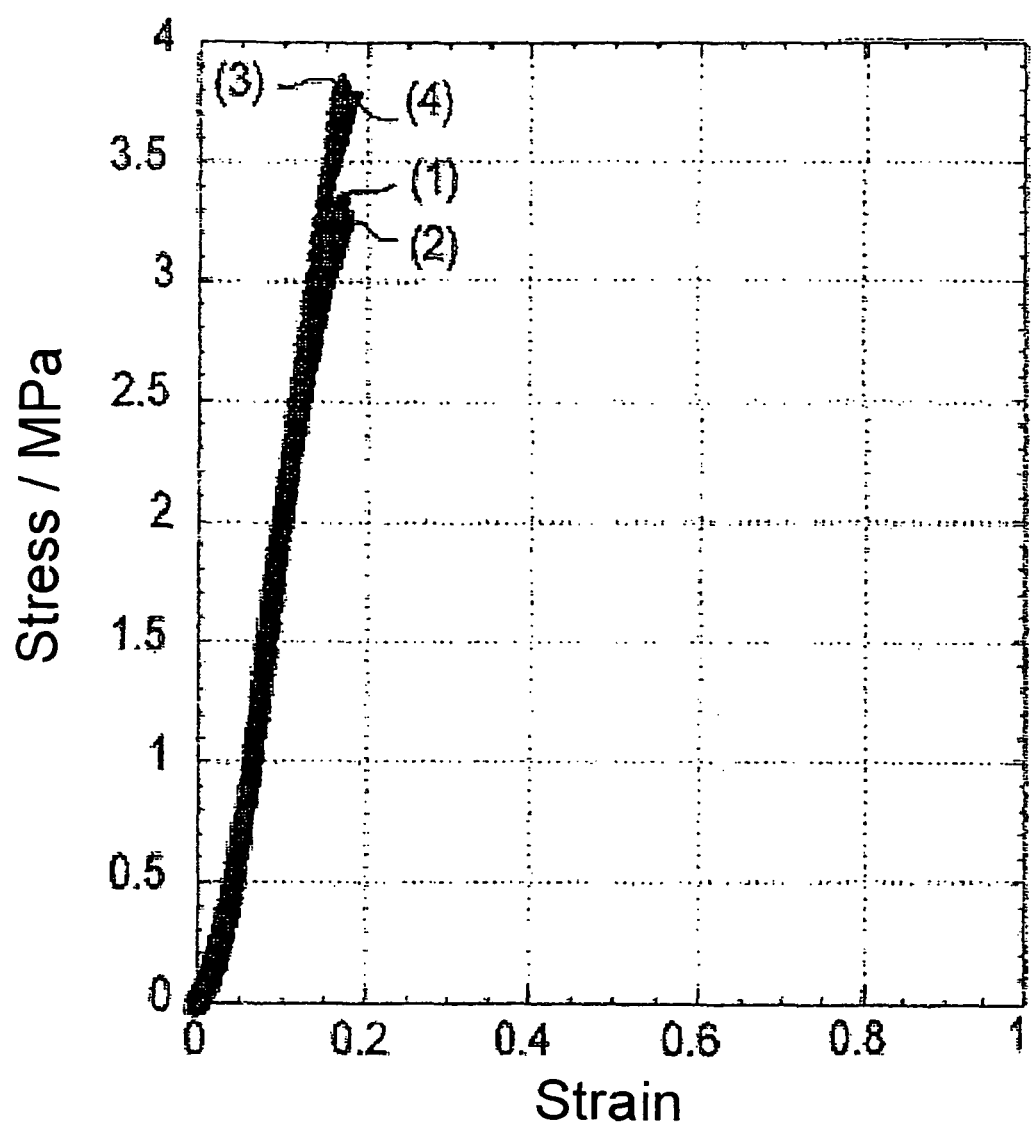

[Fig. 28]
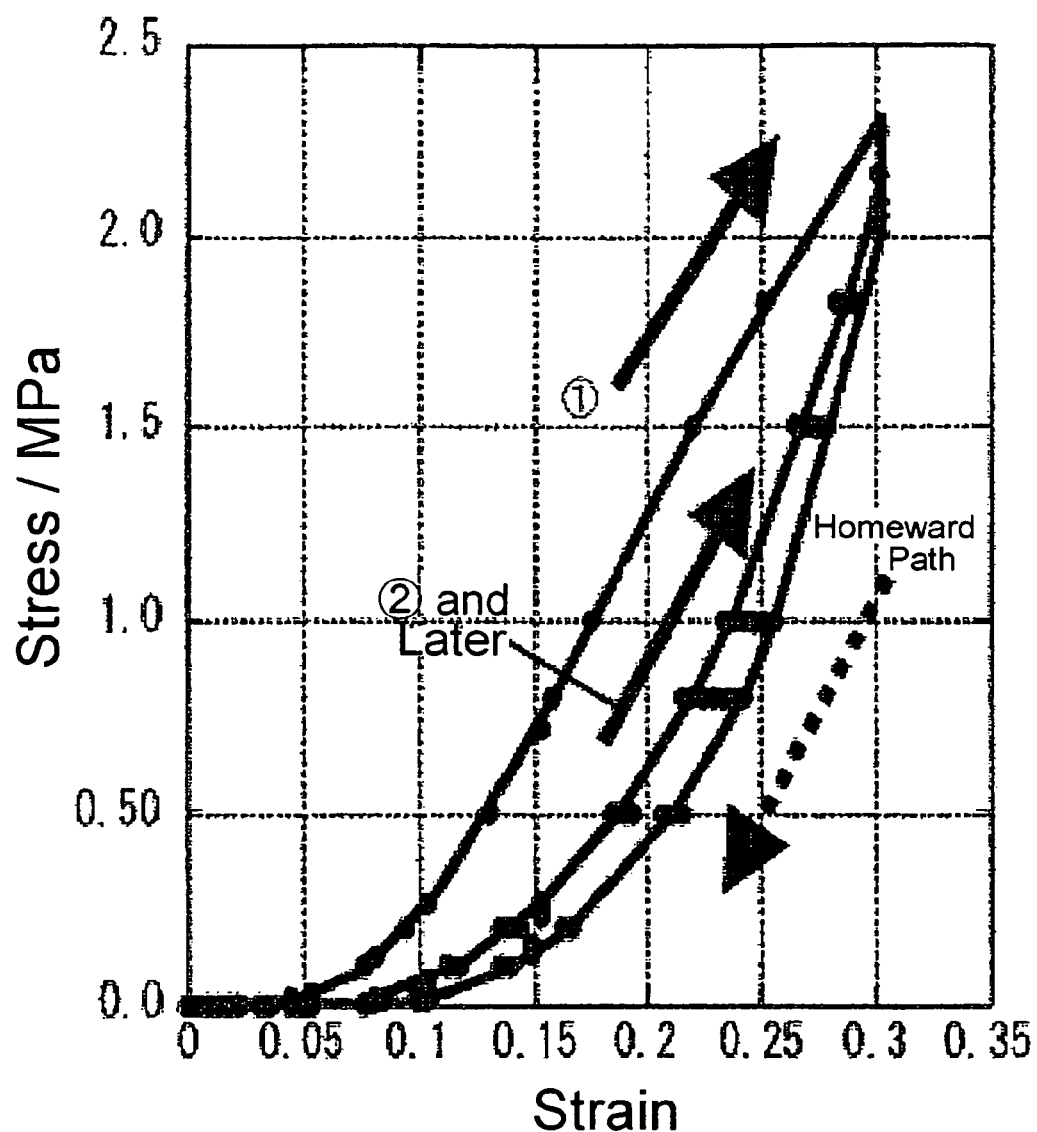

[Fig. 29]
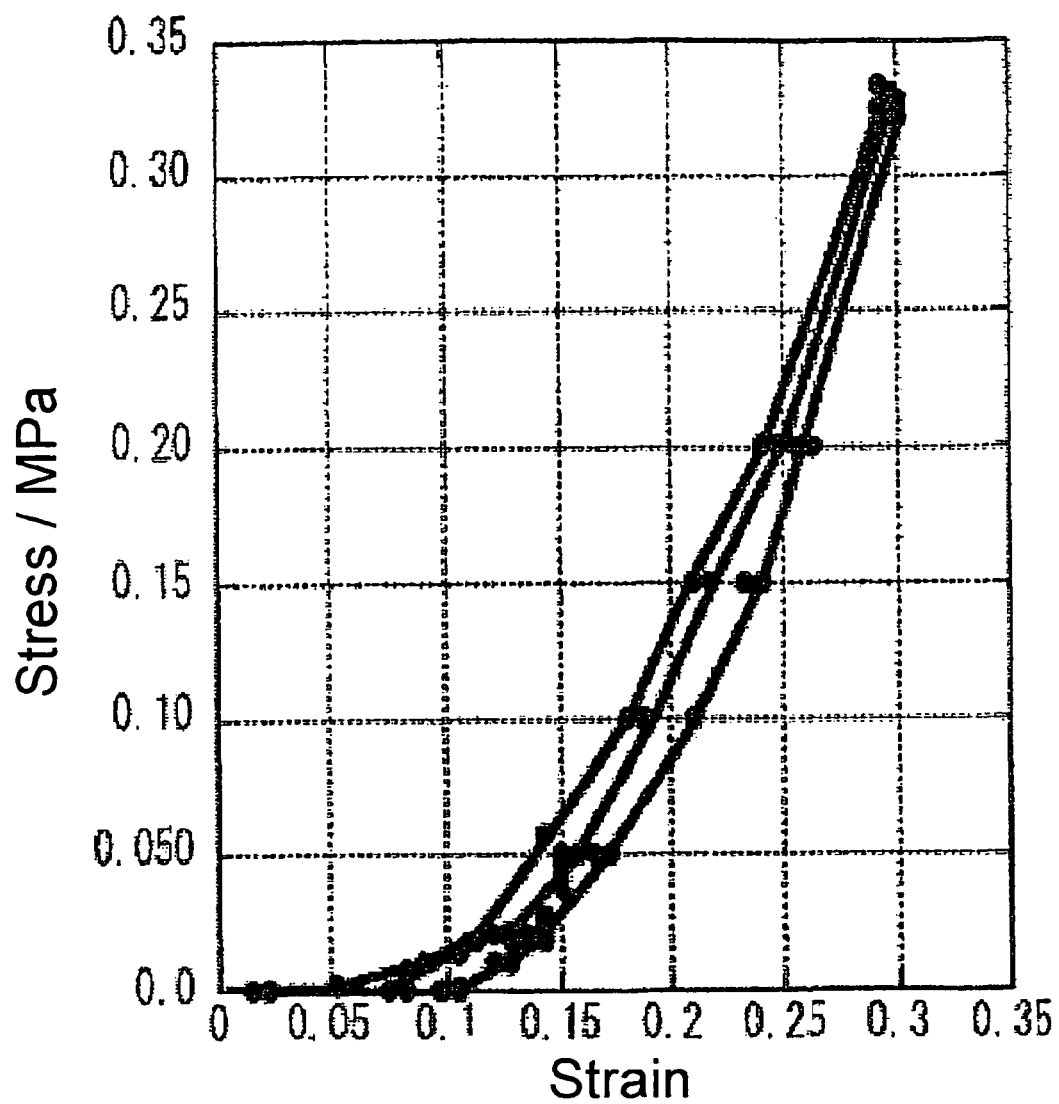

[Fig. 30]
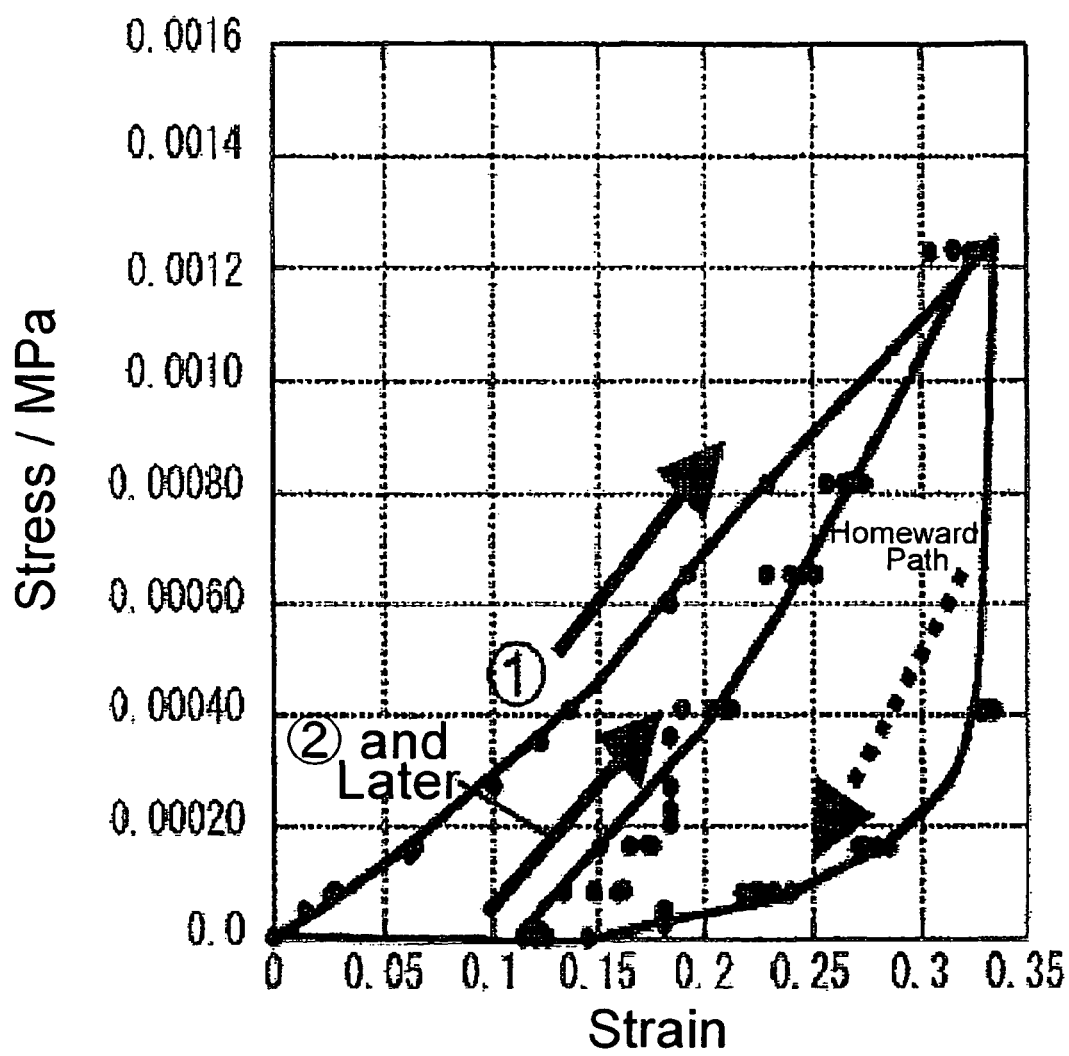

[Fig. 31]
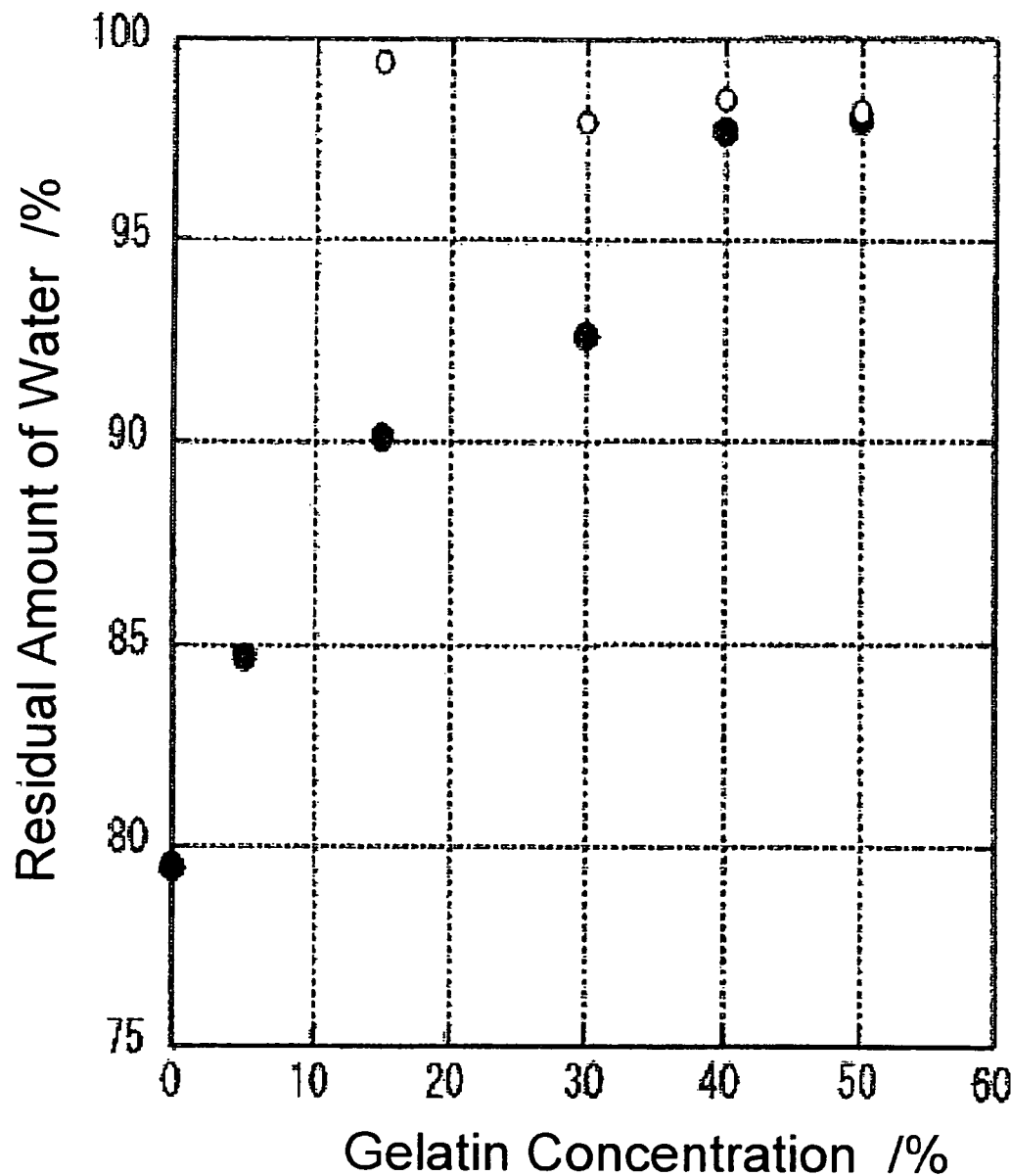

[Fig. 32]
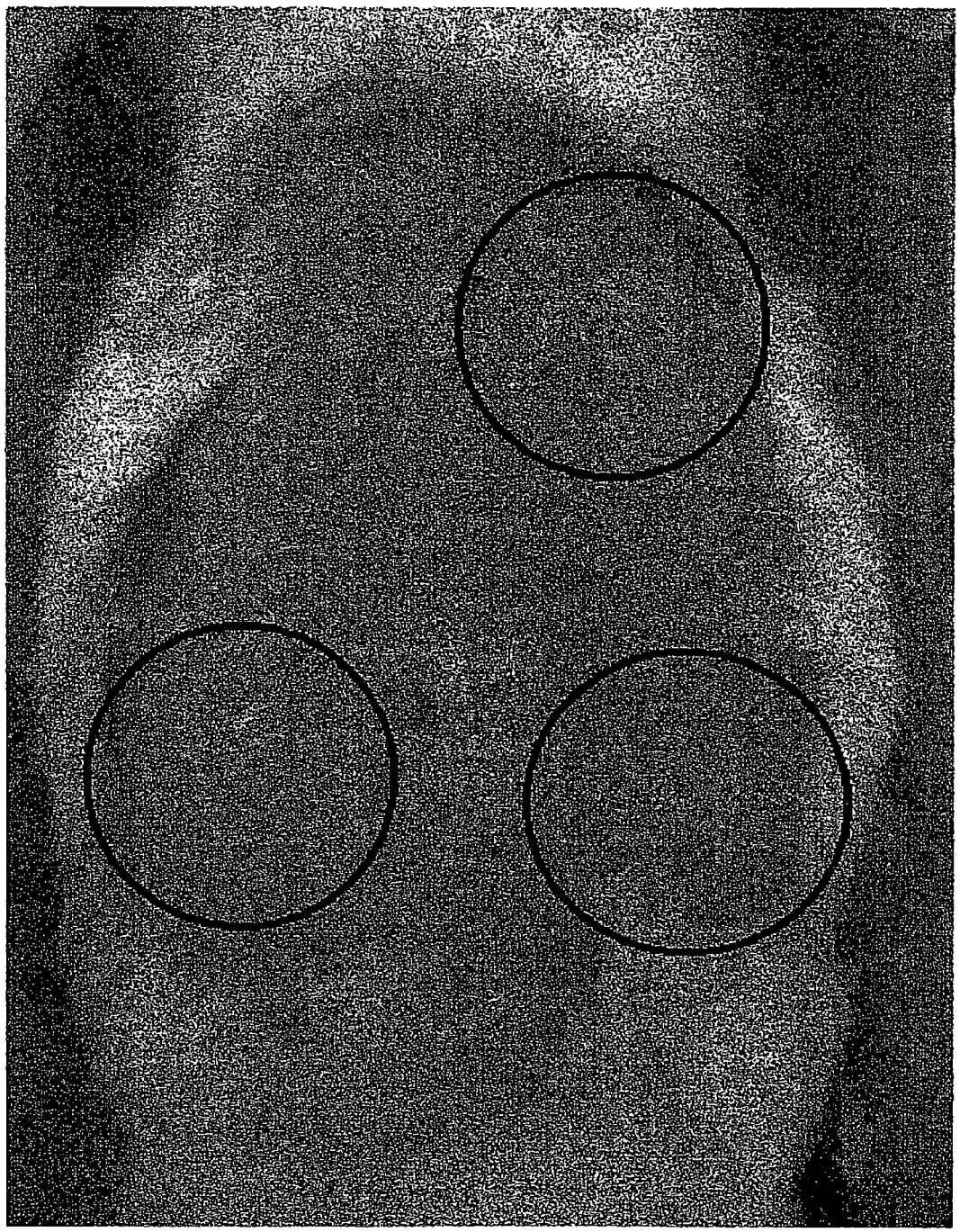

[Fig. 33]
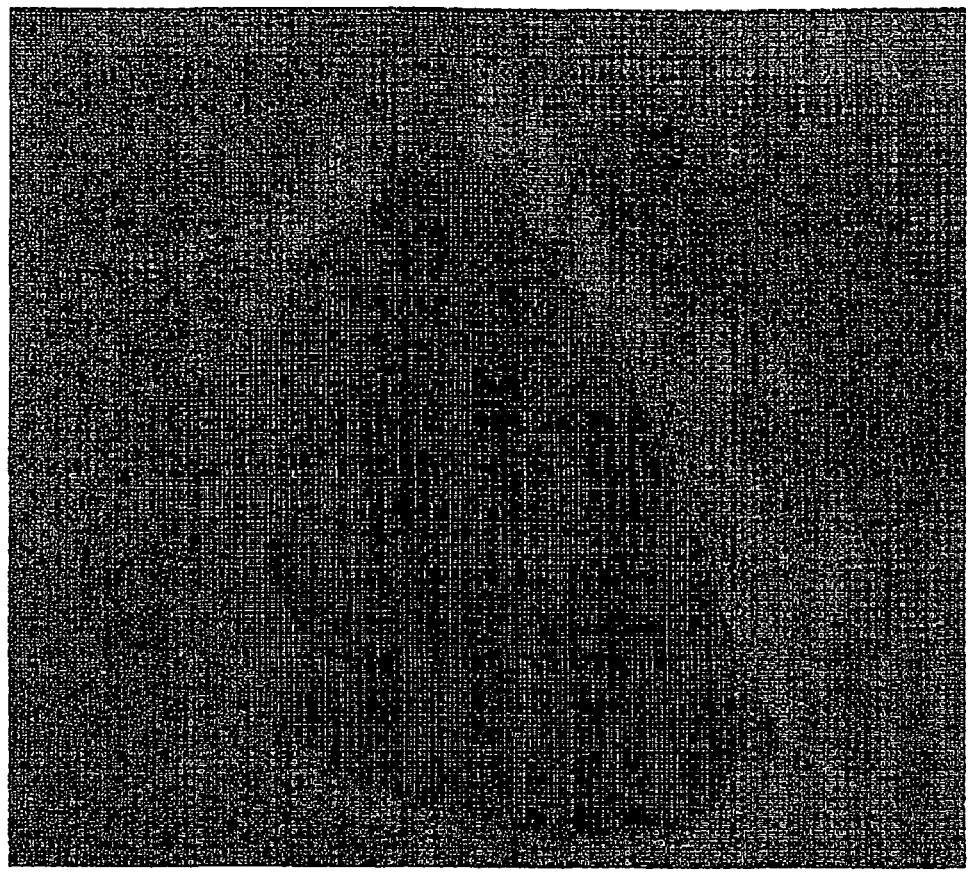
(1)
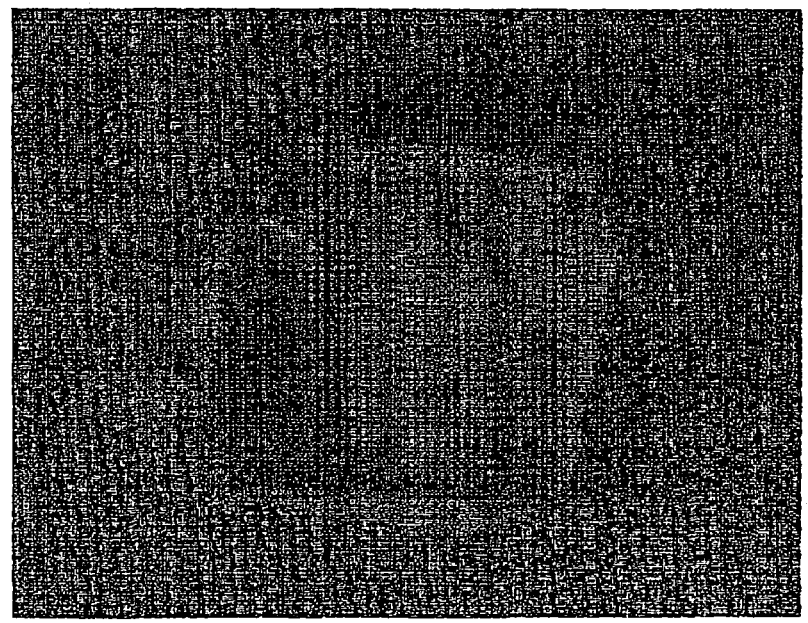
(2)

[Fig. 34]
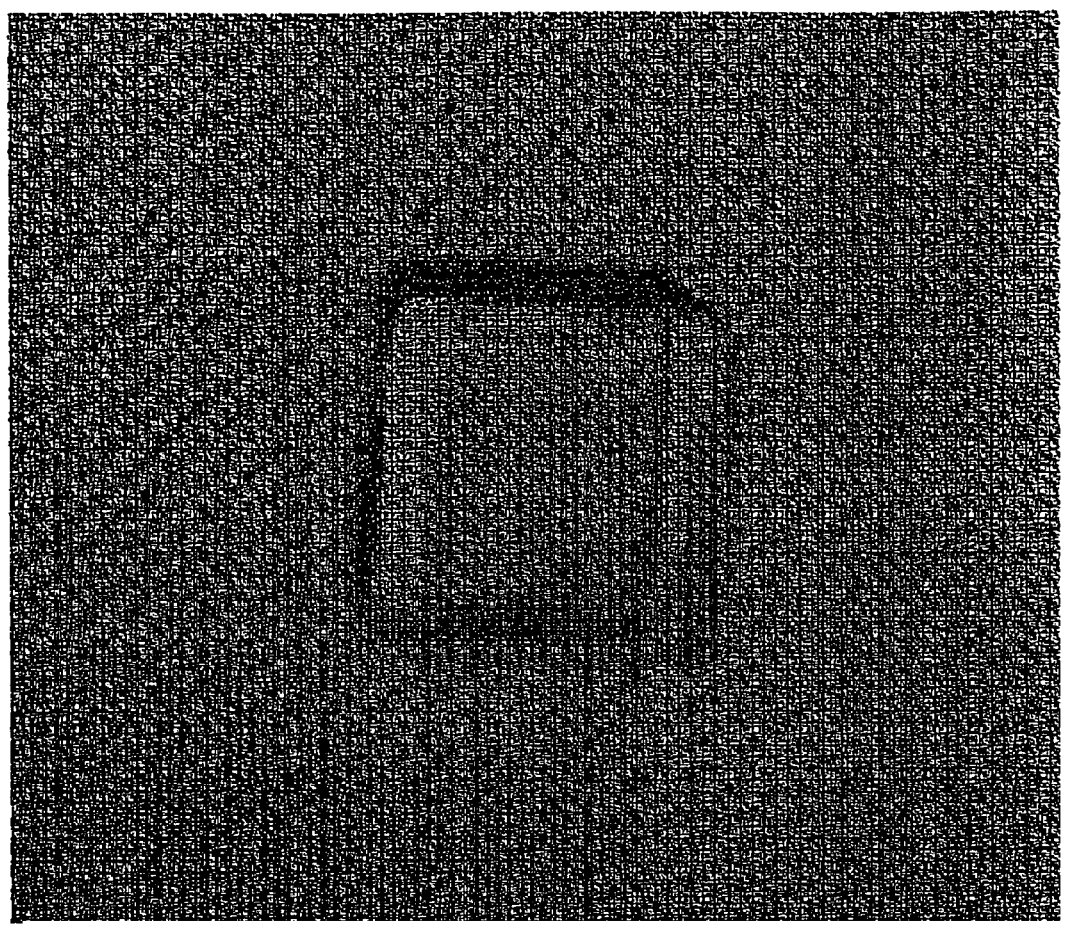

[Fig. 35]
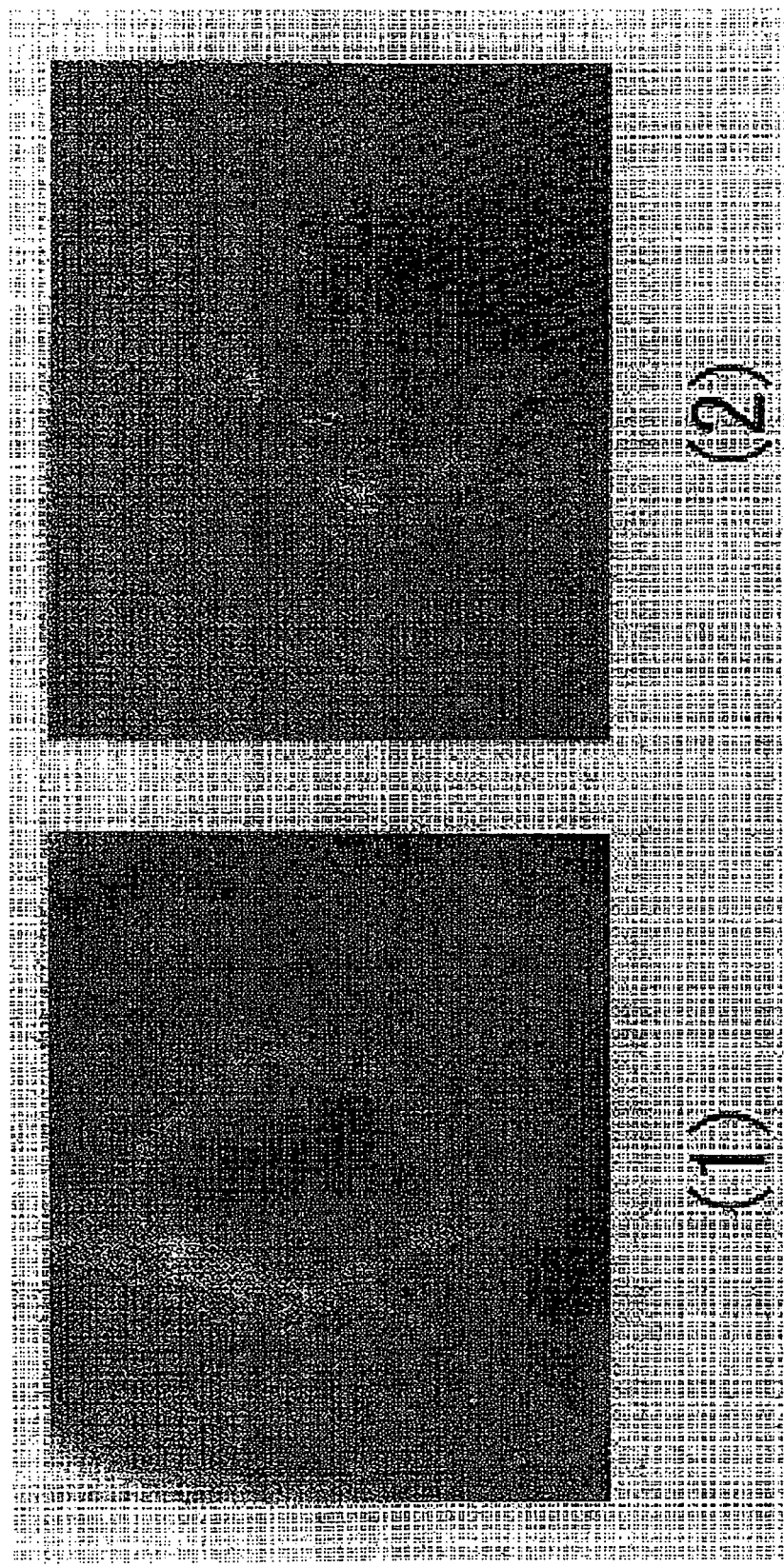

[Fig. 36]
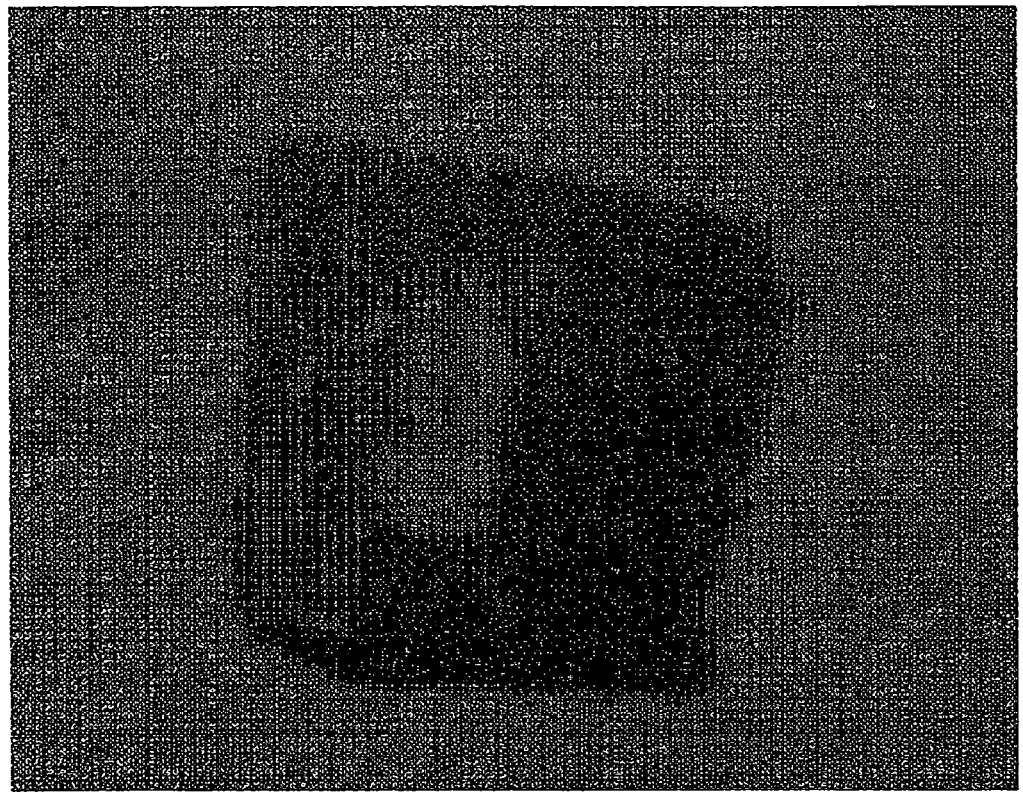
[Fig. 37]

[Fig. 38]
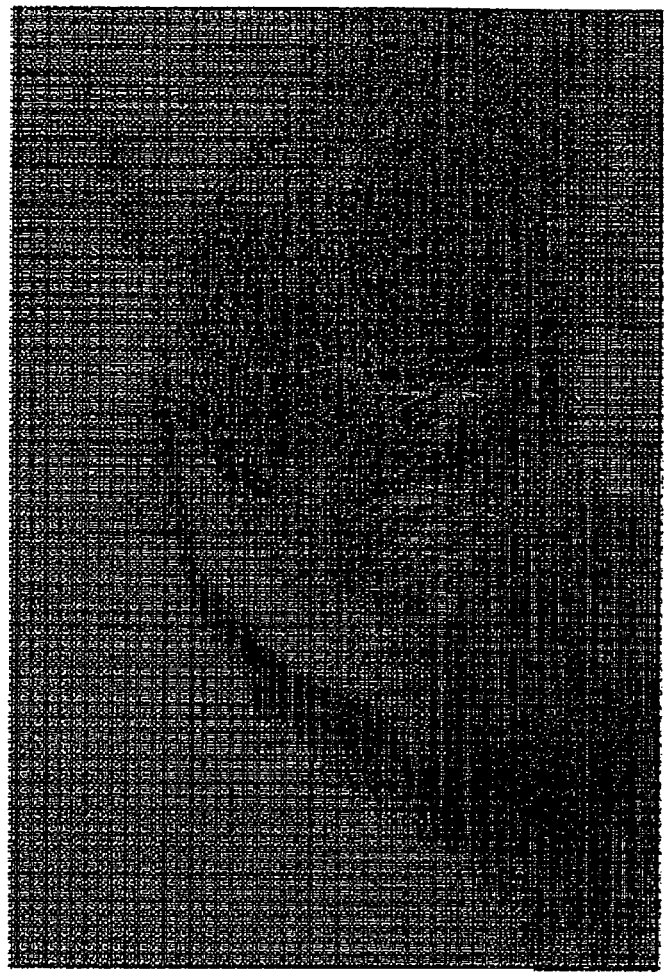
(2)
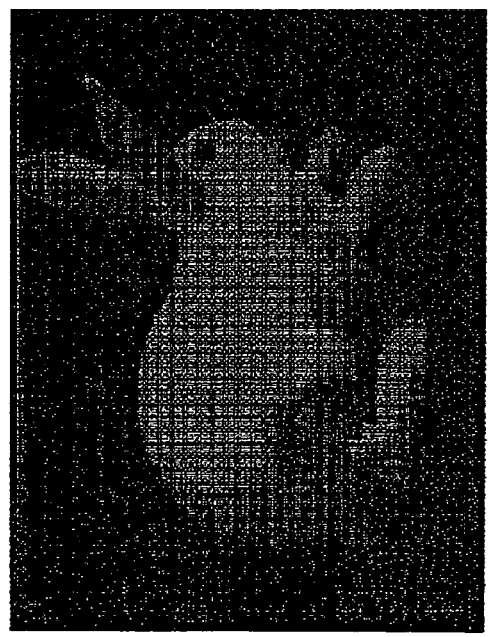
(1)

[Fig. 39]
(1)
(2)

[Fig. 40]
(1)
(2)

[Fig. 41]
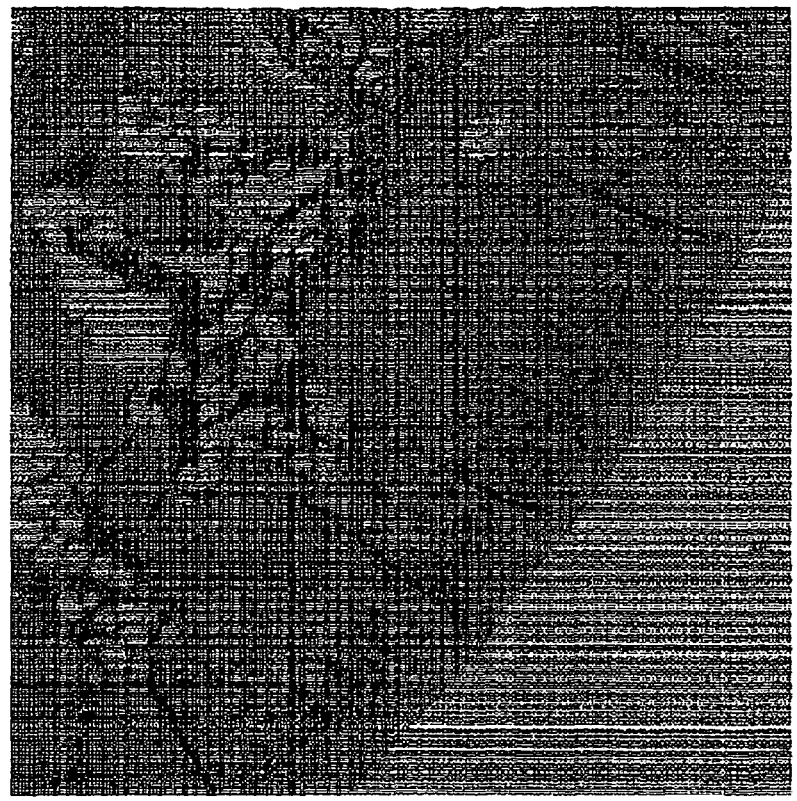
(1)
(2)

[Fig. 42]
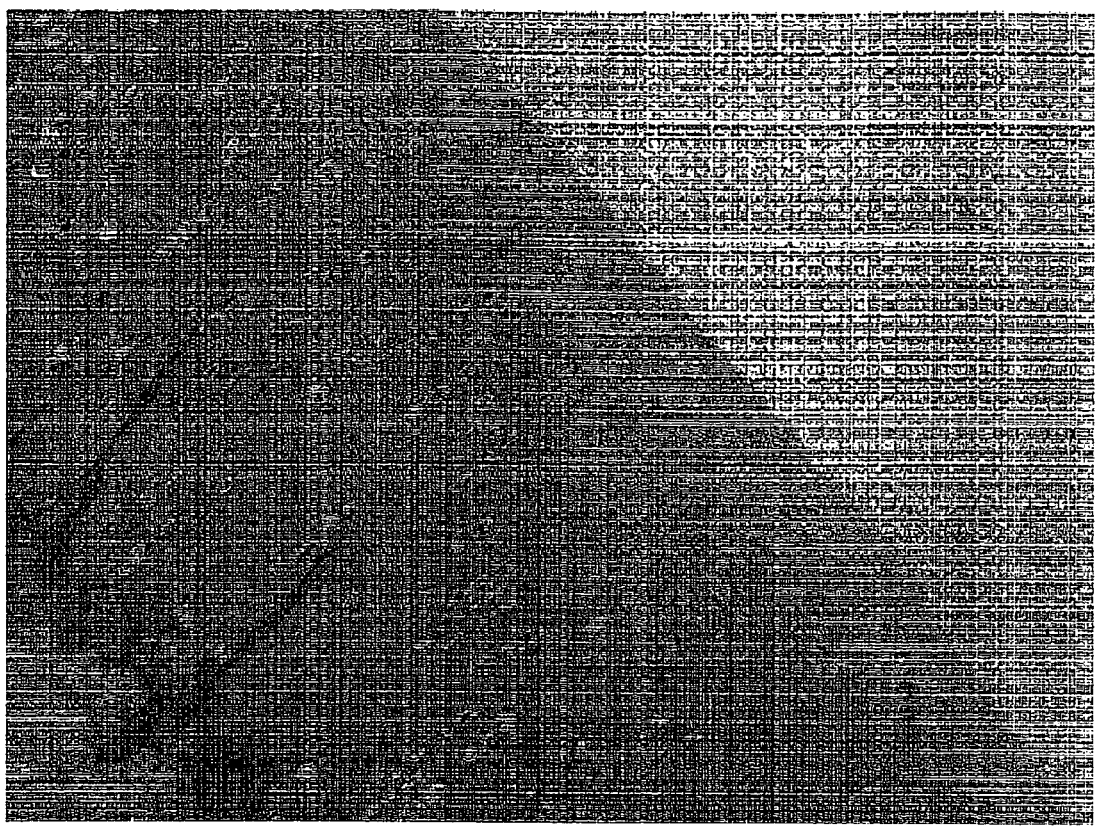

[Fig. 43]
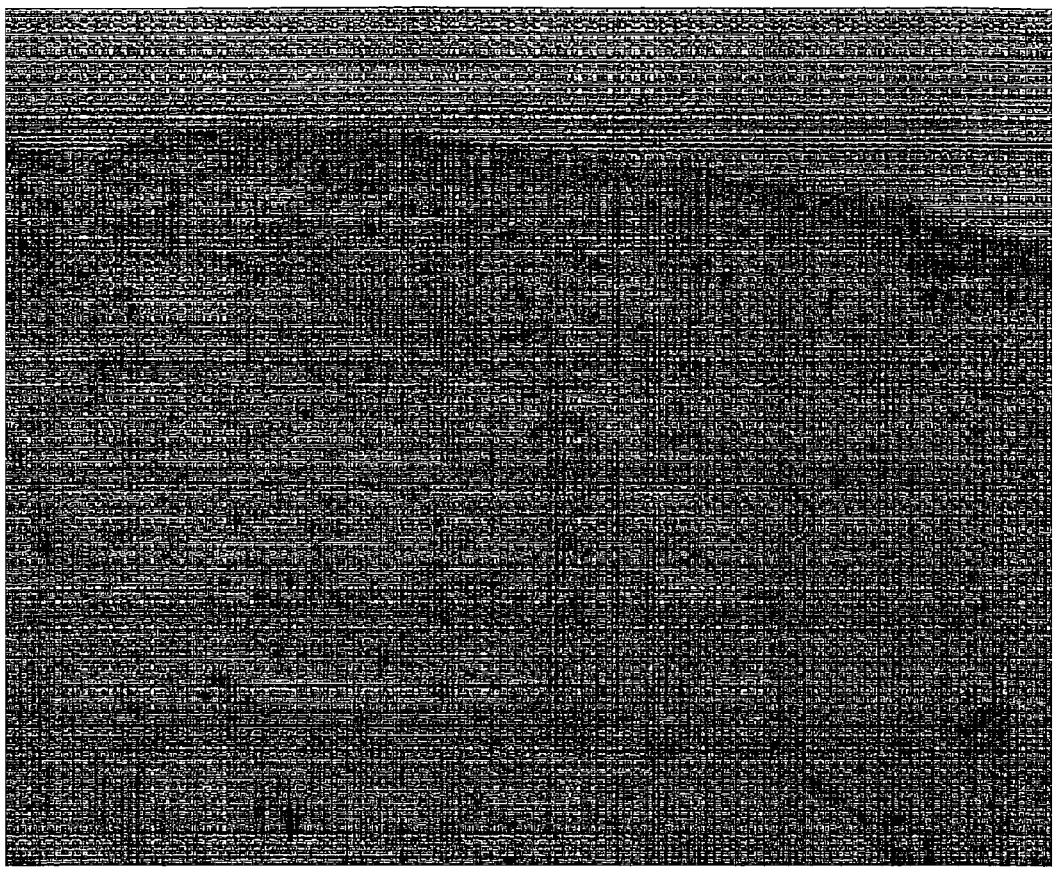

ARTIFICIAL MENISCUS AND PROCESS OF MAKING THEREOF

This application is a U.S. National Phase Application under 35 USC 371 of International Application PCT/JP004/008599, filed Jun. 18, 2004, which is incorporated herein in its entirety by this reference.

TECHNICAL FIELD

The present invention relates to artificial menisci which, even if positioned for an extended period of time between the joints under the severest mechanical environment in an organism, can maintain moderate mechanical strength and have no risk of developing any osteoarthritis.

BACKGROUND ART

Knee joints are required to have functionalities under the severest mechanical environment rather than characteristics of the surface shape of the joints and the degree of freedom for joint motions. Important functions such as load transmission and shock absorption are assumed by a meniscus.

The meniscus exists between the femur and the tibia to assume the action of dispersing the load applied from the femur for absorbing shocks and the role of providing stability and smooth motions of the knee joint. The meniscus is formed of fibrocartilage and collagen and is supplied with blood circulation from the surrounding joint capsules and with nutrients from synovial fluid.

For the treatment of meniscal disorders involving damages to or degeneration of the menisci, restoration of its mechanical functionalities is important. Conservative treatments (such as casting and bracing) or surgical treatments (such as suture and excision) are performed on restorable disorders, while, for unrestorable disorders, since the meniscus may not be regenerated, allogenic meniscal implantation as reported in Europe and the United States and regeneration medicine recently attracting attention (meniscus regeneration measures for regenerating the meniscus by the use of cultured cells from the meniscus to fill it) have been suggested. However, for meniscal implantation, it is highly difficult to obtain menisci in our country and, also for regeneration medicine, it has not yet been put into practical use as of this moment and is expected to require a great deal of time and cost to reach regeneration.

As such, the advent of artificial menisci is much anticipated. As described above, however, since between the joints is where the severest mechanical environment is found in an organism, materials capable of withstanding such severe environment do not exist at the moment. In addition, moderate mechanical properties for an extended period of time must be maintained for application in an organism for an extended period of time and also any osteoarthritis must not be induced. Therefore, the present invention aims to provide, primarily, actually usable, artificial menisci for the first time and, secondarily, artificial menisci which, when applied for an extended period of time in an organism, can maintain moderate mechanical properties for an extended period of time and will not induce any osteoarthritis.

DISCLOSURE OF THE INVENTION

Means for Solving the Problems

The present invention (1) is an artificial meniscus, a base material of which is a hydrogel having a semi-interpenetrating network structure or an interpenetrating network structure.

The present invention (2) is the artificial meniscus according to the invention (1) wherein a linear polymer or a network structure composing the hydrogel is a polymer of an electrically charged unsaturated monomer and/or an electrically neutral unsaturated monomer or a crosslinked product thereof or/and a naturally occurring polymer or a crosslinked product thereof.

The present invention (3) is the artificial meniscus according to the invention (2) wherein the electrically charged unsaturated monomer is an unsaturated monomer having an acidic group and/or a basic group.

The present invention (4) is the artificial meniscus according to the invention (3) wherein the acidic group is a carboxyl group, a phosphate group or a sulfonic group or a salt thereof.

The present invention (5) is the artificial meniscus according to the invention (3) wherein the unsaturated monomer having an acidic group is 2-acrylamido-2-methylpropane sulfonic acid, acrylic acid, methacrylic acid or a salt thereof.

The present invention (6) is the artificial meniscus according to any one of the inventions (2) to (5) wherein the electrically neutral unsaturated monomer is acrylamide, N-isopropyl acrylamide, N,N-dimethyl-acrylamide, vinylpyridine, styrene, methyl methacrylate, a fluorine-containing unsaturated monomer (for example, trifluoroethyl acrylate), hydroxyethyl acrylate or vinyl acetate.

The present invention (7) is the artificial meniscus according to any one of the inventions (1) to (6) wherein the hydrogel contains a metal ion, and a linear polymer or a network structure composing the hydrogel has a group capable of forming a complex with the metal ion.

The present invention (8) is the artificial meniscus according to any one of the inventions (2) to (7) wherein the naturally occurring polymer is bacterial cellulose or an electrically charged, naturally occurring polymer.

The present invention (9) is the artificial meniscus according to the invention (8) wherein the electrically charged, naturally occurring polymer is selected from the group consisting of gelatin, collagen, sodium alginate, gellan gum, carrageenan, chitosan, hyaluronic acid, proteoglycan and aggrecan as well as any combination thereof.

The present invention (10) is the artificial meniscus according to the invention (1) wherein the hydrogel is composed of a network structure having 2-acrylamido-2-methylpropane sulfonic acid as a material monomer and a network structure having acrylamide as a material, of a network structure consisting of bacterial cellulose and a network structure having N,N-dimethyl-acrylamide as a material monomer, or of a network structure consisting of bacterial cellulose and a network structure consisting of gelatin.

The present invention (11) is a process for producing an artificial meniscus based on a hydrogel having a semi-interpenetrating network structure or an interpenetrating network structure wherein a linear polymer or a network structure composing the hydrogel is a polymer of an electrically charged unsaturated monomer and/or an electrically neutral unsaturated monomer or a crosslinked product thereof, comprising a first step of polymerizing and crosslinking a first monomer component, of which 10 mol % or more is an electrically charged unsaturated monomer, in the presence of a solvent, to thereby form a first network structure; and a second step of introducing a second monomer component, of which 60 mol % or more is an electrically neutral unsaturated monomer, into the first network structure and then polymerizing the second monomer component in the presence of a solvent to thereby form a polymer in the first network structure; or optionally, further crosslinking the polymer to thereby form a second network structure in the first network structure, wherein in the case of the second monomer component being polymerized and crosslinked, the degree of crosslinking is set to be lower than the degree of crosslinking when the first monomer component is polymerized and crosslinked and wherein the molar ratio in amount of the first monomer component to the second monomer component is from 1:2 to 1:100.

The present invention (12) is the process according to the invention (11) wherein a crosslinker is used in an amount of 0.1 to 50 mol % to the first monomer component and a crosslinker is used in an amount of 0.001 to 20 mol % to the second monomer component.

The present invention (13) is the process according to the invention (11) or (12) wherein the polymerization and/or crosslinking in the first step and/or the second step are carried out in an aqueous solution.

The present invention (14) is a process for producing an artificial meniscus based on a hydrogel having a semi-interpenetrating network structure or an interpenetrating network structure wherein the network structure comprises a network structure of bacterial cellulose, comprising a step of culturing bacteria in a medium containing a polymer of an electrically charged unsaturated monomer and/or an electrically neutral unsaturated monomer or a crosslinked product thereof or a naturally occurring polymer or a crosslinked product thereof to thereby produce bacterial cellulose; and a step of introducing an electrically charged unsaturated monomer and/or an electrically neutral unsaturated monomer into the bacterial cellulose and then polymerizing the monomer component in the presence of a solvent to thereby form a polymer in a first network structure; or optionally, further crosslinking the polymer to thereby form a network structure also in the bacterial cellulose, or a step of impregnating the bacterial cellulose in a solution containing an electrically charged, naturally occurring polymer to incorporate the electrically charged, naturally occurring polymer into the bacterial cellulose.

EFFECT OF THE INVENTION

The artificial meniscus according to the present invention, when applied for an extended period of time in an organism, can maintain moderate mechanical properties for an extended period of time and will not induce any osteoarthritis. Therefore, the artificial meniscus according to the present invention is useful as prostheses for lost menisci and can prevent osteoarthritis induced by an extended period of having the meniscus lost and, when osteoarthritis have already developed, is expected to alleviate or cure the symptoms. While it is unclear why the artificial meniscus according to the present invention shows the effects comparable to the natural meniscus for an extended period of time, the artificial meniscus according to the present invention is estimated to possess one or any combination or all of the functionalities required for the meniscus: 1) shock absorption of the articular cartilages, 2) contribution to stabilization of the joints, 3) nutrient supply to the articular cartilages, 4) prosthesis of unmatched joints, and 5) assistance of lubrication.

BRIEF DESCRIPTION OF THE DRAWINGS

FIG. 1 shows a water-absorbing resin having an interpenetrating network structure (double network type) in which a network structure formed by polymerizing and crosslinking a first monomer component (first network structure) and another network structure formed by polymerizing and crosslinking a second monomer component (second network structure) are physically entwined with each other through their networks wherein A denotes the first network structure, B denotes the second network structure, and 1 and 2 denote crosslinking points;

FIG. 2 shows a water-absorbing resin having an semi-interpenetrating network structure in which a first network structure and a linear polymer formed by polymerizing a second monomer component are physically entwined with each other through their networks (double network type) wherein C denotes the first network structure, D denotes the linear polymer and 3 denotes a crosslinking point;

FIG. 3 shows the dependency on concentration of a monomer composing the second network structure in relation to compression stress and strain at rupture in a 1PAMPS4-XPAAm0.1 DN gel, wherein the second monomer concentration along the horizontal axis refers to the concentration of the second monomer used for polymerization, to which X in "1PAMPS-XPAAm0.1" corresponds;

FIG. 4 shows the dependency on degree of crosslinking of the second network structure in relation to compression stress at rupture in a 1PAMPS4-1PAAmX DN gel;

FIG. 5 shows an experimental system for taking pictures of photoelastic images as a gel is deformed under stress, wherein 4 denotes a light source, 5 denotes a polarizer, 6 and 8 denote ¼ plates, 7 denotes a specimen, 9 denotes an analyzer, 10 denotes a CCD camera and 11 denotes a computer;

FIG. 6 shows photoelastic images representing stress dispersion for various gels as the gels are deformed under stress, wherein (a) is of 1PAMPS4-1 PAAm0.1 DN gel and (b) is of 1PAMPS4-1PAAm2 DN gel;

FIG. 7 shows the relationship between normalized power (longitudinal axis) and strain (%) as 1PAMS4-1PAAmX DN gels (X=0, 0.1, 0.5, 1.0 and 2.0 mol %) are deformed under stress, wherein "□" is for X=0 mol %, "x" is for X=0.1 mol %, "∇" is for X=0.5 mol %, "◇" is for X=1.0 mol % and "○" is for X=2.0 mol %;

FIG. 8 shows the relationship between normalized power (longitudinal axis) and degree of crosslinking (mol %) as 1PAMPS4-1PAAmX DN gels (X=0, 0.1, 0.5, 1 and 2 mol %) are deformed under stress, wherein "□" is for strain of 6.670%, "∇" is for strain of 13.33%, "◇" is for strain of 20.00% and "○" is for strain of 26.67%;

FIG. 9 shows the relationship between intensity (longitudinal axis) and strain (%) as various 1PAMPS4-XPAAm0.1 DN gels having different AAm concentrations are deformed under stress, wherein "☆" is for X=0.5 M, "x" is for X=1 M, "∇" is for X=2 M, "◇" is for X=3 M and "○" is for X=5 M;

FIG. 10 shows a tensile stress vs. strain curve of BC hydrogels of Examples 7, 8 (gelatin) and Comparative Example 1, as obtained in accordance with Test Example 3, wherein (1) is from Comparative Example 1, (2) is from Example 7 and (3) is from Example 8 (lines (2) and (3) are shown as one since they are almost overlapped);

FIG. 11 shows a tensile stress vs. strain curve of BC hydrogels of Example 9 (sodium alginate) and Comparative Example 2, as obtained in accordance with Test Example 4, wherein (1) is from Comparative Example 2 and (2) is from Example 9;

FIG. 12 shows a tensile stress vs. strain curve of BC hydrogels of Example 10 (gellan) and Comparative Example 2, as obtained in accordance with Test Example 4, wherein (1) is from Comparative Example 2 and (2) is from Example 10;

FIG. 13 shows a tensile stress vs. strain curve of BC hydrogels of Example 11 (gelatin), Example 12 (crosslinked gelatin) and a commercially available BC, as obtained in accordance with Test Example 5 wherein (1) is from the commercially available BC, (2) is from Example 11 and (3) is from Example 12;

FIG. 14 shows a compressive stress vs. strain curve of BC hydrogels of Example 13 (crosslinked gelatin) and Comparative Example 3, as obtained in accordance with Test Example 6, wherein (1) is from Comparative Example 3 and (2) is from Example 13;

FIG. 15 shows a compressive stress vs. strain curve of BC hydrogels of Example 14 (sodium alginate) and Comparative Example 3, as obtained in accordance with Test Example 6, wherein (1) is from Comparative Example 3 and (2) is from Example 14;

FIG. 16 shows a compressive stress vs. strain curve of BC hydrogels of Example 15 (ι-carrageenan) and Comparative Example 3, as obtained in accordance with Test Example 6, wherein (1) is from Comparative Example 3 and (2) is from Example 15;

FIG. 17 shows a compressive stress vs. strain curve of BC hydrogels of Example 16 (gellan gum) and Comparative Example 3, wherein (1) is from Comparative Example 3 and (2) is from Example 16;

FIG. 18 shows a tensile stress vs. strain curve of BC hydrogels of Example 13 (crosslinked gelatin) and Comparative Example 3, as obtained in accordance with Test Example 6, wherein (1) is from Comparative Example 3 and (2) is from Example 13;

FIG. 19 shows a tensile stress vs. strain curve of BC hydrogels of Example 15 (sodium alginate) and Comparative Example 3, as obtained in accordance with Test Example 6, wherein (1) is from Comparative Example 3 and (2) is from Example 15;

FIG. 20 shows a tensile stress vs. strain curve of BC hydrogels of Example 15 (ι-carrageenan) and Comparative Example 3, as obtained in accordance with Test Example 6, wherein (1) is from Comparative Example 3 and (2) is from Example 15;

FIG. 21 shows a tensile stress vs. strain curve of BC hydrogels of Example 16 (gellan gum) and Comparative Example 3, wherein (1) is from Comparative Example 3 and (2) is from Example 16;

FIG. 22 shows a compressive stress vs. strain curve of BC hydrogels of Examples 17 and 18 (crosslinked gelatin) different in EDC concentration, and Comparative Example 4, as obtained in accordance with Test Example 7, wherein (1) is from Comparative Example 4, (2) is from Example 17 and (3) is from Example 18;

FIG. 23 shows a tensile stress vs. strain curve of BC hydrogels of Examples 17 and 18 (crosslinked gelatin) different in EDC concentration and Comparative Example 4, as obtained in accordance with Test Example 7, wherein (1) is from Comparative Example 4, (2) is from Example 17 and (3) is from Example 18;

FIG. 24 shows a compressive stress vs. strain curve of BC hydrogels of Examples 19 to 22 (crosslinked gelatin) different in gelatin concentration and Comparative Example 4, as obtained in accordance with Test Example 7, wherein (1) is from Comparative Example 4, (2) is from Example 19, (3) is from Example 20, (4) is from Example 21 and (5) is from Example 22;

FIG. 25 shows a tensile stress vs. strain curve of BC hydrogels of Examples 19 to 22 (crosslinked gelatin) different in gelatin concentration and Comparative Example 4, as obtained in accordance with Test Example 7, wherein (1) is from Comparative Example 4, (2) is from Example 19, (3) is from Example 20, (4) is from Example 21 and (5) is from Example 22;

FIG. 26 shows a compressive stress vs. strain curve of a BC/gelatin DN gel with an aqueous NaCl solution as the solvent in the gel, wherein (1) is with 0 M aqueous NaCl solution, (2) is with 0.001 M aqueous NaCl solution, (3) is with 0.01 M aqueous NaCl solution and (4) is with 0.1 M aqueous NaCl solution;

FIG. 27 shows a tensile stress vs. strain curve of a BC/gelatin DN gel with an aqueous NaCl solution as the solvent in the gel, wherein (1) is with 0 M aqueous NaCl solution, (2) is with 0.001 M aqueous NaCl solution, (3) is with 0.01 M aqueous NaCl solution and (4) is with 0.1 M aqueous NaCl solution;

FIG. 28 shows the results of cycle tests on a BC/gelatin (50) DN hydrogel;

FIG. 29 shows the results of cycle tests on a gelatin (50) hydrogel;

FIG. 30 shows the results of cycle tests on a BC hydrogel;

FIG. 31 shows the residual amounts of water in relation to gelatin concentrations, wherein ○ denotes the case with gelatin alone and ● denotes the case with BC/gelatin DN hydrogel;

FIG. 32 shows an electrophotograph of the dorsal area after subcutaneous implantation experiment of a DN gel of PAMPS-PDMAA;

FIG. 33 (1) and (2) each show an electrophotograph of the surroundings of the subcutaneous DN gel of PAMPS-PDMAA after the subcutaneous implantation experiment;

FIG. 34 shows an electrophotograph of the DN gel of PAMPS-PDMAA as taken out after the experimental subcutaneous implantation;

FIGS. 35 (1) and (2) each show an electrophotograph of the surroundings of a BC/gelatin DN hydrogel after the subcutaneous implantation experiment;

FIG. 36 shows an electrophotograph of the BC/gelatin DN hydrogel as taken out after the subcutaneous implantation experiment;

FIG. 37 shows an electrophotograph of the dorsal area after subcutaneous implantation experiment of a DN gel of BC/PDMAA;

FIG. 38 (1) shows an electrophotograph of whole body of a female rabbit just before it was sacrificed in an in vivo implantation experiment and FIG. 38 (2) shows an electrophotograph of the animal around the knee joint;

FIG. 39 (1) shows an electrophotograph of an artificial meniscus during operation for in vivo implantation experiment and FIG. 39 (2) shows an electrophotograph of the artificial meniscus just before extraction (four weeks after implantation);

FIG. 40 (1) shows an electrophotograph of an artificial meniscus before in vivo implantation experiment and FIG. 40 (2) shows an electrophotograph of the artificial meniscus after the experiment;

FIG. 41 shows photographs of the femur cartilage after in vivo implantation experiment, stained with (1) HE and (2) safranin O;

FIG. 42 shows a photograph of the tibial cartilage stained with safranin O after in vivo implantation experiment; and FIG. 43 shows a photograph of the synovia stained with HE after in vivo implantation experiment.

BEST MODE FOR CARRYING OUT THE INVENTION

First of all, technical terms as used herein will be defined with respect to their meanings. The term "first network structure" refers to a network structure formed first during production while the term "second network structure" refers to a network structure formed after the first network structure was formed, and the term "first monomer component" refers to a material for the first network structure while the term "second monomer component" refers to a material for the second network structure (in the case of an interpenetrating network structure) or a linear polymer (in the case of a semi-interpenetrating network structure). The term "degree of crosslinking" refers to a ratio of the mol concentration of a crosslinker to the mol concentration of a charged monomer, which is expressed in percentage. In reality, a slight amount of monomer may not be involved in polymerization or a slight amount of crosslinker may not be involved in crosslinking; in such cases, however, the degree of crosslinking herein is to be defined as above. The term "water-insoluble monomer" refers to a monomer such that when introduced in an amount of 1 g into 100 ml of water at normal temperature and pressure, 0.1 g or less of it will dissolve. Also, the term "water-soluble monomer" refers to a monomer which shows a value higher than the above at a normal temperature and pressure. The term "degree of swelling" (q) refers to a value given by the formula:

degree of swelling=weight of swollen gel ($W_W$)/ weight of dry gel ($W_D$).

The term "initial elastic modulus" refers to a value as given by the slope of a compressive (tensile) stress vs. compressive (tensile) strain curve with the compressive (tensile) strain ranging from 0 to 5%. "Compression stress at rupture" is calculated by the formula (force at rupture under compression/original cross sectional area) and "compression strain at rupture" is calculated by the formula (original length−length at rupture under compression)/original length×100%. "Tensile stress at rupture" is calculated by the formula (force at rupture under tension/original cross sectional area) and "tensile strain at rupture" is calculated by the formula (length at rupture under tension−original length)/original length×100%. The term "meniscus" is not limited to the meniscus in a narrow sense (a meniscal-shaped body existing in an organism) but includes any shapes insertable between the articular cartilages, that can function as the menisci.

The present invention relates to an artificial meniscus which is based on a hydrogel having an interpenetrating network structure or a semi-interpenetrating network structure. Constituent features of the present invention will be described below.

"An interpenetrating network structure" refers to a condition in which a network structure as a base is uniformly entwined with another network structure throughout the structure, with a result that multiple network structures are formed inside. For example, as shown in FIG. 1, a resin of such a kind is composed of a first network structure A having multiple crosslinking points 1 and a second network structure B having multiple crosslinking points 2, these first and second network structures A and B being physically entwined with each other through their networks. This figure is a concept drawing of a gel obtained as a result of water absorption by a water-absorbing resin, which contains a solvent (water) in network structures.

"A semi-interpenetrating network structure" refers to a condition in which a network structure as a base is uniformly entwined with a linear polymer throughout the structure, with a result that multiple network structures are formed within the structure. For example, as shown in FIG. 2, a resin of such a kind is composed of a first network structure C having multiple crosslinking points 3 and a linear polymer D, the first network structure C and the linear polymer D being physically entwined with each other through their networks.

In FIGS. 1 and 2, the first network structures A and C are drawn in bolder lines than the second network structure B and the linear polymer D, but only for convenience. In addition, "an interpenetrating network structure" and "a semi-interpenetrating network structure" conceptually encompass gels, not only of the double network type, but also of a triple, quadruple or more network type.

A linear polymer or a network structure composing a semi-interpenetrating network structure or an interpenetrating network structure is preferably a polymer of an electrically charged unsaturated monomer and/or an electrically neutral unsaturated monomer or a crosslinked product thereof or/and a naturally occurring polymer or a crosslinked product thereof. As preferable materials for producing artificial menisci according to the present invention, electrically charged unsaturated monomers, electrically neutral unsaturated monomers and naturally occurring polymers will first be described below.

As an electrically charged unsaturated monomer, an unsaturated monomer having an acidic group (for example, a carboxyl group, a phosphate group and a sulfonic group) and/or a basic group (for example, an amino group), such as 2-acrylamido-2-methylpropane sulfonic acid, acrylic acid, methacrylic acid or a salt thereof may preferably be mentioned.

As an electrically neutral unsaturated monomer, acrylamide, N-isopropyl acrylamide, N,N-dimethyl-acrylamide, vinylpyridine, styrene, methyl methacrylate, a fluorine-containing unsaturated monomer (for example, trifluoroethyl acrylate), hydroxyethyl acrylate or vinyl acetate may be mentioned for example.

As a naturally occurring polymer, bacterial cellulose or an electrically charged, naturally occurring polymer may be mentioned for example. "Bacterial cellulose" (sometimes abbreviated below as BC) here means any one or mixture of a cellulose, a heteropolysaccharide having a cellulose as main chain and a glucan, such as β-1,3- or β-1,2-glucan, as produced by a microorganism. For a heteropolysaccharide, components other than celluloses are hexoses, pentoses and organic acids, such as mannose, fructose, galactose, xylose, arabinose, rhamnose and glucuronic acid. Microorganisms for producing bacterial cellulose are not particularly limited and those capable of producing bacterial cellulose, such as *Gluconacetobacter xylinus* subsp. *xylinus* (*Yamada*) ATCC-53582, *Acetobactoraceti* subsp. *xylinum* ATCC-10821, *Acetobactoraceti* subsp. *pasteurium*, *Acetobactoraceti* subsp. *rancens*, *Sarcina ventriculi*, *Bacterium xyloides*, *Pseudomonas* bacteria and *Agrobacterium* bacteria are available. In addition, "an electrically charged, naturally occurring polymer" denotes a protein or polysaccharide having an electric charge. Specifically, gelatin and collagen may be mentioned as proteins and sodium alginate, gellan gum, carrageenan, chitosan and hyaluronic acid may be mentioned as polysaccharides. It also encompasses glycoproteins, covalent compounds between saccharides and proteins, examples of which include proteoglycans and aggrecans.

Relationships between a first network structure and a second network structure (in the case of interpenetrating network structure) and between a first network structure and a linear polymer (in the case of semi-interpenetrating network structure) in the hydrogel will then be described with reference to each preferred embodiment.

First, description will be made on the case where a linear polymer or a network structure composing a semi-interpenetrating network structure or an interpenetrating network structure is a polymer of an electrically charged unsaturated monomer and/or an electrically neutral unsaturated monomer or a crosslinked product thereof (hereinafter referred to as "first preferred embodiment"). A first preferable feature of this embodiment lies in that 10 mol % or more of the first monomer component is an electrically charged unsaturated monomer, and 60 mol % or more of the second monomer component is an electrically neutral unsaturated monomer. In other words, by providing for this manner, it is made possible to introduce a large amount of electrically neutral unsaturated monomers into a first network structure (a network structure formed by polymerizing and crosslinking a first monomer component, in which an electrically charged group, for example, a carboxyl group, is present in a certain amount or more). In other words, the type and amount of the monomer to be used and the sequence of uses are of great importance.

The amount of the electrically charged unsaturated monomer in the first monomer component is 10 mol % or more, preferably 30 mol %, and most preferably, 100 mol % to the first monomer component. The amount of the electrically neutral unsaturated monomer in the second monomer component is 60 mol % or more, and preferably, 100 mol % to the second monomer component.

Further, a second feature of this preferred embodiment is that the molar ratio in amount of the first monomer component to the second monomer component in the hydrogel is from 1:2 to 1:100 (preferably 1:3 to 1:50, and more preferably, 1:3 to 1:30). By providing for this manner, it is made possible to provide the hydrogel with properties, such as mechanical strength, which have been unavailable heretofore. Introduction of an electrically neutral unsaturated monomer at such high ratios is made possible only by polymerizing and crosslinking the first monomer component to thereby form a network structure (first network structure) in which an electrically charged group (for example, a carboxylic group) is present in a certain amount or more, and then introducing the electrically neutral unsaturated monomer. When each network structure is composed of one monomer, the amount of the monomer in the gel is determined by elemental analysis. When each network structure is composed of two or more monomers, however, it may sometimes be too complex to be determined by elemental analysis. In such cases, the amount is given by subtracting the amount of monomer which was not polymerized from the amount of monomer which was used for the production.

Further, a third preferable feature of this embodiment is that when the second monomer component is polymerized and crosslinked, the degree of crosslinking is set to be lower than the degree of crosslinking when the first monomer component is polymerized and crosslinked. In other words, the degree of crosslinking of a second network structure (a network structure formed by polymerizing and crosslinking the second monomer component) is made lower than that of the first network structure, an extreme exemplification of which is the form of a hydrogel having a semi-interpenetrating network structure in which the degree of crosslinking of the second network structure is zero (that is, the second monomer component is polymerized, but not crosslinked). By providing for this manner, the gel can be provided with properties, such as mechanical strength, which have been unavailable heretofore. Conventionally, although gels in which the degree of crosslinking of a first network structure is lower than that of a second network structure have existed, such gels suffer from lack of mechanical strength. This embodiment is epoch-making in that the mechanical strength is greatly improved by merely reversing the relationship between the degrees of crosslinking of the first and second network structures.

Specifically, the amount of a crosslinker used for the formation of the first network structure and the amount of a crosslinker used for the formation of the second network structure are adjusted as appropriate in relation to the starting monomers for each network structure. Provision is made so that preferably the first network structure has a degree of crosslinking of 0.1 to 50 mol % and the second network structure has a degree of crosslinking of 0.001 to 20 mol %, more preferably the first network structure has a degree of crosslinking of 1 to 20 mol % and the second network structure has a degree of crosslinking of 0.01 to 5 mol %, and most preferably the first network structure has a degree of crosslinking of 2 to 10 mol % and the second network structure has a degree of crosslinking of 0.05 to 1 mol %. In particular, for lowering the water content of the gel (that is, to lower the degree of swelling) or for hardening the gel (that is, to increase the modulus of elasticity) the degrees of crosslinking for the both structures may be increased.

Now that the three preferable features of this embodiment have been discussed, other optional constituent features will then be described.

First, the first monomer component is not particularly limited as long as it contains 10 mol % or more of an electrically charged unsaturated monomer and, for example, an electrically neutral unsaturated monomer, which is essentially used as a second monomer component, may be used. Also, the second monomer component is not particularly limited as long as it contains 60 mol % or more of an electrically neutral unsaturated monomer and, for example, an electrically charged unsaturated monomer, which is essentially used as a first monomer component, may be used. Examples include 2-acrylamido-2-methylpropane sulfonic acid (AMPS), acrylamide (AAm), acrylic acid (AA), methacrylic acid, N-isopropyl acrylamide, vinylpyridine, hydroxyethyl acrylate, vinyl acetate, dimethyl siloxane, styrene (St), methyl methacrylate (MMA) and trifluoroethyl acrylate (TFE). In addition, polysaccharides, such as gellan, hyaluronic acid, carrageenan, chitin and alginic acid and proteins such as gelatin and collagen may be used. An organic monomer to be used may be identical or different among the first network structure, the second network structure (interpenetrating network structure) and the linear polymer (semi-interpenetrating network structure). When raw materials different from each other are used, hydrogels having higher mechanical properties will be obtained.

It is preferable to use, as organic monomers as raw materials, both water-insoluble monomers and water-soluble monomers. This is based on a novel finding that an excellent mechanical strength is provided when a water-insoluble monomer is partly used. Such a water-insoluble monomer may be used for the first network structure only, for the second network structure (interpenetrating network structure) or the linear polymer (semi-interpenetrating network structure) only or for the both. The ratio of the water-insoluble monomer to the water-soluble monomer is preferably 9.9:0.1 to 0.1:9.9. In particular, it is more preferable that the ratio of the water-soluble monomer to the water-insoluble monomer be 0:100 to 1:99 in the first network structure and 0:100 to 10:90 in the second network structure or the linear polymer. Moreover, it is even more preferable that the ratio of the water-soluble monomer to the water-insoluble monomer be 0:100 to 1:99 in the first network structure and 0:100 to 5:95 in the second network structure. In order to decrease the water content of the gel, the content of the hydrophobic monomer may be increased. Examples of water-insoluble monomers include fluorine-containing monomers, such as 2,2,2-trifluoroethyl methyl acrylate, 2,2,3,3,3-pentafluoropropyl methacrylate, 3-(perfluorobutyl)-2-hydroxypropyl methacrylate, 1H,1H, 9H-hexadecafluoronony methacrylate, 2,2,2-trifluoroethyl acrylate, 2,3,4,5,6-pentafluorostyrene and vinylidene fluoride.

Further, it is also preferable to use, as an organic monomer of a raw material, a monomer having a group capable of forming a complex with a metal ion and introduce a metal ion therefor into the gel to form a complex in the gel. In general, increasing the rate of complex formation in the gel, that is, the metal introduction ratio, tends to decrease the water content of the hydrogel and increase the mechanical strength of the hydrogel. In this case, the monomer having a group capable of forming a complex with a metal ion may be used for the first network structure only, for the second network structure (interpenetrating network structure) or the linear polymer (semi-interpenetrating network structure) only or for the both. A preferable embodiment is that a complex is formed with a metal ion in the first network structure. The metal content is preferably from 0.03 mol/l to 1 mol/l, and more preferably from 0.01 mol/l to 0.3 mol/l. The content of the monomer having a group capable of forming a complex is preferably from 10 to 100 mol %, and more preferably from 30 to 100 mol % to the total monomer amount composing the first network structure. In addition, the ratio of the monomer having a group capable of forming a complex with a metal ion is preferably from 1:1 to 1:1000, and more preferably from 1:10 to 1:100. The metal ion is not particularly limited as long as it is capable of forming a complex, examples of which include zinc, iron, nickel, cobalt and chromium ions. Examples of metal sources include water-soluble metal salts which, when dissolved in water, produce metal ions. A group capable of forming a complex with a metal ion refers to a group capable of forming a complex with a selected metal ion, examples of which include a carboxyl group, a sulfonic group and a phosphate group when a polyvalent metal, such as zinc, iron, nickel, cobalt or chromium is selected as a metal ion. As a monomer having a group capable of forming a complex with a metal ion, acrylic acid, methacrylic acid, itaconic acid, styrene sulfonic acid and vinyl phosphoric acid may be mentioned.

A specific example of the first preferred embodiment is an artificial meniscus which is based on a hydrogel having an interpenetrating network structure, the hydrogel being composed of a network structure having 2-acrylamido-2-methyl-propane sulfonic acid as the material monomer and a network structure having acrylamide as the material.

Next, description will be made on the case where a linear polymer or a network structure composing a semi-interpenetrating network structure or an interpenetrating network structure is a naturally occurring polymer, in particular bacterial cellulose (hereinafter referred to as "second preferred embodiment"). In this embodiment, one network structure is bacterial cellulose and the other network structure (in the case of an interpenetrating network structure) or the linear polymer (in the case of a semi-interpenetrating network structure) is preferably a polymer of an electrically charged unsaturated monomer and/or an electrically neutral unsaturated monomer or a crosslinked product thereof or a naturally occurring polymer or a crosslinked product thereof.

A specific example of the second preferred embodiment is an artificial meniscus which is based on a hydrogel having an interpenetrating network structure, the hydrogel being composed of a network structure consisting of bacterial cellulose and a network structure having N,N-dimethyl-acrylamide as the material monomer or of a network structure consisting of bacterial cellulose and a network structure consisting of gelatin.

Physical properties of the hydrogel according to this invention will then be described. First of all, this gel has a shear modulus of preferably 0.01 to 10 MPa, more preferably 0.03 to 3 MPa, and most preferably 0.1 to 1.0 MPa. Also this gel has a compression stress at rupture of preferably 0.1 to 100 MPa, more preferably 1 to 50 MPa, and most preferably 3 to 40 MPa. In addition, the gel has a tensile stress at rupture of preferably 0.1 to 100 MPa, more preferably 0.1 to 50 MPa, and most preferably 0.5 to 5 MPa.

Furthermore, the gel has a water content of 10% or more, more preferably 50% or more, and even more preferably 85% or more. The upper limit of the water content is not particularly defined, but is usually 99.9% or less, preferably 99% or less, and more preferably 95% or less, for the purpose of retaining mechanical strength of the gel, etc.

Next, a process for producing the artificial menisci according to this invention will be described by way of example (in the case of a first preferred embodiment). First, a solution containing a second monomer component (which contains 60 mol % or more of an electrically neutral unsaturated monomer) and a polymerization initiator (as well as a crosslinker, in the case of a hydrogel having an interpenetrating network structure) is prepared. Subsequently, a gel having a first network structure (a single network gel formed by polymerizing and crosslinking a first monomer component which contains 10 mol % or more of an electrically charged unsaturated monomer) is immersed in this solution and left for a sufficient period of time to allow the second monomer component and the polymerization initiator (as well as a crosslinker, in the case of a hydrogel having an interpenetrating network structure) to diffuse into the gel. The gel is then removed from the solution, and the second monomer component in the gel is polymerized (and crosslinked, in the case of a hydrogel having an interpenetrating network structure) to thereby form a second network structure which entwines with a first network structure (in the case of a hydrogel having an interpenetrating network structure) or a linear polymer (in the case of a hydrogel having a semi-interpenetrating network structure) so that a gel having a double network structure may be produced. In addition, it is also possible to produce, in a similar manner to the above procedure, a gel having a triple or more interpenetrating network structure, by using a gel having a multi-network structure instead of a single-network type gel as described above.

Aqueous solution polymerization is preferable as a method for polymerization. In addition, aqueous solution polymerization is preferably carried out while stirring and mixing in order to evenly disperse the second monomer component into the first network structure and to efficiently promote the reaction for forming the second network structure or the polymer. To this end, polymerization is more preferably carried out in a reaction vessel having a rotary agitator shaft, while granularizing a gel-like product produced in accompaniment with the polymerization by means of shear by the agitator shaft. Most preferably, a kneader is used as a reaction vessel having multiple rotary agitator shafts, as disclosed in Japanese Unexamined Patent Publication No. 1982-34,101, U.S. Pat. No. 4,625,001 and EP 0343,919, for example.

Polymerization initiators to be used for forming the first network structure, the second network structure (in the case of a gel having an interpenetrating network structure) and the linear polymer (in the case of gel having a semi-interpenetrating network structure) are not particularly limited and a variety of them may be used depending on organic monomers to be polymerized. For example, a water-soluble thermal catalyst such as potassium persulfate or a redox initiator such as potassium persulfate-sodium thiosulfate may be used in the case of thermally polymerizing AMPS, AAm or AA as an organic monomer, and 2-oxoglutaric acid may be used as a photosensitizer in the case of photopolymerization. In addition, thermal catalysts that are soluble in organic solvents, such as azobisisobutyronitrile (AIBN) and benzoyl peroxide (BPO) may be used in the case of thermally polymerizing St as an organic monomer, and benzophenone as a photosensitizer may be used in the case of photopolymerization.

Similarly, crosslinkers to be used for forming the first network structure or the second network structure (in the case of a gel having an interpenetrating network structure) are not particularly limited and a variety of them may be selected depending on organic monomers to be crosslinked. For example, N,N'-methylenebisacrylamide and ethylene glycol dimethacrylate may be used in the case of using AMPS, AAm or AA as an organic monomer and in the case of using St as an organic monomer, respectively.

In addition, the solvent for solution for immersing a gel having a first network structure is preferably the same as the solvent in the gel having the first network structure, in view of that any adverse effects on the gel to be immersed in the solution may be prevented and a double-network structure (a hydrogel having an interpenetrating network structure) or a linear polymer (a hydrogel having an semi-interpenetrating network structure) may be entwined well with the network of the first network structure.

With respect to an embodiment wherein a metal ion is introduced in the gel, the obtained hydrogel having a (semi) interpenetrating network structure is dried in vacuo and then immersed in the metal salt solution. In accordance with this manipulation, a complex may efficiently be formed with the metal ion by minimizing the distance between the networks.

Next, conditions and the like for polymerization and crosslinking will be described. First of all, polymerization reaction of a first monomer component diffused throughout a gel having a first network structure may be made either by heating or by irradiation with light such as ultraviolet radiation. The polymerization reaction is conducted under such conditions that the first network structure of the gel may not be destroyed. Also for crosslinking reaction, a crosslinker and a reaction initiator at predetermined concentrations, together with a second monomer component, are mixed into a solvent to diffuse them throughout the gel having the first network structure. Specifically, the gel having the first network structure is immersed in a second monomer solution containing a crosslinker to be diffused at a low temperature for 24 hours. In order to avoid crosslinking halfway through diffusion, a temperature at or below the room temperature, or around 4° C., is preferred.

Next, another process for producing the artificial menisci according to this invention will be described by way of example (in the case of a second preferred embodiment). This hydrogel can be produced by (1) culturing bacteria in a medium containing a polymer of an electrically charged unsaturated monomer and/or an electrically neutral unsaturated polymer or a crosslinked product thereof or a naturally occurring polymer or a crosslinked product thereof to thereby produce bacterial cellulose; or (2) introducing an electrically charged unsaturated monomer and/or an electrically neutral unsaturated monomer into the bacterial cellulose and then polymerizing the monomer component in the presence of a solvent to thereby form a polymer in a first network structure; or optionally, further crosslinking the polymer to thereby form a network structure also in the bacterial cellulose, or (3) impregnating the bacterial cellulose in a solution containing an electrically charged, naturally occurring polymer to incorporate the electrically charged, naturally occurring polymer into the bacterial cellulose.

In order to crosslink the monomer or naturally occurring polymer, a crosslinker (chemical crosslinker, ion crosslinker and so on) may be used. Water-soluble carbodiimide (WSC, EDC) may be mentioned as a chemical crosslinker and $CaCl_2$ may be mentioned as an ion crosslinker. In addition, gelatin, for example, will crosslink via hydrogen bonding at a certain concentration or higher with no crosslinker added. In this case, however, it may further be chemically crosslinked.

In the case of chemical crosslinking or ion crosslinking, when the degree of crosslinking is set in the range of $10^{-3}$ to $5 \times 10^{-2}$ M, a pliable and tough gel may be obtained, and when the degree of crosslinking is set in the range of $5 \times 10^{-2}$ to 2 M, preferably $10^{-1}$ to 1 M, a rigid and tough gel may be obtained.

The artificial meniscus should preferably be of the same shape as the natural meniscus. For shaping, a hydrogel having a (semi)interpenetrating network as produced may be cut or otherwise treated, or polymerization or crosslinking may be performed in a mold having such a shape. As will subsequently be described, the artificial meniscus should preferably have, on the side in contact with the bone, a protrusion integral with the gel body such that the protrusion may infiltrate into the bone.

Next, how to use the artificial meniscus according to the present invention will be described. For fixing the artificial meniscus, it is preferable that at where the artificial meniscus is in contact with the bone, the artificial meniscus is provided with a protrusion as described above, while the bone is bored so that the protrusion may be inserted into the bore. In this way, the fibrous tissues growing out from the bone will stick to the protrusion (gel) of the artificial meniscus to thereby securely fix the artificial meniscus to the bone. In addition, the gel and the ligaments are fixed by a nonabsorbable surgical suture.

For practical uses, since matching artificial menisci differ in shape between patients, it is advisable to prepare dozens of different shapes of them in advance. Then, by measuring the sizes (horizontal and vertical lengths and thickness of the knee) of each patient with CT, the most suitable meniscus will be selected.

EXAMPLES

The present invention is specifically demonstrated using Examples below, to which the present invention is not limited in any way.

Example 1

Preparation of Single-Network Type Gel

From a silicon plate having an area of 100 mm×100 mm and a thickness of 2 mm, a frame having outer sides of 80 mm×80 mm and a width of 5 mm was cut out with a cutter and a groove of 3 mm was bored on a location on the frame. This silicon frame was interposed between two glass plates each having an area of 100 mm×100 mm and a thickness of 3 mm to assemble a polymerization reactor.

25 ml of an aqueous solution of 2 mol/L 2-acrylamido-2-methylpropane sulfonic acid (AMPS) as a monomer, 1 ml of an aqueous solution of 2 mol/l N,N'-methylenebisacrylamide (MBAA) as a crosslinker and 1 ml of an aqueous solution of 0.1 mol/L 2-oxoglutaric acid as an initiator were combined and conditioned with water to obtain 50 ml of an aqueous solution. This solution was deoxygenated using nitrogen gas. Subsequently, the deoxygenated solution was poured into an opening of the silicon plate placed on one of the glass plates of the polymerization reactor and the other glass plate was superposed on the silicon plate to seal around the opening. Then, polymerization was carried out using a UV lamp having a wavelength of 365 nm (22 W, 0.34 A) to irradiate ultraviolet radiation at a normal temperature for six hours to prepare an AMPS gel (first network structure) having a degree of crosslinking of 4 mol %. The degree of crosslinking was calculated as follows:

$$\{(\text{aqueous MBAA solution concentration} \times \text{amount})/(\text{monomer concentration} \times \text{amount})\} \times 100 = \{(2 \text{ mol/L} \times 1 \text{ ml})/(2 \text{ mol/L} \times 25 \text{ ml})\} \times 100 = 4 \text{ mol \%}$$

Preparation of Double-Network Type Gel 40 ml of an aqueous solution of 5 mol/L acrylamide (AAm) as a monomer, 1 ml of an aqueous solution of 0.2 mol/L N,N'-methylenebisacrylamide (MBAA) as a crosslinker and 1 ml of an aqueous solution of 0.1 mol/L 2-oxoglutaric acid as an initiator were combined and conditioned with water to obtain 200 ml of an aqueous solution (immersion solution). This immersion solution was deoxygenated using a nitrogen gas.

Subsequently, the immersion solution and 4 g of the single-network type gel were placed in a sealed container having a volume sufficiently larger than the gel. The container was stored in a refrigerator at 4° C. for 24 hours to allow the monomer, the crosslinker and the initiator in the immersion solution to diffuse and penetrate into the gel. During this step, the container was gently shaken occasionally for the purpose of evening out the concentration of the immersion solution.

Next, the gel was removed from the immersion solution, cut to an appropriate size and then held between two glass plates of 100 mm in width, 100 mm in length and 3 mm in thickness, avoiding inclusion of air bubbles. After sealing the four circumference sides of the two glass plates, a UV lamp having a wavelength of 365 nm (22 W, 0.34 A) was used to irradiate ultraviolet radiation at a normal temperature for six hours, during which the AAm monomer diffused throughout the gel was polymerized to give a double-network type gel. The second network structure of this double-network type gel had a degree of crosslinking of 0.1 mol %. The degree of crosslinking was calculated as follows:

$$\{(0.2 \text{ mol/L} \times 1 \text{ ml})/(5 \text{ mol/L} \times 40 \text{ ml})\} \times 100 = 0.1 \text{ mol \%}$$

The double-network type gel of PAMPS-PAAm (poly-AMPS-poly-AAm) obtained in Example 1 was subject to equilibrium swelling in pure water. Elemental analysis was conducted on the gel. The results are shown in Table 1 below.

TABLE 1

|  |  | C (%) | H (%) | N (%) |
|---|---|---|---|---|
| double-network type gel | theoretical | 50.30 | 6.29 | 9.78 |
|  | found | 48.98 | 6.60 | 9.49 |

As seen clearly from Table 1 above, it was confirmed that the AAm monomer used for the second polymerization was crosslinked in the double-network type gel without exiting the gel through equilibrium and swelling, because nitrogen shows a value of 9.49% to the total amount of both the AMPS and AAm monomers.

Example 2

Preparation of Single-Network Type Gel 40 ml of an aqueous solution of 2 mol/L acrylic acid (AA) as a monomer, 4 ml of an aqueous solution of 0.2 mol/L N,N'-methylenebisacrylamide (MBAA) as a crosslinker and 1 ml of an aqueous solution of 0.1 mol/L 2-oxoglutaric acid as an initiator were combined and conditioned with water to obtain 80 ml of an aqueous solution. The solution was deoxygenated using a nitrogen gas. Subsequently, the deoxygenated solution was poured into an opening of a silicon plate placed on one of glass plates of a polymerization reactor similar to one in Example 1 and the other glass plate was superposed on the silicon plate to seal around the opening. Then, polymerization was carried out using a UV lamp having a wavelength of 365 nm (22 W, 0.34 A) to irradiate ultraviolet radiation at a normal temperature for six hours to prepare an AA gel having a degree of crosslinking of 1 mol %.

Preparation of Double-Network Type Gel 20 ml of an aqueous solution of 5 mol/L acrylamide (AAm) as a monomer, 1 ml of an aqueous solution of 0.1 mol/L N,N'-methylenebisacrylamide (MBAA) as a crosslinker and 1 ml of an aqueous solution of 0.1 mol/L 2-oxoglutaric acid as an initiator were combined and conditioned with water to obtain 200 ml of an aqueous solution (immersion solution). This immersion solution was deoxygenated using a nitrogen gas.

Subsequently, the immersion solution and 4 g of the single-network type gel were placed in a sealed container having a volume sufficiently larger than the gel. The container was stored in a refrigerator at 4° C. for 24 hours to allow the monomer, the crosslinker and the initiator in the immersion solution to diffuse and penetrate into the gel. During the step, the container was gently shaken occasionally for the purpose of evening out the concentration of the immersion solution.

Next, the gel was removed from the immersion solution, cut to an appropriate size and then held between two glass plates of 100 mm in width, 100 mm in length and 3 mm in thickness, avoiding inclusion of air bubbles. After sealing the four circumference sides of the two glass plates, a UV lamp having a wavelength of 365 nm (22 W, 0.34 A) was used to irradiate ultraviolet radiation at a normal temperature for six hours, during which the AAm monomer diffused throughout the gel was polymerized to give a double-network type gel. The second network structure of this double-network type gel had a degree of crosslinking of 0.1 mol %.

Test Example 1

Degree of swelling, compression stress at rupture and compression strain at rupture were measured for the double-network type gels obtained in Examples 1 and 2 and, for comparison, the single-network type gels prepared in Examples 1 and 2. The results are shown in Table 2 (single-network type gels) and 3 (double-network type gels).

TABLE 2

| monomer for polymerization, degree of crosslinking in parentheses | AMPS (15 mol %) | AA (2 mol %) |
|---|---|---|
| degree of swelling | 12 | 90 |
| compression stress at rupture (MPa) | 0.9 | 0.1 |
| compression strain at rupture (%) | 30 | 63 |

TABLE 3

| Ex. | degree of crosslinking of first network structure (mol %) | degree of crosslinking of second network structure (mol %) | compression stress at rupture (MPa) | compression strain at rupture (%) | water content | degree of shrinkage | monomer ratio 1st:2nd |
|---|---|---|---|---|---|---|---|
| 1 | 4 | 0.1 | 9.7 | 82 | 92 | 78 | 1:10 |
| 2 | 1 | 0.1 | 3 | 95 | 91 | 80 | 1:15 |

As clearly seen from Tables 2 and 3 above, it is found that the double-network type gel of PAMPS-PAAm of Example 1 has a higher compression stress at rupture than the AMPS single-network type gel. In addition, it is seen that the PAA-PAAm double-network type gel of Example 2 has a remarkably higher compression stress at rupture in comparison with the PAAm single-network type gel.

Example 3

In a similar manner as in Example 1, but altering the ratio between the monomers composing the first and second network structures and also altering the degrees of crosslinking of the first and second network structures, mechanical strength was measured. Below, an abbreviated designation is used for each double-network type gel, consisting of first monomer concentration (M), monomer name and degree of crosslinking (mol %)-second monomer concentration (M), monomer name and degree of crosslinking (mol %) in the mentioned order. For example, a double-network type gel in which a first network structure is PAMPS having a monomer concentration of 1 M and a degree of crosslinking of 4 mol %, and a second network structure is PAAm having a monomer concentration of 1 M and a degree of crosslinking of 0.1 mol % is designated as 1PAMPS4-1PAAm0.1. It should be noted that the monomer concentrations here are those at the time of production and differ from the monomer amounts in the final gel. In other words, when the concentrations of the first and second monomers are both 1 M, for example, their molar ratio in the final gel obtained will not be 1:1. It is understood that the first network structure is electrically charged, and therefore, swells largely in the neutral solution of the second monomer in water. (In this Example, the monomer amount in the final gel is AMPS:AAm=1:10.) The results are shown in Table 4, and FIGS. 3 and 4. From Table 4 and FIG. 3, it is seen that, for the double-network type gel based on PAMPS-PAAm, when the composition ratio between the monomers in the first and second network structures is altered, the rupture strength is at maximum with the monomer in the first network structure (PAMPS): the monomer in the second network structure (PAAm)=1:20. Also, from FIG. 4, it is seen that the strength varies largely depending on the degree of crosslinking of the second network structure (PAAm) and reaches a maximum when the degree is 0.1 mol %.

TABLE 4

| sample name | PAMPS:PAAm | degree of swelling | initial modulus (MPa) | rupture strength (MPa) | strain at rupture (%) |
|---|---|---|---|---|---|
| 1PAMPS4-0.5PAAm0.1 | 1:6 | 13 | 0.41 | 2.3 | 64 |
| 1PAMPS4-1PAAm0.1 | 1:10 | 12 | 0.37 | 9.5 | 82 |
| 1PAMPS4-2PAAm0.1 | 1:20 | 6.9 | 0.60 | 17 | 89 |
| 1PAMPS4-3PAAm0.1 | 1:30 | 5.2 | 0.75 | 15 | 86 |
| 1PAMPS4-5PAAm0.1 | 1:53 | 4.9 | 0.90 | 9.4 | 80 |

Example 4

First Network

AMPS and TFEA were mixed at a ratio of 1:5 into DMSO to a concentration of 3.0 ml/L, 1 mol % of a crosslinker MBAA and 0.2 mol % of a polymerization initiator α-ketoglutaric acid were added and synthesis was carried out by UV polymerization according to the same procedure described above.

Second Network 10 ml of the above gel were immersed in 200 ml of solution of TFEA in DMSO (concentration 3.0 ml/L, MBAA 0.1 mol % and α-ketoglutaric acid 0.2 mol %) and left for approximately two days and synthesis was carried out by UV polymerization according to the same procedure described above. Physical properties of the gel obtained in this manner are shown in Table 5.

TABLE 5

| Ex. | degree of crosslinking of first network structure (mol %) | degree of crosslinking of second network structure (mol %) | tensile stress at rupture (MPa) | tensile strain at rupture (%) | water content (%) | degree of shrinkage (%) | monomer ratio 1st:2nd |
|---|---|---|---|---|---|---|---|
| 4 | 1.0 | 0.1 | 2.2 | 410 | 29 | 100 | 1:6 |

Example 5

Various metal ions were introduced into the double-network type gel of 1PAMPS4-1PAAm0.1 obtained in Example 3 and mechanical strength was measured. For introducing the metal ions, the double-network type gel equilibrated and swollen in pure water was cut out to an appropriate size and once dried in vacuo. Aqueous solutions of various metal salts were then prepared in amounts 20-fold in relation to the volume of the gel as equilibrated and swollen, in which the gel was immersed for approximately one week. The aqueous solutions were prepared in three concentrations of 0.01 M, 0.1 M and 1 M for $ZnSO_4$ and three concentrations of 0.01 M, 0.1 M and 0.3 M for $FeCl_3$. The results are shown in Table 6.

TABLE 6

| | degree of swelling | initial modulus (MPa) | stress at rupture (MPa) | strain at rupture (%) | water content (%) | degree of shrinkage (%) |
|---|---|---|---|---|---|---|
| reference (swollen in pure water) | 12 | 0.35 | 0.7 | 100 | 92 | 78 |
| $Zn^{2+}$ (0.01 M) | 9 | 0.25 | 1.0 | 100 | 89 | 75 |

TABLE 6-continued

| | degree of swelling | initial modulus (MPa) | stress at rupture (MPa) | strain at rupture (%) | water content (%) | degree of shrinkage (%) |
|---|---|---|---|---|---|---|
| $Zn^{2+}$ (0.1 M) | 7 | 0.31 | 14.8 | 89 | 86 | 58 |
| $Zn^{2+}$ (1 M) | 3 | 0.30 | 17.6 | 88 | 67 | 25 |
| $Fe^{3+}$ (0.01 M) | 4 | 0.21 | 41.2 | 95 | 75 | 33 |
| $Fe^{3+}$ (0.1 M) | 6 | 0.14 | 15.8 | 88 | 83 | 50 |
| $Fe^{3+}$ (0.3 M) | 6 | 0.13 | 14.2 | 88 | 83 | 50 |

Test Example 2

Stress Dispersibility Test

According to the same procedure as above, various double-network type hydrogels of PAMPS-PAAm were prepared. These hydrogels were cut to 60×30×10 mm.

The experimentation used for this example is shown in FIG. 5. As a light source 4, an He—Ne laser (Model 127, Spectra-Physics Laser, Inc.) was used. The axis of a polarizer 5 was vertically oriented and the axis of an analyzer 9 was horizontally oriented. The fast axes of two ¼ plates 6 and 8 were set at π/4 and −π/4 radians respectively in relation to the axes of the polarizer 5 and the analyzer 9. Photoelastic images were recorded with a cooled CCD camera (C4742-95, Hamamatsu Co., Japan) linked with a personal computer 11 (the entire image area includes 1280×1024 pixels).

Image views showing the degree of stress dispersion photographed by this CCD camera are shown in FIG. 6. Discolored areas (which appear white in the views) imply concentration of stress. As seen therefrom, the image (a) of the PAMPS-PAAm hydrogel (the degree of crosslinking of PAAm is 0.1 mol %) has less discolored areas in comparison with the image (b) of the PAMPS-PAAm hydrogel (the degree of crosslinking of PAAm is 2 mol %). Thus, it is seen that the hydrogel according to the present invention, whose mechanical strength is optimized, is excellent in stress dispersibility.

In addition, normalized power and strain were tested while altering the degree of crosslinking of PAAm (0.0 mol %, 0.1 mol %, 0.5 mol %, 1.0 mol % and 2.0 mol %). The results are shown in FIG. 7. From FIG. 7, it is seen that there is a trend that the lower the degree of crosslinking of the second network structure is, the better the stress is dispersed at the same strain and the less the normalized power is. In addition, FIG. 8 illustrates the relationship between the normalized power and the degree of crosslinking and it is seen from this drawing that the normalized power is at minimum when the degree of crosslinking is around 0.1 mol % with respect to any strain.

Finally, intensity and strain were tested, altering the concentration of AAm (0.5 M, 1 M, 2 M, 3 M and 5 M) with a fixed degree of crosslinking (0.1 mol %). The results are shown in FIG. 9. It is seen from this drawing that the intensity tends to be higher at the same strain when the concentration of AAm is higher and that the intensity is at minimum when the concentration of AAm is 1 M. In other words, the DN gel, whose mechanical strength is optimized, has the highest capability of dispersing stress.

Example 6

Production of BC/Gelatin Double-Network Gel [1]

A charge of Bacto Pepton 0.5%, yeast extract 0.5%, disodium hydrogen phosphate 0.27%, citric acid 0.115% and glucose 2% was dissolved in deionized water to obtain HS medium. Then, gelatin was mixed into this medium up to 15% by weight to the medium, and the medium was dispensed to Erlenmeyer flasks in amounts ranging from 15 to 30 ml. The flasks were then capped and autoclaved at 120° C. for 20 minutes. Then, acetic bacterium (ATCC 53582) stored at −80° C. was taken out and inoculated to the medium. After incubation at 28 to 30° C. for about two to three days, bacterial cellulose began to be produced from the air-interfacing side of the medium and the culture was continued up to a thickness of about 2 mm. The bacterial cellulose/gelatin double-network gel obtained was washed with 1% NaOH solution for one day and the solvent was exchanged with pure water for two days to provide the title gel. The gel showed a degree of swelling of 30.

Example 7

Production of BC/Gelatin Double-Network Gel [2]

The title gel was produced in a manner similar to Example 6, except that the gelatin was mixed up to 20% by weight to the medium. The gel showed a degree of swelling of 36.

Comparative Example 1

Production of BC Single-Network Gel

The title gel was produced in a manner similar to Example 6, except that the gelatin was not mixed. The gel showed a degree of swelling of 89.

Test Example 3

Tensile Test

The gelatin-containing bacterial cellulose obtained was subjected to tensile testing. The tensile testing was carried out using a TENSILON tester with samples cut into strip specimens of 5 mm×1.5 mm×30 mm at a tensile rate of 1 mm/min. The results are shown in FIG. 10 and Table 7.

TABLE 7

| sample | stress at rupture (MPa) | strain at rupture | initial modulus (MPa) |
|---|---|---|---|
| Example 6 | 1.15 | 0.12 | 9.027 |
| Example 7 | 0.83 | 0.99 | 6.268 |
| Comparative Example 1 | 0.64 | 0.45 | 0.037 |

Example 8

Production of BC/Sodium Alginate Double-Network Gel

The title gel was produced in a manner similar to Example 6, except that sodium alginate was mixed up to 2% by weight to the medium and that the gel was immersed in 0.1 M $CaCl_2$ solution for two days in order to crosslink the polysaccharide moiety with $Ca^{2+}$ ion. The gel showed a degree of swelling of 20.

Example 9

Production of BC/Gellan Gum Double-Network Gel

The title gel was produced in a manner similar to Example 8, except that gellan gum was mixed up to 0.4% by weight to the medium. The gel showed a degree of swelling of 28.

Comparative Example 2

Production of BC Single-Network Gel

The title gel was produced in a manner similar to Example 6. The gel showed a degree of swelling of 36.

Test Example 4

Tensile Test

The gels from Examples 8, 9 and Comparative Example 2 were subjected to tensile testing in a manner similar to Test Example 3. The results are shown in FIGS. 11, 12 and Table 8.

TABLE 8

| sample | stress at rupture (MPa) | strain at rupture | initial modulus (MPa) |
|---|---|---|---|
| Example 8 | 1.06 | 0.11 | 10.625 |
| Example 9 | 1.06 | 0.09 | 14.464 |
| Comparative Example 2 | 1.40 | 0.23 | 2.655 |

Example 10

Production of BC/Gelatin Double-Network Gel [3]

A commercially available nata de coco (degree of swelling: 189) was immersed in and impregnated with a solution of 40% by weight gelatin in water at 80° C. for three days. The title gel, brownish-red in color, was obtained as a result. The gel showed a degree of swelling of 3.6.

Example 11

Production of BC/Gelatin Double-Network Gel [4]

The gel obtained in Example 10 was immersed in 1 M WSC solution in order to crosslink the gelatin within the gel. The obtained gel showed a degree of swelling of 5.2.

Test Example 5

Compression Test

The compression test was carried out using a TENSILON tester with samples cut into rectangular solid specimens of 10 mm×10 mm×5 mm at a compression rate of 10%/min in relation to sample thickness. The results are shown in FIG. 13 and Table 9.

TABLE 9

| sample | stress at rupture (MPa) | strain at rupture | initial modulus (MPa) |
|---|---|---|---|
| commercial BC | — | — | 0.003 |
| Example 10 | — | — | 0.038 |
| Example 11 | 1.23 | 0.61 | 1.167 |

Examples 12 to 15 and Comparative Example 3

Production of Various DN Gels

After one week of immersion in solutions of gelatin (Example 7: 30% by weight, 50° C., pH7), polysaccharides {sodium alginate (Example 8: 4% by weight, 70° C.), ι-carrageenan (Example 9: 5% by weight, 70° C.) and gellan gum (Example 10: 3% by weight, 70° C.)}, 1 M WSC (chemical crosslinking) and 0.1 M $CaCl_2$ (ion crosslinking) were prepared for BC/gelatin and BC/polysaccharide, respectively, to immerse each sample for four days. Then, the solvent was exchanged with pure water for one week for solvent exchange. Other conditions than those above for production were the same as in Example 6. The degrees of swelling of the gels from Examples 12 to 15 thus obtained were, in that order, 4.6, 20, 30 and 27. Also, the degree of swelling of bacterial cellulose gel prepared for comparison was 89.

Test Example 6

Tensile and Compression Tests

The compression test was carried out using a TENSILON tester with samples cut into cylindrical specimens of 9 mm in diameter×5 mm at a compression rate of 10%/min in relation to sample thickness. Also, the tensile testing was carried out using the same tester with samples cut into strip specimens of 5 mm×2 mm×30 mm and further cut into dumbbell specimens with a circular cutter having a diameter of 25 mm at a tensile rate of 10%/min in relation to the natural length of the samples. The results are shown in FIGS. 14 to 21 and Table 10.

TABLE 10

| | compression testing | | | tensile testing | | |
|---|---|---|---|---|---|---|
| sample | stress at rupture (MPa) | strain at rupture | initial modulus (MPa) | stress at rupture (MPa) | strain at rupture | initial modulus (MPa) |
| Comparative Example 3 | — | — | 0.007 | 2.2 | 0.21 | 5.2 |
| Example 12 | 3.7 | 0.37 | 1.7 | 2.8 | 0.17 | 23 |
| Example 13 | — | — | 0.61 | 2.2 | 0.3 | 6.7 |
| Example 14 | — | — | 0.12 | 0.5 | 0.26 | 1.8 |
| Example 15 | — | — | 0.38 | 1.16 | 0.37 | 2.3 |

As seen from the results, first with respect to the compression testing, the initial modulus values showed approximately one to two-digit increase in comparison to Comparative Example 3. For example, in the DN gel of Example 12, the initial modulus shows a very high value of 1.7 MPa while the breaking point at a strain of 40% shows a high value of approximately 4 MPa. It is surprising that mechanical properties as high as those are exhibited only with naturally occurring materials without using synthetic polymers. In addition, with respect to the tensile testing, since the bacterial cellulose is by nature a very "tensioning-resistant" material, significant increases as those found in the compression test such that the order of modulus may change were not observed for the polysaccharides. On the other hand, the gelatin showed a very high value of 23 MPa. No conventional DN gels have ever shown values in this vicinity. Also the gelatin showed a high stress of approximately 3 MPa.

Test Example 7

Confirmation Test of Changes in Physical Properties by Altering Concentrations of Gelatin and Condensation Agent (EDC) in BC/Gelatin Double-Network Gel BC single-network gel (Comparative Example 4) obtained in a manner similar to Comparative Example 2 was immersed in a solution of 30% by weight gelatin in water (50° C., pH7) for one week. Then, aqueous EDC solution in varied concentrations (0.1 M, 1 M) were prepared, in which each sample was immersed for four days. Further, the solvent was exchanged with pure water for one week to obtain the title gels of Examples 16 (aqueous EDC solution: 0.1 M) and 17 (aqueous EDC solution: 1 M). Also, BC single-network gel (Comparative Example 4) obtained in a manner similar to Comparative Example 2 was immersed in solutions of gelatin in water in varied concentrations (15%, 30%, 40% and 50%; 50° C., pH7) for one week. Then, 1 M aqueous EDC solution was prepared, in which each sample was immersed for four days. Further, the solvent was exchanged with pure water for one week to obtain the title gels of Examples 18 to 21 (Example 18: gelatin 15%, Example 19: gelatin 30%, Example 20: gelatin 40% and Example 21: gelatin 50%). Mechanical properties of these gels were measured according to the procedure for the method described below.

Compression Testing

Measurements were made using a TENSIRON tester with samples cut into cylindrical specimens 9 mm in diameter×5 mm at a compression rate of 10%/min in relation to sample thickness.

Tensile Testing

Measurements were made using a TENSIRON tester with samples cut into strip specimens of 5 mm×2 mm×30 mm and further cut into dumbbell specimens with a circular cutter 25 mm in diameter at a tensile rate of 10%/min in relation to the natural length of the samples.

The results are shown in Table 11 and FIGS. 22 to 25.

TABLE 11

| | | compression testing | | | tensile testing | | |
|---|---|---|---|---|---|---|---|
| sample | q | stress at rupture (MPa) | strain at rupture | initial modulus (MPa) | stress at rupture (MPa) | strain at rupture | initial modulus (MPa) |
| BC (Comparative Example 4) | 120 | — | — | 0.007 | 2.2 | 0.21 | 2.9 |
| BC + gelatin 0.1 M EDC (Example 16) | 5.3 | 3.0 | 0.48 | 1.2 | 2.2 | 0.22 | 11 |
| BC + gelatin 1 M EDC (Example 17) | 4.6 | 3.7 | 0.37 | 1.7 | 2.8 | 0.17 | 23 |
| BC + gelatin (15%) (Example 18) | 11 | 2.1 | 0.41 | 1.3 | 1.1 | 0.22 | 5.0 |
| BC + gelatin (30%) (Example 19) | 4.6 | 3.7 | 0.37 | 1.7 | 2.8 | 0.17 | 23 |
| BC + gelatin (40%) (Example 20) | 3.6 | 5.2 | 0.36 | 2.8 | 3.7 | 0.23 | 19 |
| BC + gelatin (50%) (Example 21) | 3.1 | 5.3 | 0.44 | 3.9 | 3.8 | 0.28 | 21 |

Test Example 8

Testing for Mechanical Properties of Bacterial Cellulose/Gelatin Double-Network Gel in Saline The bacterial cellulose/gelatin double-network gels used in Test Example 7 (gelatin concentrations as of production X=5, 15, 30, 40 and 50% by weight) were immersed in 1 M aqueous EDC solution for four days. Further, the solvent was exchanged for pure water for one week. Samples hereinafter will be designated as BC-gelatin (x %).

(1) Test Example 8-1

In order to provide for measurements in environment as close as possible to in vivo, compression and tensile testing was carried out using saline (0.1 M aqueous NaCl solution) as the solvent for BC-gelatin gel. At the same time, ion strength was altered to see if values of mechanical and physical properties would change. BC-gelatin (30) gel was used as a sample and three aqueous NaCl solutions (0.001, 0.01 and 0.1 M) were prepared for solvent exchange for one week. These samples were subjected to compression and tensile testing in the same manner as in Test Example 7. The results are shown in Tables 12 and 13, and FIGS. 26 and 27.

TABLE 12

| sample name | q | stress at rupture (MPa) | strain at rupture | initial modulus (MPa) |
|---|---|---|---|---|
| BC + gelatin in water | 5.8 | 3.7 | 0.37 | 1.7 |
| BC + gelatin 0.001 M NaCl | 5.4 | 3.4 | 0.34 | 2.4 |
| BC + gelatin 0.01 M NaCl | 4.9 | 4.4 | 0.36 | 1.5 |
| BC + gelatin 0.1 M NaCl | 4.6 | 3.0 | 0.41 | 0.9 |
| gelatin in water | 10 | 0.12 | 0.35 | 0.16 |
| gelatin 0.001 M NaCl | 7.0 | 0.11 | 0.39 | 0.15 |
| gelatin 0.01 M NaCl | 6.7 | 0.14 | 0.42 | 0.09 |
| gelatin 0.1 M NaCl | 6.1 | 0.12 | 0.45 | 0.07 |
| BC in water | 89 | — | — | 0.007 |

TABLE 12-continued

| sample name | q | stress at rupture (MPa) | strain at rupture | initial modulus (MPa) |
|---|---|---|---|---|
| BC 0.001 M NaCl | 88 | — | — | 0.010 |
| BC 0.01 M NaCl | 88 | — | — | 0.007 |
| BC 0.1 M NaCl | 80 | — | — | 0.009 |

TABLE 13

| sample name | q | stress at rupture (MPa) | strain at rupture | initial modulus (MPa) |
|---|---|---|---|---|
| BC + gelatin in water | 5.8 | 3.3 | 0.17 | 22 |
| BC + gelatin 0.001 M NaCl | 5.4 | 3.3 | 0.17 | 21 |
| BC + gelatin 0.01 M NaCl | 4.9 | 3.8 | 0.17 | 23 |
| BC + gelatin 0.1 M NaCl | 4.6 | 3.8 | 0.19 | 19 |
| gelatin in water | 10 | 0.068 | 0.32 | 0.20 |
| gelatin 0.001 M NaCl | 7.0 | 0.078 | 0.36 | 0.21 |
| gelatin 0.01 M NaCl | 6.7 | 0.087 | 0.37 | 0.22 |
| gelatin 0.1 M NaCl | 6.1 | 0.085 | 0.33 | 0.25 |
| BC in water | 89 | 2.2 | 0.21 | 2.9 |
| BC 0.001 M NaCl | 88 | 2.3 | 0.22 | 2.4 |
| BC 0.01 M NaCl | 88 | 3.2 | 0.27 | 3.5 |
| BC 0.1 M NaCl | 80 | 2.9 | 0.22 | 2.7 |

(2) Test Example 8-2

Although BC alone is in nature unable to restore once it has largely deformed, cycle testing by compression was carried out to see if inclusion of gelatin as an electrolyte makes it capable of returning from deformation.

Compression testing was carried out on a sample (BC-gelatin (50)) using a TENSILON tester. The sample was made into cylindrical specimens approximately 9 mm in diameter×5 mm and compression rate was set at 10%/min in relation to the sample thickness. Cycling was repeated five times, up to a strain of 30%, respectively.

It was found from FIGS. 28 to 30 that, in each case, the rise on the first outward path is early and that the second and later outward paths and the whole homeward path follow approximately fixed courses. As seen from FIG. 30, even when the load was removed, reversion force is small and the drop on the homeward path is large. This is considered indicative of low restoration of BC. In FIGS. 28 and 29, the second and later rises appear at a strain of approximately 7%, while in FIG. 30, they appear at a strain of approximately 12%, which makes it understandable that properties of gelatin strongly appear on the second or later cycles of DN.

Studying FIG. 28 from a material viewpoint, it is seen that the gel is a durable material since it keeps a high modulus under continued application of strain on the edge of rupture and withstands a large load.

(3) Test Example 8-3

Experiment was carried out to see how much water-retaining capability has increased by addition of electrolytes to BC. Compression testing was carried out according to Test Example 7. BC-gelatin (x %) was used as a sample. Compression was stopped at a strain of 30%, water around the gel was removed, and then water retention was estimated by measuring the weight of the gel before and after the compression.

Weight was estimated by $W_{water} = W_{polymer} \times (q-1)$

Reduction rate of water $A = (W_{before} \times \alpha - W_{after}) / W_{water}$ Residual amount of water $B = 1 - A$ (in %)

wherein α: corrected value in uncompressed state (evaporation into atmosphere)

FIG. 31 shows the relationship between the concentrations of gelatin to be impregnated in BC and the residual amount of water. It is seen that since the strain applied to the gel was 30%, BC alone (0% gelatin) has 80% of water remaining, while gradual increase of gelatin concentrations will increase the residual amount in DN, showing close values between DN and the gelatin SN at gelatin concentrations of 40 and 50%.

Example 22

Production of BC/PDMAA Double-Network Gel 100 ml of an aqueous solution of 6 mol/L N,N-dimethyl-acrylamide (DMAA) as a monomer, 2 ml of an aqueous solution of 0.1 mol/L N,N'-methylenebisacrylamide (MBAA) as a crosslinker and 2 ml of an aqueous solution of 0.1 mol/L potassium persulfate as an initiator were combined and conditioned with water to obtain 200 ml of an aqueous solution (immersion solution). This solution was deoxygenated for 30 minutes using a nitrogen gas.

Subsequently, the immersion solution and 4 g of the BC single-network type gel obtained in Comparative Example 1 were placed in a sealed container having a capacity sufficiently larger than the gel. The container was left in a refrigerator at 4° C. for two days to allow the monomer, the crosslinker and the initiator in the immersion solution to diffuse and penetrate into the gel. During this step, the container was gently shaken occasionally for the purpose of evening out the concentration of the immersion solution.

Next, the gel was removed from the immersion solution, cut to an appropriate size and then held between two glass plates 100 mm in width, 100 mm in length and 3 mm in thickness, avoiding inclusion of air bubbles. After sealing the four circumference sides of the two glass plates, the DMAA monomer was polymerized in a water bath at 60° C. for six hours to obtain the title double-network type gel.

Example 23

Production of PAMPS/PDMAA Double-Network Gel 25 ml of an aqueous solution of 2 mol/L 2-acrylamido-2-methylpropane sulfonic acid (AMPS) as a monomer, 1 ml of an aqueous solution of 2 mol/L N,N'-methylenebisacrylamide (MBAA) as a crosslinker and 0.5 ml of an aqueous solution of 0.1 mol/L 2-oxoglutaric acid as an initiator were combined and conditioned with water to obtain 50 ml of an aqueous solution. This solution was deoxygenated using a nitrogen gas. Subsequently, the deoxygenated solution was poured into an opening of a silicon plate placed on one of the glass plates of the polymerization reactor and the other glass plate was superposed on the silicon plate to seal around the opening. Then, polymerization was carried out using a UV lamp having a wavelength of 365 nm (22 W, 0.34 A) to irradiate ultraviolet radiation at a normal temperature for six hours to prepare an AMPS gel (first network structure) having a degree of crosslinking of 4 mol %.

Next, 100 ml of an aqueous solution of 6 mol/L N,N-dimethyl-acrylamide (DMAA) as a monomer, 2 ml of an aqueous solution of 0.1 mol/L N,N'-methylenebisacrylamide (MBAA) as a crosslinker and 2 ml of an aqueous solution of 0.1 mol/L potassium persulfate as an initiator were combined and conditioned with water to obtain 200 ml of an aqueous solution (immersion solution). This solution was deoxygenated for 30 minutes using a nitrogen gas.

Then, the PAMPS single-network type gel was placed in a sealed container having a capacity sufficiently larger than the gel. The container was left in a refrigerator at 4° C. for two days to allow the monomer, the crosslinker and the initiator in the immersion solution to diffuse and penetrate into the gel. During this step, the container was gently shaken occasionally for the purpose of evening out the concentration of the immersion solution.

Then, the gel was removed from the immersion solution, cut to an appropriate size and then held between two glass plates 100 mm in width, 100 mm in length and 3 mm in thickness, avoiding inclusion of air bubbles. After sealing the four circumference sides of the two glass plates, the DMAA monomer was polymerized in a water bath at 60° C. for six hours to obtain the title double-network type gel.

Test Example 9

Evaluation of In Vivo Durability (Subcutaneous Implantation Experiment)

The DN type hydrogel of PAMPS/PDMAA of Example 23, the bacterial cellulose/gelatin DN type hydrogel of Example 12 and the DN type hydrogel of bacterial cellulose/PDMAA of Example 22 were subjected to the title test according to the following protocol.
1. Material and Method
1) Gel Material
size 10 mm×10 mm×5 mm, two
2) Animal Used
One white male rabbit (body weight 3 kg or more but less than 4 kg)
3) Sterilization
Disinfect with Isodine for 10 minutes and then immerse in an antibiotic agent (Minomycin 1 g, 48 hours).
Implant gel material at three locations spaced apart symmetrically across the backbone of the animal.
Make an incision about 2 cm in size on the skin over the paraspinal muscles on the back of the animal to make subcutaneous ablation to acquire space for implantation, before implanting one gel material followed by cutaneous suture.
Keep the animal for six weeks in a cage after operation.
4) Implantation Experiment
[1] Implantation group: sterilize one gel, followed by subcutaneous implantation for six weeks.
[2] Control group (disinfection only): disinfect one gel, followed by keeping it in distilled water for six weeks.
5) Examinations
Condition around the operation wound on the back of the animal
Condition around the subcutaneous gel
Formation and deformation of the gel
Changes in mechanical properties (maximum rupture strength, strain at rupture, initial modulus).
2. Results
Implantation group: the animal showed no severe infection and was sacrificed after six weeks.
The gel material was recovered and subjected to destructive testing after two hours at CAST.

Example 23

Condition on the Back
Mild bulging observed at the gel implantation site, but no marked redness or heat (circular inset upper in FIG. 32).
Condition Around the Subcutaneous Gel
Film formed around the gel. No marked signs of infection observed {FIG. 33 (1) and (2)}.
Formation and Deformation of the Gel
size 9.63×10.19×4.88
Substantially no changes observed compared with the condition before implantation, remaining as original (FIG. 34).

TABLE 14

Results of mechanical testing

| PAMPS-PDMAA | breaking stress (MPa) | strain at rupture | initial modulus (MPa) |
|---|---|---|---|
| control group | 6.0 | 78% | 0.49 |
| sterilization group | 7.49 | 78% | 0.52 |
| implantation group | 12.6 | 84% | 0.40 |

*control group: untreated
*sterilization group: sterilization (antibiotic agent & Isodine immersion) followed by six weeks in distilled water
*implantation group: sterilization followed by subcutaneous implantation for six weeks Example 12

Condition on the Back

Mild bulging observed at the gel implantation site, but no marked redness or heat (circular inset lower-left in FIG. 32).
Condition Around the Subcutaneous Gel
Film formed around the gel. No marked signs of infection observed {FIG. 35 (1) and (2)}.
Formation and Deformation of the Gel
size 9.63×10.19×4.88
Slight changes observed compared with the condition before implantation, but remaining substantially as original (FIG. 36).

TABLE 15

Results of mechanical testing

| cellulose-gelatin | breaking stress (MPa) | strain at rupture | initial modulus (MPa) |
|---|---|---|---|
| control group | 3.7 | 37% | 1.7 |
| sterilization group | 1.9 | 30% | 2.2 |
| implantation group | 3.5 | 58% | 0.34 |

*control group: untreated
*sterilization group: sterilization (antibiotic agent & Isodine immersion) followed by six weeks in distilled water
*implantation group: sterilization followed by subcutaneous implantation for six weeks Example 22

Condition on the Back

Mild bulging observed at the gel implantation site, but no marked redness or heat (circular inset lower-right in FIG. 32).
Condition Around the Subcutaneous Gel
Film formed around the gel. No marked signs of infection observed (FIG. 37).
Formation and Deformation of the Gel
size 9.63×10.19×4.88
Substantially no change observed compared with the condition before implantation, remaining as original.

TABLE 16

Results of mechanical testing

| cellulose-PDMAA | breaking stress (MPa) | strain at rupture | initial modulus (MPa) |
|---|---|---|---|
| control group | 2.9 | 50% | 1.6 |
| sterilization group | 2.3 | 42% | 1.5 |
| implantation group | 1.3 | 35% | 1.4 |

*control group: untreated
*sterilization group: sterilization (antibiotic & Isodine immersion) followed by six weeks in distilled water
*implantation group: sterilization followed by subcutaneous implantation for six weeks

Test Example 10 In Vivo Implantation

Method of Experiment

Laboratory animals were two female white rabbits. Pentobarbital sodium diluted two-fold with saline was intravenously injected for anesthesia. At first, dose was set at 1 ml/kg and additional dosing was made as necessary during operation, totaling approximately 6 ml. A longitudinal incision was made on the skin over the knee joint and the joint capsule inside the kneepan was incised to gain access into the joint. Medial collateral ligament was partially ablated at its attachment to the femur with the ossicle to dilate the joint to ablate the medial meniscus. In accordance with the size of the ablated meniscus, a disc-shaped meniscus (1 mm in thickness) was prepared from an presterilized plate made of PAMPS-PDMAA gel produced according to Example 23 and inserted into the medial joint spatium and the surroundings were sutured to the joint capsule. Then, the incised joint capsule was rigidly sutured and the medial collateral ligament was reconstructed at its attachment to the femur. Finally, cutaneous suture was made. After operation, the animals were kept in a cage (40×60×40 cm) and sacrificed under pentobarbital anesthesia after four weeks.

Results

At the time of sacrifice, no changes in body weight were observed (2.1 kg to 2.1 kg for one animal and 2.6 kg to 2.7 kg for the other) with no health problems {FIG. 38 (1)}. No inflammation, heat or redness was observed around the knee joint {FIG. 38 (2)}. In addition, no inflammation or foreign-body reaction was observed around the artificial meniscus made of PAMPS-PDMAA gel, with no marked modification on the opposite cartilage {FIG. 39 (1) at the time of operation and FIG. 39 (2) immediately before extraction}. Simultaneously, no deformation or modification was observed for the artificial meniscus {FIG. 40 (1) before experiment and FIG. 40 (2) after experiment}. Also, photomicrographs of the tissues are shown in FIGS. 41 to 43. FIGS. 41 (1) and 41 (2) show photographs of the femur cartilage stained with (1) HE and (2) safranin O, showing that the cartilage structure and dye-affinity were normal. FIG. 42 shows a photograph of the tibial cartilage (stained with safranin O) showing that the cartilage structure and dye-affinity were normal. FIG. 43 shows a photograph of the synovia (stained with HE) showing mild infiltration of small round cells, but no marked inflammation.

The invention claimed is:

1. An artificial meniscus, a base material of which is a hydrogel having a semi-interpenetrating network structure or an interpenetrating network structure wherein the hydrogel is produced by a process comprising:

a first step of polymerizing and crosslinking a first monomer component, of which 10 mol % or more is an electrically charged unsaturated monomer selected from the group consisting of 2-acrylamido-2-methylpropane-sulfonic acid, acrylic acid, methacrylic acid and a salt thereof, in the presence of a solvent, to thereby form a first network structure; and a second step of introducing a second monomer component, of which 60 mol % or more is an electrically neutral unsaturated monomer selected from the group consisting of acrylamide, N-isopropylacrylamide, N,N-dimethyl-acrylamide, vinylpyridine, styrene, methylmethacrylate, fluorine-containing unsaturated monomer, hydroxyethyl acrylate and vinyl acetate, into the first network structure and then polymerizing the second monomer component in the presence of a solvent, to thereby form a polymer in the first network structure; or optionally, further crosslinking the polymer to thereby form a second network structure in the first network structure, and in the case of the second monomer component being polymerized and crosslinked, the degree of crosslinking is set to be lower than the degree of crosslinking when the first monomer component is polymerized and crosslinked and wherein the molar ratio in amount of the first monomer component to the second monomer component is from 1:2 to 1:100 wherein the hydrogel has a compression stress at rupture of 3 to 40 MPa.

2. The artificial meniscus according to claim 1, wherein the hydrogel contains a metal ion, and a linear polymer or a network structure composing the hydrogel has a group capable of forming a complex with the metal ion.

3. The artificial meniscus according to claim 1, wherein the hydrogel is composed of (i) a network structure having 2-acrylamido-2-methylpropane sulfonic acid as a material monomer and (ii) a network structure having acrylamide or N,N-dimethyl-acrylamide as a material monomer.

4. A process for producing the artificial meniscus based on a hydrogel having a semi-interpenetrating network structure or an interpenetrating network structure of claim 1 wherein a linear polymer or a network structure composing the hydrogel is a polymer of an electrically charged unsaturated monomer and/or an electrically neutral unsaturated monomer or a crosslinked product thereof, comprising a first step of polymerizing and crosslinking a first monomer component, of which 10 mol % or more is an electrically charged unsaturated monomer, in the presence of a solvent, to thereby form a first network structure; and a second step of introducing a second monomer component, of which 60 mol % or more is an electrically neutral unsaturated monomer, into the first network structure and then polymerizing the second monomer component in the presence of a solvent to thereby form a polymer in the first network structure; or optionally, further crosslinking the polymer to thereby form a second network structure in the first network structure, wherein in the case of the second monomer component being polymerized and crosslinked, the degree of crosslinking is set to be lower than the degree of crosslinking when the first monomer component is polymerized and crosslinked and wherein the molar ratio in amount of the first monomer component to the second monomer component is from 1:2 to 1:100.

5. The process according to claim 4, wherein a crosslinker is used in an amount of 0.1 to 50 mol % to the first monomer component and a crosslinker is used in an amount of 0.001 to 20 mol % to the second monomer component.

6. The process according to claim 5, wherein the polymerization and/or crosslinking in the first step and/or the second step are carried out in an aqueous solution.

7. The process according to claim 4, wherein the polymerization and/or crosslinking in the first step and/or the second step are carried out in an aqueous solution.

* * * * *